(12) United States Patent
Hargrove

(10) Patent No.: US 8,494,625 B2
(45) Date of Patent: Jul. 23, 2013

(54) METHODS AND APPARATUS FOR ELECTRICAL STIMULATION OF TISSUES USING SIGNALS THAT MINIMIZE THE EFFECTS OF TISSUE IMPEDANCE

(75) Inventor: Jeffrey B. Hargrove, Bancroft, MI (US)

(73) Assignee: Cerephex Corporation, Bancroft, MI (US)

( * ) Notice: Subject to any disclaimer, the term of this patent is extended or adjusted under 35 U.S.C. 154(b) by 1207 days.

(21) Appl. No.: 12/187,375

(22) Filed: Aug. 6, 2008

(65) Prior Publication Data

US 2009/0030476 A1    Jan. 29, 2009

Related U.S. Application Data

(63) Continuation-in-part of application No. 11/490,255, filed on Jul. 21, 2006, now Pat. No. 7,715,910, which is a continuation of application No. 10/357,503, filed on Feb. 4, 2003, now abandoned.

(60) Provisional application No. 60/963,486, filed on Aug. 6, 2007, provisional application No. 61/014,917, filed on Dec. 19, 2007, provisional application No. 61/024,641, filed on Jan. 30, 2008, provisional application No. 61/032,241, filed on Feb. 28, 2008, provisional application No. 60/353,234, filed on Feb. 4, 2002.

(51) Int. Cl.
*A61N 1/00* (2006.01)

(52) U.S. Cl.
USPC .................................. 607/2; 607/46

(58) Field of Classification Search
USPC ............. 600/544, 545, 559, 27, 28; 607/45, 607/41
See application file for complete search history.

(56) References Cited

U.S. PATENT DOCUMENTS

| | | | |
|---|---|---|---|
| 4,612,934 A * | 9/1986 | Borkan | 607/62 |
| 5,851,223 A | 12/1998 | Liss et al. | |
| 6,016,449 A * | 1/2000 | Fischell et al. | 607/45 |
| 6,161,048 A | 12/2000 | Sluijter et al. | |
| 6,308,102 B1 | 10/2001 | Sieracki et al. | |
| 6,463,328 B1 | 10/2002 | John | |
| 6,662,053 B2 | 12/2003 | Borkan | |
| 6,678,562 B1 | 1/2004 | Tepper et al. | |
| 6,745,079 B2 | 6/2004 | King | |
| 6,819,956 B2 * | 11/2004 | DiLorenzo | 607/45 |
| 6,853,863 B2 | 2/2005 | Carter | |
| 6,858,000 B1 | 2/2005 | Schukin et al. | |
| 6,871,099 B1 | 3/2005 | Whitehurst et al. | |

(Continued)

OTHER PUBLICATIONS

C. Magarinos-Ascone, et al., High-Frequency Stimulation of the Subthalamic Nucleus Silences Subthalamic Neurons: A Possible Cellular Mechanism in Parkinson's Disease, Neuroscience, 2002, 1109-17, 115(4).

(Continued)

*Primary Examiner* — Brian Szmal
*Assistant Examiner* — Fangemonique Smith
(74) *Attorney, Agent, or Firm* — Reising Ethington P.C.

(57) ABSTRACT

A tissue stimulation system that generates an electrical tissue stimulation signal configured to reduce tissue impedance and increase depth of signal penetration. The use of leads is dynamically controlled and altered between conducting biopotential voltages, conducting electrical tissue stimulation signals, and grounding, in response to a computational analysis of biopotential data acquired from a region of tissue to be stimulated.

76 Claims, 24 Drawing Sheets

U.S. PATENT DOCUMENTS

| | | | |
|---|---|---|---|
| 6,901,294 | B1 | 5/2005 | Whitehurst et al. |
| 6,922,590 | B1 | 7/2005 | Whitehurst et al. |
| 6,950,707 | B2 | 9/2005 | Whitehurst et al. |
| 7,013,177 | B1 | 3/2006 | Whitehurst et al. |
| 7,024,239 | B2 | 4/2006 | George et al. |
| 7,054,686 | B2 | 5/2006 | MacDonald |
| 7,076,307 | B2 | 7/2006 | Boveja et al. |
| 2002/0055675 | A1 | 5/2002 | Llinas et al. |
| 2002/0072782 | A1* | 6/2002 | Osorio et al. ............ 607/45 |
| 2003/0200114 | A1* | 10/2003 | Ogino et al. ............ 705/2 |
| 2003/0204148 | A1 | 10/2003 | Lange et al. |
| 2004/0092809 | A1 | 5/2004 | DeCharms |
| 2004/0267333 | A1 | 12/2004 | Kronberg |
| 2005/0277998 | A1 | 12/2005 | Tracey et al. |
| 2006/0004422 | A1 | 1/2006 | De Ridder |
| 2006/0074298 | A1 | 4/2006 | Borsook et al. |
| 2006/0149337 | A1 | 7/2006 | John |
| 2006/0217782 | A1* | 9/2006 | Boveja et al. ............ 607/45 |
| 2009/0030476 | A1 | 1/2009 | Hargrove |
| 2010/0324441 | A1 | 12/2010 | Hargrove et al. |

OTHER PUBLICATIONS

Prakash Kara et al., The Spatial Receptive Field of Thalamic Inputs to Single Cortical Simple Cells Revealed by the Interaction of Visual and Electrical Stimulation, Proceedings of the National Academy of Sciences, Department of Neurobiology, Harvard Medical School, 2002, 16261-16266, vol. 99, No. 25.

Steven Weinstein, The Anticonvulsant Effect of Electrical Fields, Current Neurology and Neuroscience Reports, 2001.

V. Tronnier, Electrical Stimulation of the Motor Cortex in Neuropathic Pain, 2001, 278-279, 15(4).

Marcos Velasco et al., Centromedian-Thalamic and Hippocampal Electrical Stimulation for the Control of Intractable Epileptic Seizures, 2001, Journal of Clinical Neurophysiology, 495-513, 18(6).

* cited by examiner

METHODS AND APPARATUS FOR ELECTRICAL STIMULATION OF TISSUES USING SIGNALS THAT MINIMIZE THE EFFECTS OF TISSUE IMPEDANCE

CROSS-REFERENCES TO RELATED APPLICATIONS

This application is a Continuation-in-Part of U.S. patent application Ser. No. 11/490,255 which is a continuation of U.S. patent application Ser. No. 10/357,503 which claims priority in an earlier filed provisional application U.S. Ser. No. 60/353,234, filed on Feb. 4, 2002; this application also claims priority in and incorporates by reference U.S. Provisional Patent Application Ser. No. 60/963,486 filed 6 Aug. 2007, U.S. Provisional Patent Application Ser. No. 61/014,917 filed 19 Dec. 2007, and U.S. Provisional Patent Application Ser. No. 61/024,641 filed 30 Jan. 2008, and U.S. Provisional Patent Application Ser. No. 61/032,241 filed 28 Feb. 2008.

BACKGROUND OF THE INVENTION

1. Field of the Invention

The present invention relates generally to the field of producing and applying electrical energy to tissues for the purpose of stimulating such tissues, and to therapeutic methods and apparatus. More specifically, the present invention relates to a system for providing and using electrical signals having characteristics that allow them to minimize electrical impedance of tissues, and more specifically yet, to various methods and apparatus for providing such signals for the purpose of providing therapeutic benefit to a living being.

2. Description of Related Art

A number of examples of recent patents may be used to understand the background of the present invention, as well as some of the limitations it overcomes. For example, Boveja, et al. in U.S. Pat. No. 7,076,307 disclose a method for pulsed electrical stimulation of the vagus nerve as a means of providing therapy for a number of neurological disorders. As another example, Whitehurst, et al., disclose in several patents (U.S. Pat. No. 7,013,177; U.S. Pat. No. 6,950,707; U.S. Pat. No. 6,922,590; U.S. Pat. No. 6,901,294; and U.S. Pat. No. 6,871,099) methods for treating a number of disorders involving the application of electrical stimulation to the brain and/or the spinal cord. In these patents, the method of delivery for the electrical stimulation signal involves surgically implanting some device within the tissues. The disclosure of King in U.S. Pat. No. 6,745,079 is yet another example of teachings involving implantation for electrical stimulation. However, King teaches the use of implantable electrodes associated with an external device.

More general examples of patents exist that describe the benefit of electrical stimulation of tissues. These examples include the teachings of Carter (U.S. Pat. No. 6,853,863) and Borkan (U.S. Pat. No. 6,662,053). In U.S. Pat. No. 7,054,686, MacDonald discloses a process for stimulating tissue, such as cardiac tissue, nerve tissue, and brain tissue, by delivering a sequence of individual pulses. George, et al., disclose in U.S. Pat. No. 7,024,239 a method of using electromagnetic energy as a form of tissue stimulation for the purposes of treating chronic wounds. Similar teachings exist for the use of electrical stimulation in speeding the healing process of wounds, and in particular, to the repair process of injured bones (U.S. Pat. No. 6,858,000 by Schukin, et al. and U.S. Pat. No. 6,678, 562 by Tepper, et al.).

Among other things, none of these patents discloses any consideration of the electrical nature of the tissues themselves, either at the macro level or at the basic cellular level, or of how tissue stimulation signals might be adapted to take into account that electrical nature. At the macro level, a reduction of the fundamental impedance of tissues will have the effect of providing for increased conductance and hence deeper penetration of an applied electrical signal or field into said tissues. At the cellular level, impedance changes similarly affect conductance, and also in the case of neural cells, probably affect electrical properties such as nerve conduction velocity and neuron firing rates. As with all materials that have the ability to conduct electricity, the impedance of tissues involves components of both resistance and reactance. Generally speaking, tissue is a relatively poor conductor of electricity due to high resistance values. However, tissues also have a capacitive nature that provides for a form of impedance formally known as capacitive reactance.

Capacitive reactance decreases as the frequency of an electrical signal increases. This principle is the basis for the general knowledge that an ideal capacitor will completely block a zero-frequency signal (also known as a "DC" signal) since the capacitor's capacitive reactance will be infinite. Similarly, the same capacitor will pose very little impedance to a signal of very high frequency. Considering the capacitive nature of tissues, higher frequency signals are more readily conducted through them.

However, for the purposes of affecting tissues in a therapeutic way, lower frequency signals are relevant. Thus, a paradox exists in the pursuit of the use of electricity for therapeutic purposes in that, while the low frequency signals are useful for affecting tissues and biochemicals, they are also most severely attenuated by tissue impedance.

The patents discussed above generally attempt to overcome this by using implantable devices that place the source of the electrical stimulating energy in close proximity to the tissues meant to be stimulated, or by providing stimulating electricity at levels that are sufficiently high to allow for attenuation and still accomplish an effect. In the latter case, the comfort of the subject receiving the stimulation electricity is frequently compromised during therapy.

SUMMARY OF THE INVENTION

A tissue stimulation apparatus is provided comprising an electrical stimulation device 1 that includes a stimulation signal generation circuit configured to generate an electrical tissue stimulation signal that reduces tissue impedance and increases depth of signal penetration.

Also, a tissue stimulation method is provided, which comprises the steps of providing a tissue stimulation apparatus configured to dynamically alter the use of leads between conducting biopotential voltages, conducting an electrical signal for stimulating tissues, and grounding, in response to a computational analysis of biopotential data acquired from a region of tissue to be stimulated; acquiring biopotential data from a region of tissue to be stimulated; performing a computational analysis of the acquired biopotential data; in response to the analysis, identifying and placing sufficient leads so as to provide a number of possible conduction paths passing in near proximity to a region of tissue of interest; and dynamically controlling electrical signal delivery to the region of tissue of interest by selectively switching the use of the leads as conductors and grounds.

A further tissue stimulation method is provided, which includes the steps of determining parametric values of an electrical tissue stimulation signal by obtaining biopotential voltage data from a region of tissue to be stimulated, and determining parametric values of an electrical tissue stimulation signal in response to the biopotential voltage data; and generating and applying to the region of tissue an electrical stimulation signal having the determined parametric values.

Another tissue stimulation method is provided, which includes the steps of determining parametric values of an electrical tissue stimulation signal by taking measures of electrical properties of a region of tissue to be stimulated, making statistical comparisons between the measures and measures known to represent normal tissue electrical properties in a healthy normal population of living beings, determining parametric values of an electrical tissue stimulation signal in response to the comparisons, and generating and applying to the region of tissue an electrical stimulation signal having the determined parametric values.

Another tissue stimulation method is provided, which includes the steps of determining parametric values of an electrical tissue stimulation signal by taking measures of biochemicals from tissues and/or fluids relevant to the tissues to be stimulated, analyzing the measures, and determining parametric values of an electrical tissue stimulation signal in accordance with the analysis of the measures. An electrical stimulation signal having the determined parametric values and configured to reduce tissue impedance and increase depth of signal penetration is generated and applied to the region of tissue.

Also provided is a method of directing electrical stimulation signals through desired tissue regions. This method includes the steps of placing at least one stimulating lead 21 in proximity to the or each desired tissue region, placing at least one ground lead 20 in another proximity to the or each desired tissue region such that a vector path extends between the or each stimulating lead and the or each ground lead and passes through the or each desired tissue region, and introducing an electrical stimulation signal through the at least one stimulating lead such that current is caused to flow along the or each vector path through the or each tissue region between the or each stimulating lead and the or each ground lead.

Also provided is a tissue stimulation method that includes the steps of determining parametric values of an electrical tissue stimulation signal by taking measures of electrical properties of a subject, transmitting the measures to a remote location via a network, analyzing the measures at the remote location, remotely determining parametric values of an electrical tissue stimulation signal in response to the analysis, transmitting the parametric values from the remote location via a network to an electrical stimulation apparatus, and causing the electrical stimulation apparatus to generate and apply to the region of tissue an electrical stimulation signal having the remotely determined parametric values.

Also provided is a method for treatment of conditions using electrical tissue stimulation signals, which includes the steps of measuring biophysical activity in a portion of a subject's body to be treated, analyzing the measured biophysical activity, determining the or each site to which electrical stimulation will be applied, determining electrical parameters for the electrical signal to be applied to the subject, which will tend to bring the subject's biophysical values for the determined site to more normal, desired values, placing at least one stimulating lead in proximity to the or each determined site, placing the or each ground lead so as to create a vector direction between the or each stimulating lead and the or each ground lead that will cause at least one path of electrical stimulation to pass through the or each determined site, and applying through the leads an electrical signal having the determined parameters.

Also provided is a method for treating conditions associated with central nervous system dysfunction. This method includes applying an electrical tissue stimulation signal to a subject suffering from one or more conditions selected from the group of conditions consisting of fibromyalgia syndrome, chronic pain, traumatic brain injury, affective disorders, such as attention deficit disorder (ADD) and attention deficit hyperactivity disorder (ADHD), chronic fatigue, sleep disorders, obsessive compulsive disorder, Tourette Syndrome, depression, anxiety, and addiction.

Also provided is a method for treating conditions associated with abnormal levels of biochemicals in tissues. This method includes applying an electrical tissue stimulation signal to a subject suffering from one or more conditions selected from the group of conditions consisting of fibromyalgia syndrome, chronic fatigue, obesity, chronic pain, muscle pain, myofascial pain, myofascial trigger points, and psychological conditions, such as depression.

Also provided is a method for enhancing a body's own healing mechanisms. This method includes applying an electrical tissue stimulation signal to a subject suffering from one or more conditions selected from the group of conditions consisting of broken bones, injured tissues, post-surgical wounds, cuts, muscle pain associated with strains, and spasms.

Also provided is a method for improving a body's function. This method includes applying an electrical tissue stimulation signal to a subject, the signal configured and applied in such a way as to produce one or more effects selected from the group of effects consisting of reducing fatigue, increasing alertness, and increasing mental clarity.

Also provided is a method for enhancing performance measures of a subject. This method includes applying an electrical stimulation signal to a subject, the signal configured and applied in such a way as to enhance performance measures associated with one or more endeavors selected from the group of endeavors consisting of athletic and academic endeavors.

Also provided is a method for enhancing organ function in a subject. This method includes applying an electrical stimulation signal to a subject, the signal configured and applied in such a way as to advantageously enhancing the function of an organ.

Additional advantages and novel features of the invention will be set forth in part in the description that follows, and in part will become more apparent to those skilled in the art upon examination of the following or upon learning by practice of the invention.

BRIEF DESCRIPTION OF THE DRAWINGS

For a more complete understanding of the present invention, the needs satisfied thereby, and the features, and advantages thereof, reference now is made to the following description taken in connection with the accompanying drawings.

DETAILED DESCRIPTION

Figure 1:
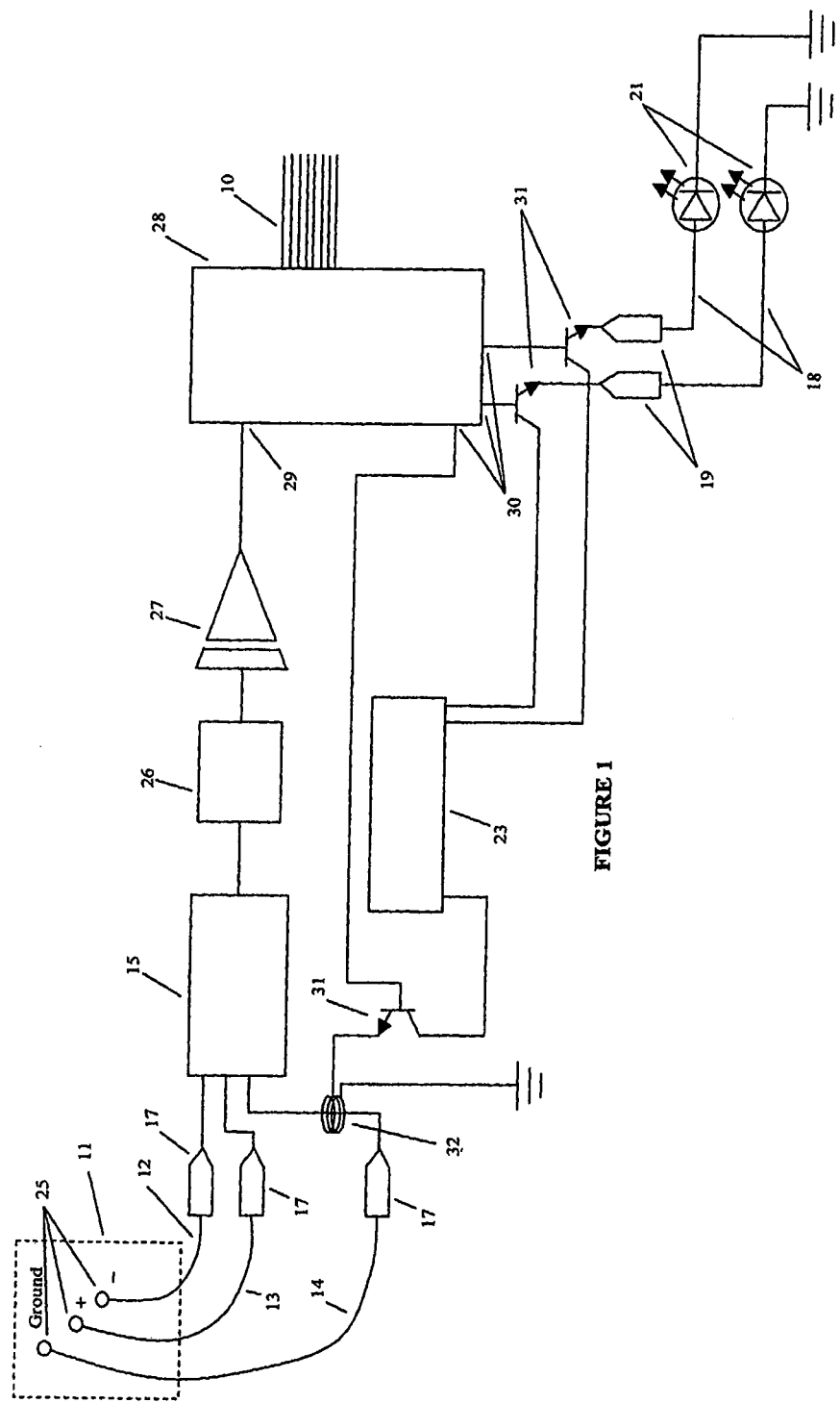
FIG. 1 shows an apparatus constructed according to the invention.

The present invention is directed towards a method and an apparatus suitable for the treatment of neurological dysfunctions.

The term "optical unit" is intended to define an apparatus that is used on or in close proximity to the eyes. By close proximity, it is meant a distance from the eyes of a subject that is effective for the transmittal of a light pulse into the eyes of the subject. Preferably, close proximity will not exceed one foot in distance from the subject. The structure of the optical unit may be worn on the face of the patient, such as optical device or goggles, or it may be located in a separate structure, such as a stand that is held near the face or even a hand-held mask. Further, the optic unit may be placed at an angle to the eyes of the subject. Additionally, the optic unit may be positioned behind the subject and use mirrors or other reflective devices (such as a white wall) to reflect the light pulse into the eyes of the subject. However, in no way is this definition intended to limit the ultimate structure the optical unit may take.

The term "neurological dysfunction" is intended to define a group of disorders in which one or more regions of a subject's brain operate at frequencies which are different from the predetermined frequency for that region of the brain or from the predetermined frequencies of the other regions of the subject's brain. Examples of neurological dysfunctions include traumatic brain injury, post traumatic stress disorder, post stroke paralysis, post traumatic brain injury paralysis, cerebral palsy, headache, depression, post chemotherapy cognitive, mood and fatigue disorder, fibromyalgia, memory loss, coma, attention deficit disorder, etc. However, the present invention is not to be construed as being limited to the treatment of these listed examples.

The term "irregular activity" is intended to define the EEG frequency of an region of the subject's brain which does not match the predetermined EEG activity of the remaining regions of the subject's brain. Additionally, the term "irregular activity" is also intended to define an EEG frequency of an region of the subject's brain that matches the EEG activity of the remaining regions of the subject's brain, but with a high degree of variance. Irregular activity is determined by analyzing the frequency bands of the region of the brain being investigated and identifying either a higher band amplitude or a lower band amplitude than is predetermined for that region. Examples of potential irregular activity include amplitude abnormalities in which the measured peak-to-peak microvolts is over 14 microvolts (abnormally high) or in which the measured microvolts is under 5 volts from peak-to-peak (abnormally low) or possesses a standard deviation of over 3 microvolts. However, these are examples only. One of ordinary skill would recognize what a proper benchmark would be for each subject.

The term "neurostimulation signal" is intended to define a signal transmitted by the neurostimulator to a subject for the purpose of normalizing the brainwave activity of regions of the subject's brain that possess irregular activity. The neurostimulation signal is determined on a subject by subject basis and is changed in relation to a shift in the region's dominant frequency. There is typically a reduction in variability as EEG changes occur. This is evidenced by a shift in the dominant frequency more towards the typical frequencies and amplitudes that were predetermined for that region of the subject's brain.

The term "normalization" is intended to define the result of the administration of a neurostimulation signal to regions of the subject's brain that correspond to the regions of the subject's brain that possess irregular activity. The neurostimulation signal is intended to "normalize" or adjust the brainwave frequency of the regions of the subject's brain that possess irregular activity to reflect the predetermined frequency of the region of the subject's brain that is being treated.

The term "dominant frequency" is intended to define the frequency in the EEG measurements taken from an area of the subject's brain that possesses the highest voltage amplitude.

The present invention is directed towards the alleviation of symptoms of neurological disorders caused by irregular EEG activity in a subject's brain. The alleviation of the symptoms is accomplished by administering a neurostimulation signal to the regions of the subject's brain that are related to those regions of the subject's brain that possess irregular activity. These related regions of the subject's brain can include regions that possess irregular activity, or other regions of the brain. One of skill in the neurological arts would recognize which regions of the brain are interrelated with other regions of the brain.

For example, in one method of choosing the treatment sites, the choice is determined by the regions of EEG-slowing specific to an individual, regardless of the diagnosis. In this method, it is the presence and pattern of EEG-slowing at any of the standard neurological 10-20 sites (as selected by the International 10-20 EEG Site Placement Standard) that is the indication of the appropriateness of a region of the brain for treatment. The EEG-slowing pattern also determines where on the scalp electrodes will be placed for treatment.

Because EEG slowing that is associated with fatigue, poor short-term memory, and attention problems is likely to involve functional deficits in the left frontal lobes of the brains, placing electrodes on any of the following sites is a reasonable directive: FP1, F7, F3, C3, F1, AF7, F5, AF3 and possibly temporal sites, T3 & T5 (according to the International 10-20 EEG Site Placement Standard). The amplitudes and standard deviations from the image data determine the order of treatment for these sites.

The imaging data is preferably gathered by sequentially recording from each of 21 sites. These data are preferably processed through a Fast Fourier Transform (FFT) computation which produces quantitative data that shows the average microvolts and the standard deviation for each frequency component of the EEG signal at each site. A preferred method of treatment is to identify those sites that have the highest standard deviation as shown in the FFT results and treat them first. Treatment can be accomplished by placing two pairs of electrodes (one positive and one negative comprise a pair) on each of the four sites having the highest measured amplitudes.

It is the unique EEG pattern of the individual, however, that is the key to the most efficient treatment. The determination of treatment sites applies to any diagnostic category of neurological dysfunction and the determination is individualized by the quantitative data from each individual's brainwave data. Therefore, it is not possible to specify a standard set of sites for any given, or all, diagnostic categories. However, there is a broad diagnostic classification called EEG-slowing and that this category can permit the selection of predetermined sites from which to direct the treatment of choice. Therefore, given the above information one of ordinary skill would understand how to select a region of the brain for treatment on a subject by subject basis.

The neurostimulation signal is administered by modulating a high frequency component, which can be further pulse-width modulated for control of the energy level, with a low frequency carrier. It is the preferred intent of the present invention to "disentrain" the brain's electrical activity, that is, to not target or lock into a particular frequency, but rather to redistribute existing energy to all frequencies in the normal spectra of the brain EEG in a typically uniform manner. However, the present invention does not preclude the utilization of the neurostimulation signal for the purposes of entrainment.

The present invention also embodies a method of focusing a neurostimulation signal directly on a suspected dysfunctional region of the brain. This is possible because tissue impedances are minimized by the design of the neurostimulation signal. The neurostimulation signal possesses a greater ability to directly reach damaged regions of the brain rather than simply following the outer-most tissues around the scalp and thereby bypassing the damaged region of the brain. Another advantage is achieved by inducing the neurostimulation signal directly into EEG sensors. This advantage is that the neurostimulation signal can be strategically placed to present a conduction path through the damaged region of the brain, while concurrently measuring the EEG signal at the dysfunctional regions, thus providing a direct link between the measured EEG signals and the neurostimulation signals being delivered directly to the dysfunctional region.

A method for treating a subject with the method of the present invention preferably includes the generation of an electrical neurostimulation signal characterized by a high frequency pulse train modulated by a low frequency carrier signal. A means of providing for variable levels of electrical power may be accomplished by using either pulse width modulation of the high frequency pulse train, as in the preferred embodiment of the present invention, or variable amplitudes of the same pulses. Preferably, the frequency of the high frequency pulse train is at least one order of magnitude greater than the frequency of the low frequency carrier signal. It is preferred that the high frequency pulse be in the range of 43 to 1,000,000 hertz. It is more preferred that the high frequency pulse be in the range of 1,000 to 100,000 hertz. It is even more preferred that the high frequency pulse be in the range of 10,000 to 20,000 hertz. It is most preferred that the high frequency pulse be 15,000 hertz.

The low frequency carrier signal is variably related to critical frequency components of the EEG power spectral density, determined from statistical analysis of amplitudes and variability. The low frequency carrier signal is determined from information obtained by measuring EEG activity at a reference site or sites that generally corresponds with the location of suspected brain dysfunction, and the low frequency carrier signal is dynamically changed as a function of time to prevent entrainment. This is performed by changing the frequency offset (as described below) at predetermined time intervals. It is preferred that the low frequency carrier signal be typical of a brainwave EEG. It is more preferred that the low frequency carrier signal be in the range of 1-42 hertz.

The combination of (1) the high frequency pulse train as it is modulated by (2) the low frequency carrier signal, henceforth referred to as an AMPWM signal, provides a means of minimizing the effect of tissue impedances of the head. However, no limitation of the present invention to AMPWM signals alone is intended by this abbreviation. Any signal that possess both (1) and (2) as defined above is intended to be encompassed by the present invention.

In general, as will be discussed in greater detail in subsequent sections of this disclosure, the electrical impedance of tissues of the head decreases with increased electrical signal frequency. Thus, the high frequency pulse train component of the AMPWM signal passes through the head tissues with less attenuation than the low frequency carrier signals typically used in already known neurostimulation methods. Further, the low frequency carrier signal component of the neurostimulation signal in essence serves to turn on and off the high frequency signal component with a frequency that is generally related to the range of frequencies present in an EEG signal. Thus, the low frequency carrier signal component may be produced at frequencies commonly used for therapeutic purposes in neurostimulation devices, such as entrainment or disentrainment.

Some neurological dysfunctions that may be treated by the present invention include traumatic brain injury, post traumatic stress disorder, post stroke paralysis, post traumatic brain injury paralysis, cerebral palsy, headache, depression, post chemotherapy cognitive, mood and fatigue disorder, fibromyalgia, memory loss, coma, attention deficit disorder, etc. However, this list is not intended to be exclusive.

The method preferably comprises taking a first measurement of the EEG of a subject afflicted with at least one type of the neurological dysfunction in order to obtain EEG results and evaluating the obtained EEG results to determine whether any region of the subject's brain possesses irregular activity as compared to other regions of the subject's brain. It is preferred that the subject be a mammal and, more preferably, a primate. It is most preferred that the subject be a human being. It is also preferred that the irregular activity be determined by comparing the EEG signals from a region of the subject's brain with the EEG signals from the remaining regions of the subject's brain. It is also preferred that the EEG signals are obtained from more than one region of the subject's scalp. It is even more preferred that the EEG signals be obtained from at least 21 regions of the subject's scalp that correspond to 21 regions of the subject's brain. It is preferred that the regions be selected according to the International 10-20 EEG Site Placement Standard.

A determination of a dominant frequency of the subject's brain is made from the evaluating the EEG results from the regions of the subject's brain that possess irregular activity. Preferably, the evaluation involves the correlation of the EEG signals into a graphic image of the subject's brain. Even more preferably, the graphic image is evaluated and new EEG signals from the subject's brain are taken in order to ensure that the first EEG signals were accurate and in order to determine a dominant frequency from the regions of the subject's brain that have been confirmed as possessing irregular activity.

Finally, the method comprises an administration of an antineurological dysfunction therapy to the subject. The antineurological dysfunction therapy comprises inducing a neurostimulation signal directed to the regions of the subject's brain that possess irregular activity for a time sufficient to normalize the EEG signals of the regions of the subject's brain that possess irregular activity.

It is preferred that the time be between one second and one hour. It is more preferred that the time be between 1 and 30 minutes. It is even more preferred that the time is between 1 minute and 10 minutes. It is even more preferred still that the time be between 1 minute and 3 minutes. It is still more preferred that the time be between 1 second and 30 seconds. It is most preferred that the time be between 1 second and five seconds.

Additionally, further EEG signal measurements from the regions of the subject's brain that possess irregular activity are monitored during the administration of the therapy and the neurostimulation signal is adjusted based on any detected changes in the additional EEG signal measurements. The normalization of the EEG signals from the regions of the subject's brain that possess irregular activity results in an alleviation of the symptoms of the neurological disorders.

The neurostimulation signal comprises a carrier frequency which comprises the dominant frequency and the frequency offset. It is preferred that the frequency offset be between −10 and 20 hertz.

It is preferred that the normalization of the regions of the subject's brain that possess irregular activity result in these regions transmitting EEG signals which are close to the predetermined frequency and amplitude expected for those regions of the subject's brain. It is even more preferred that these regions transmit EEG signals at the predetermined frequency and amplitude expected for those regions of the subject's brain after the treatment.

The subject may require multiple exposures to the method in order to achieve an alleviation of the symptoms he or she suffers from the neurological dysfunctions. It is preferred that the multiple exposures remain in the range of 1 to 40 exposures. However, more exposures are permitted, if required. It is more preferred that the exposures remain in the range of 10 to 30 exposures. It is more preferred that the exposures remain in the range of 5 to 10 exposures. Additionally, it is preferred that a repeated use of the method be avoided within 24 hours of a previous use of the method. However, if required, it is possible to treat more than one region of the subject's brain (if more than one region of the subject's brain possesses irregular activity) in one treatment session.

Additionally, the subject may be medicated, sedated, or unconscious during the administration of the method. However, it is preferred that the subject be in none of these conditions.

Regarding the application of the neurostimulation signal itself, after the identification of regions the subject's brain which possess irregular activity, neurostimulation treatment is accomplished by placing EEG sensors in an arrangement that allows for the measurement of the EEG activity from the dysfunctional region, as well for providing a successful delivery of current from the EEG sensors into a system ground. The computer-controlled system in the preferred embodiment of the present invention acquires EEG signal data from the sensor sites and conducts an analysis of the EEG signal data to determine the frequency of the low frequency carrier signal component of the AMPWM signal.

The AMPWM signal can be transmitted to the subject through a plurality of neurostimulation delivery modes. In a preferred embodiment of the present invention the preferred mechanism of delivery is accomplished by inducing the AMPWM signal into the EEG sensors through inductive coupling. Another preferred mechanism is to use the AMPWM signal to drive a light-generating component, such as a light emitting diode, to provide a photic stimulation signal that may be delivered to the patient through the optic nerve.

Another preferred embodiment involves the simultaneous use of stimulation delivery by inducing the AMPWM signal into the EEG sensors through inductive coupling and drive a light-generating component, such as a light emitting diode, to provide a photic stimulation signal. In essence, this is a combination of previously discussed embodiments.

Lastly, it is preferred that EEG leads be placed on the scalp regardless of what stimulation method is used because the apparatus and method preferably measures EEG during stimulation delivery, and uses these EEG measurements to drive neurostimulation signal parameters.

In a preferred embodiment of the present invention, delivery mode is selectable to account for different levels of sensitivity and tolerance in patients. It is also possible to completely automate the process of transmitting the neurostimulation signal and the monitoring of the EEG signal data from the EEG sensors.

As stated above, it is preferred that the EEG signals from the subject be measured at typically 21 different scalp locations and it is preferred that power spectral density computations are performed on the obtained EEG signals. These computations break the measured analog EEG signals into frequency domain data such as a Fourier series of discrete frequency components, which is limited to 1-42 Hertz (greater signal components exist and could be utilized, but the 1-42 Hertz range is typically considered clinically useful). However, other methods of obtaining the frequency domain data are acceptable (such as the use of wavelet analysis).

In analyzing EEG signal data, frequency bands are commonly used. For example, the "delta" band is typically 1-4 Hertz, the "theta" band is 5-7 Hertz, and so on. For each site, the total amplitude associated with each discrete frequency component is assigned to proper bands, providing a measure of the EEG band energy for each of the aforementioned sites. From this, a graphic "image" is generated where colors represent amplitudes. From this image, the clinician can see EEG band activity related to regions of the brain, and based on clinical knowledge, can determine if a region has unusual or abnormal activity.

Accordingly, the neurostimulation phase of the process (i.e. treatment) is administered to correct regions of abnormal activity. The administration of the neurostimulation signal is preferably performed after the imaging process described above is completed. The clinician preferably applies EEG sensors to regions of the scalp that relate to the regions of suspected dysfunction and the EEG signal data is preferably re-measured for a period long enough to provide power spectral density data (as in the imaging process). The frequency domain data is then sorted, and the frequency that exhibits the highest amplitude is designated the "dominant frequency". According to clinician chosen stimulation time and frequency parameters, a neurostimulation signal is generated that has a "carrier frequency" that is determined by the formula: CARRIER FREQUENCY=DOMINANT FREQUENCY+FREQUENCY OFFSET.

The parameters the clinician uses are (1) stimulation intensity, (2) the times that the stimulation signal is turned on in the treatment cycle (as well as the number of times), (3) the duration that each stimulation signal is turned on, the leading frequency of each stimulation event, and (4) the phase offset of each stimulation event. Intensity is defined by the pulse-width-modulation duty cycle, and ranges from 0 (no "on-time") to 100% (no "off-time"). Thus, an intensity of 50% would have a duty cycle such that "on-time" is equal to "off-time" in each pulse cycle. The number of stimulation cycles and the times that the stimulation turns on is entirely clinician driven. However, it is preferred ranges that the stimulation cycles range between 1 stimulation event up to 50. It is preferred, however, that no more than 20 different stimulation events be used per session. The preferred leading frequency is already defined to range between −10 and 20 Hz. Preferred Phase offset ranges from −180 to 180 Hz.

In this formula, "frequency offset" is preferably selected from the range of −40 to 40 Hertz and more preferably from −10 and 20 Hertz.

The offset is chosen by clinical experience, therefore, one of ordinary skill in the art would recognize how to choose an offset. However, the clinician generally picks the largest offset (i.e., +20 Hz) to see if a response is elicited. If no response is elicited, lower offsets will be tried until a response is obtained. The clinician's choice of parameter values is typically driven by a selection of choices that cause the subject to react, but yet do not cause an "over-reaction" which is an adverse effect characterized by short-term fatigue, headache, etc All of the preferred neurostimulation parameters to be considered are defined below. Values of these parameters are chosen based on clinician experience, and are selected in a manner that is meant to cause a reactive therapeutic effect without causing the subject to over-react. The selection of these values is further driven by subject condition and symptomatic presentation. For example, a subject with mild traumatic brain injury may be able tolerate a longer (in duration) than average stimulation application without suffering an adverse effect. However, a subject with fibromyalgia with severe fatigue may only tolerate a very short (in duration) stimulation burst at the lowest intensities possible. The ranges of values for these parameters are provided for the clinician to choose based on experience, patient condition and symptomatic presentation, thus no preferred or optimal values exist. These parameters include:

Intensity—This is a measure of the pulse width modulation signal's duty cycle. This provides a variation on the time-averaged current delivered to the stimulation mechanisms (i.e. the EEG lead inducing circuit and the photic stimulators).

Duration—This is a measure the time in seconds that a neurostimulation event (i.e. a period of stimulation signal output) lasts. This can range from 1 second to 1,200 seconds in the preferred embodiment.

Start Time—This is the time in seconds after the beginning of a neurostimulation treatment session begins when a neurostimulation event starts to occur. There is no specific limitation on this, that is, the start time could begin at any time after the treatment session begins. Before the start time occurs, the system is simply measuring EEG and this could, theoretically, go on indefinitely.

Leading Frequency and Phase Offset are previously defined.

By adding the frequency offset to the dominant frequency, a carrier frequency is created that is always different than the dominant frequency. This neurostimulation signal is then either induced in the EEG sensors attached to the subject's scalp or the neurostimulation signal is used to drive light emitting diodes for photic stimulation purposes. The duration of the signal, along with other parameters (as described above) such as intensity and phase offset (in the case of LEDs for photic stimulation—a phase offset causes the LEDs to flash out of synchronization with each other) are determined by the clinician's chosen treatment protocol.

Figure 2:
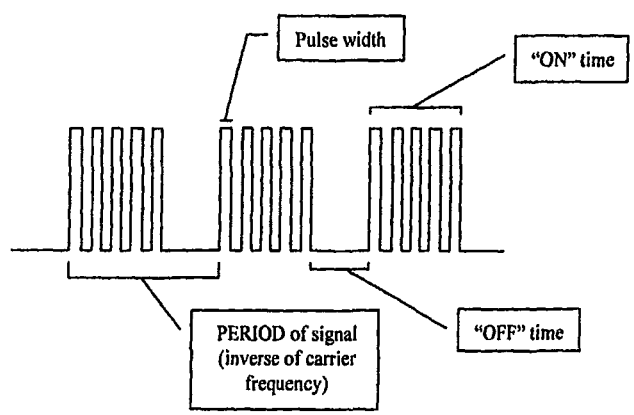
FIG. 2 shows a graphic representation of the neurostimulation signal.

As described above, the neurostimulation signal can be an amplitude modulated pulse-width modulation signal. A graphic representation of the signal is shown in FIG. 2. In other words, the carrier frequency simply turns an electric signal on and off in a way that a square-wave pulse train is generated with a frequency equal to the carrier frequency. Thus, in a period (period=1/frequency) of this pulse train, there will be an amount of time that the electric signal is "on" and an amount of time when the signal is "off" (see FIG. 2). During the time that the carrier signal is "on", the electricity is further pulsed at a very high frequency. A pulse width modulator is used to control this high frequency pulsing. By varying the pulse width, the average current applied is varied. This is what varying the "intensity" means. With a very low duty cycle, there is very little average current and thus the neurostimulation signal has very low intensity. Conversely, a higher duty cycle delivers more current and thus the intensity increases. A 100% duty cycle means that there is no "high frequency off time", and thus the entire neurostimulation signal is a simple square wave pulse train with frequency equal to the carrier frequency.

Figure 3:
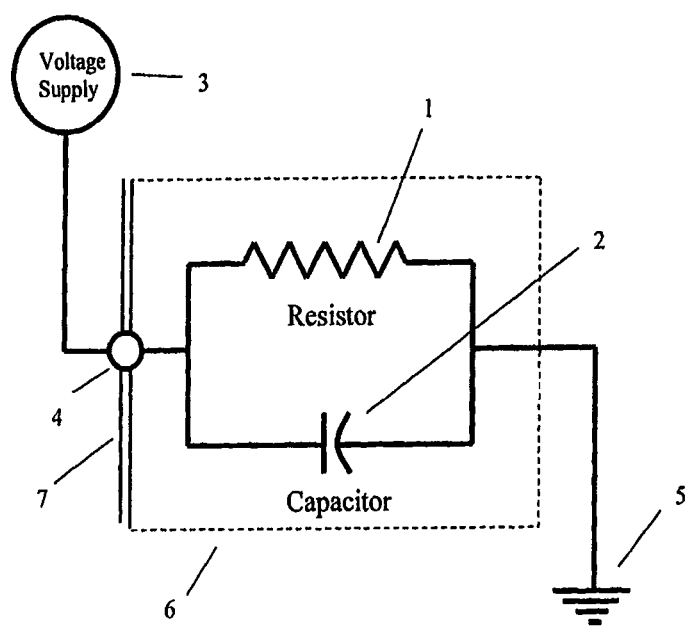
FIG. 3 shows a model of the apparatus of FIG. 1 in regards to tissue impedance.
Figure 4:
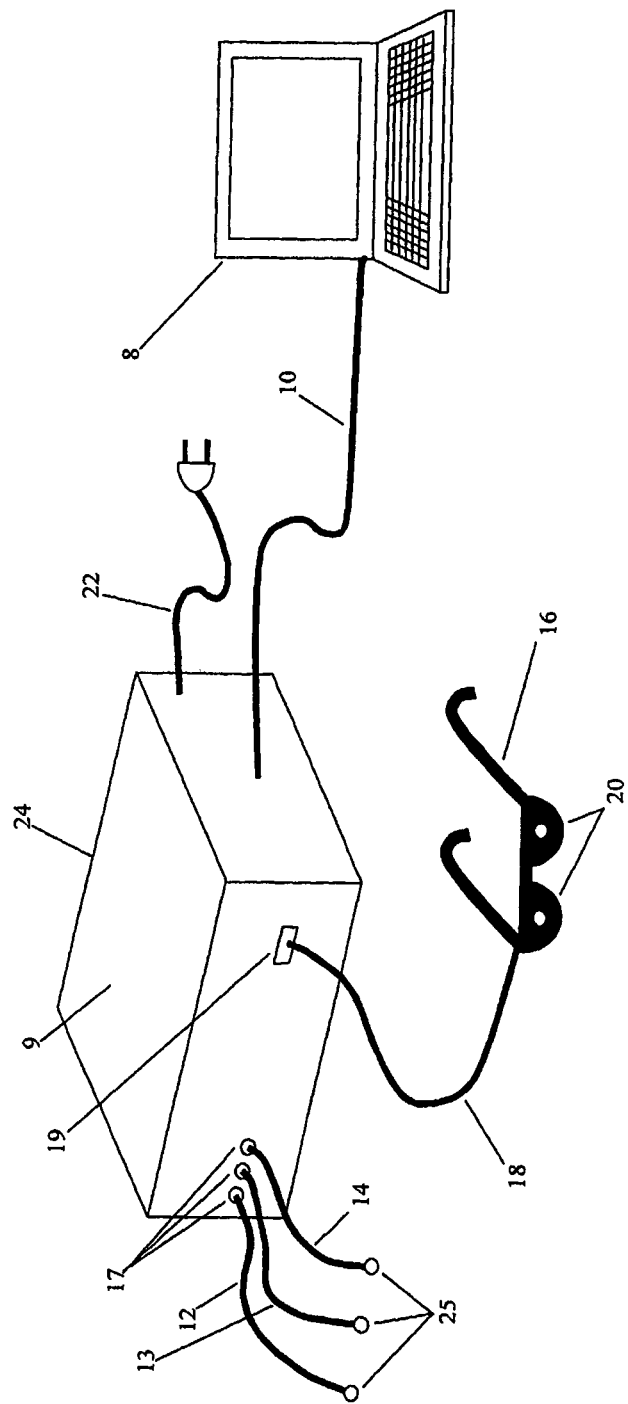
FIG. 4 shows another view of the apparatus of FIG. 1.

Regarding the apparatus, FIG. 3 presents a model of the apparatus of the present invention. In FIG. 3, tissue impedance 6 is represented by a parallel combination of a simple resistor 1 and a simple capacitor 2. A voltage source 3 provides electricity at a supply electrode 4 interfaced at a subject's skin 7, with the electricity passing through the tissue impedance 6 and ultimately being returned to a common ground 5 potential. Following fundamental circuit analysis, the equivalent impedance ($Z_{EQUIVALENT}$) of the circuit is given by the formula:

$$Z_{EQUIVALENT} = \frac{R}{1 + 2\pi fRC}$$

In this formula, the resistance is given by the nomenclature R, capacitance by C and frequency by f. This equation clearly shows that as the frequency of the signal increases, the overall impedance of the system decreases despite the level of impedance from the resistor 1 being constant. Although the impedances of the composite tissues of the head are considerably more complex and require a far more sophisticated model to accurately describe current flows, this model provides a simple analogy and approximately describes the effect, and is a fundamental basis for the disclosure of the present invention.

The effects of applying electrical energy to brain tissues, the electrical energy is known in this disclosure as a neurostimulation signal, are well established in the medical literature and in other teachings, and will not be expounded upon here.

As stated above, the invention is also directed to an apparatus for neurostimulating a subject. The apparatus comprises a computing device that is operatively coupled to a neurostimulator, and a series of EEG sensors that are coupled to the neurostimulator. Examples of appropriate computing devices are microprocessors or computers. However, any processing unit can be used in the present invention as a computing device. These components are coupled to each other via electrical conduction paths. For example, the neurostimulator could be coupled to the computing device with RS232 cable, USB cable, etc. Further, the EEG sensors can be coupled to the neurostimulator with an electrical connector. However, in both instances, other methods of coupling the components are acceptable. The EEG sensors are configured (1) to be attached to the subject, (2) to monitor EEG signals of a subject, and (3) to administer neurostimulation signals to the subject. Additionally, the EEG sensors comprise at least one positive contact, at least one negative contact, and at least one ground contact.

The apparatus further comprises a biopotential acquisition device, at least one filtering unit, an isolation amplifier, and a microcontroller. A preferred microcontroller is the Toshiba TMP95FY64. However, any comparable microcontroller may be used. The biopotential device is operatively coupled to the computing device, and the neurostimulator is configured to transmit the biopotential data and EEG signal data to the biopotential acquisition device. These components may be coupled together in the manner set forth previously or in any additional manner that permits their correct usage. Additionally, the biopotential acquisition device is configured to transmit the EEG data and biopotential data through at least one circuit or numerical filter and through an isolation amplifier which is operatively coupled to the microcontroller. Furthermore, it is preferred that the isolation amplifier be capable of performing "notch" filtering (i.e., eliminate 60 Hz line noise) and it can be selected from any component found on the market. It is preferred that it be a Burr-Brown ISO-100.

It is preferred that the filtering unit be selected from the group consisting of a circuit configured to filter data and a numerical filter. It is also preferred that the biopotential acquisition device is a biopotential amplifier or a high resolution analog-to-digital converter.

The neurostimulator comprises a biopotential acquisition unit comprising an electric circuit configured to acquire biopotential data from the EEG signals obtained by the EEG sensors attached to the subject. The biopotential acquisition unit is also configured to analyze and store the acquired biopotential and EEG data with computational means and it is operatively coupled to the neurostimulator. The neurostimulator also comprises a transmission unit configured to transmit the biopotential and EEG data from the neurostimulator to the computing device and an I/O (input/output) unit configured to adjust for a time lag in the biopotential and EEG data being transmitted. The neurostimulator also comprises at least one switching unit configured to manage a neurostimulation signal.

It is preferred that the subject is a mammal. It is further preferred that the subject be a primate and even more preferred that the subject is a human being. It is also preferred that the switching device is a transistor.

Additionally, the neurostimulator comprises an inductor, acting as a transformer, whereas the stimulation signal is induced in the neurostimulator by inducing electrical current into the inductor, which further induces electrical current in the EEG sensors via electromagnetic coupling, and thereby into the subject.

The neurostimulator can further comprise an optical unit which further comprises a set of light generating devices located in close proximity to the pupils of the subject. It is preferred that the light generating devices are light-emitting diodes.

With reference to the accompanying FIG. 1, a preferred embodiment of the present invention is described where a computing device 8 is operatively coupled to a peripheral device henceforth referred to as a neurostimulator 9, such as through a peripheral cable 10. However, a peripheral cable is not the only method of coupling the neurostimulator to the computing device. The neurostimulator 9 further comprises a series of electrical conductors henceforth referred to as EEG sensors 11. The EEG sensors 11 consist of at least one positive lead 12, one negative lead 13 and one ground lead 14. However, the at least one positive lead 12, one negative lead 13, and one ground lead 14 may also be incorporated into one sensor as contacts.

In a preferred embodiment of the present invention, employing multiple sets of EEG sensors II simultaneously and multiple biopotential acquisition devices 15 can accomplish acquisition of EEG signals from multiple sites on the scalp. For clarity, the preferred embodiment is described with for acquisition of EEG signal from one scalp site. All EEG sensors 11 are connected to the neurostimulator 9 via EEG sensor connectors 17.

The neurostimulator 9 can further comprise, as a possible means of delivering the stimulation signal, an optical unit 16 that is electrically coupled to the neurostimulator 9 via optical device sensors connectors 19. The optical unit 16 can be connected to the neurostimulator 9 by an optical device cable 18. However, other means of connecting the optical unit to the neurostimulator are acceptable. The optical device further comprises light generating devices 20 located to be in close proximity to the subject's eyes. In the preferred embodiment, the light generating devices 20 are light emitting diodes 21.

The neurostimulator 9 is operated by any number of possible power supply 22 sources. To assure electrical isolation for the patient's safety, an isolated power supply 23 is utilized in the preferred embodiment. Further, the neurostimulator 9 is housed in a protective outer enclosure 24.

The neurostimulator 9 preferably internally comprises the biopotential acquisition device and the biopotential acquisition device is preferably designed to acquire biopotential data from EEG signal data, specifically patient EEG, to provide a means for analysis and data storage of the biopotential data through computational means, generate a neurostimulation signal and deliver the neurostimulation signal to the patient. It is preferred that a Teledyne A110-2 amplifier be used.

In a preferred embodiment of the present invention, EEG signals are acquired with EEG sensors 11 attached to a patient's scalp. At the end of the EEG sensors 11 attached to the patient are contact electrodes 25. The EEG signal is delivered to the neurostimulator 9 via the EEG sensors 11, connected to the biopotential acquisition device 15 through EEG lead connectors 17 and operatively coupled to a biopotential acquisition device 15 such as a biopotential amplifier or high resolution analog-to-digital converter. To minimize the effect of external electrical noise, any number of circuit or numerical filters 26 may be employed in the preferred embodiment. To assure patient safety, the biopotentials are passed through an isolation amplifier 27. The output of the biopotentials, after passing through the biopotential acquisition device 15, filters 26 and isolation amplifier 27 is acquired by a microcontroller 28 through analog-to-digital ports 29. The microcontroller 28 is operatively coupled to the computing device 8. One method of coupling the microcontroller to the computing device is to use a peripheral cable 10. Control of the neurostimulator 9 is accomplished by communication between the microcontroller 28 and the computing device 8. Further, the objective of biopotential data analysis and storage is accomplished computationally via communication between the microcontroller 28 and the computing device 8.

After analysis of the acquired biopotential, that is, the EEG signal, the computing device 8 communicates proper stimulation signal parameters, in accordance with the present invention, to the microcontroller 28. These parameters include signal energy level, frequency of the low frequency component of an AMPWM signal, phase offset of multiple signals, start time, frequency offset and duration through a user interface. Utilizing a digital-to-analog port 30 on the microcontroller 28, the stimulation signal is output from the microcontroller 28 to transistors 31 or similar switching devices capable of managing the current levels of the stimulation signal. Depending on the mode of stimulation chosen by a clinician, the stimulation signal will be routed to the different means of stimulation signal delivery, alone or in combination. The parameters for the clinician's choice are set forth above.

If optical stimulation is desired, the stimulation signal will be sent to the optical unit 16 featuring the light generating devices 20 to be worn by the patient. Any unit capable of emitting light may be used as a light generating device. This includes, but is not limited to a LED, a light bulb, a low-power laser, etc. Alternately, if EEG lead 11 stimulation is desired, where the stimulation signal is delivered to the patient's scalp via the attached electrodes 25, then the stimulation signal is sent to an inductor 32 which is designed to induce current in the EEG sensors 11 from the stimulation signal generated by the microcontroller 28. In the preferred embodiment of the present invention, a plurality of stimulation delivery modes is warranted to allow for clinician choice to further effect successful treatment based on individual patient needs.

To assure patient safety, all electronics in the neurostimulator 9, including the biopotential acquisition device 15, the filter 26, the isolation amplifier 27, the microcontroller 28 and the transistors 31 are supplied electricity by the aforementioned isolation power supply 23.

Finally, regarding the coupling of the components, if a computing device is used it is preferably operatively coupled to the processor of the neurostimulator via any of a number of means of commonly used peripheral communications techniques, such as serial communication, USB port communication or parallel communication 10. All remaining electronics are preferably operatively coupled to the processing device (e.g. microcontroller) in the neurostimulator. The data acquisition circuit preferably comprises the biopotential acquisition device 15, filters 26 and isolation circuitry (amplifier) 27. The isolation amplifier is preferably coupled to an analog-to-digital input port on the microcontroller 28, via electrical conduction paths such as wires or printed circuit board conductors. The filters 26 are preferably operatively coupled to the isolation amplifier 27 via electrical conduction paths such as wires or printed circuit board conductors. Further, the biopotential acquisition device 15 is preferably operatively coupled to the filters 26 via electrical conduction paths such as wires or printed circuit board conductors.

EEG leads 11 are preferably coupled to the biopotential acquisition device 15 via electrical connectors 17, providing conduction of EEG electricity at the scalp to the biopotential amplifier 15.

A stimulation circuit is preferably coupled to a digital-to-analog port 30 on the microcontroller, in all cases via electrical conduction paths such as wires or printed circuit board conductors. It is preferred that an isolated power supply 23 supplies all operative power for neurostimulation outputs such as that to the optical device 16 or the EEG lead stimulation inducing circuitry 32. Electrical output from the digital-to-analog port 30 is preferably conducted to a transistor 31 that is further coupled to the isolated power supply 23. When a signal is received at the base of the transistor 31 from the microcontroller 28, the transistor operates to switch on electricity from the isolated power supply 23 which is further conducted via electrical coupling to the inductor (stimulation inducing circuitry) 32. Current flow in the inductor 32 induces a current in the EEG lead, as described in the specification.

Alternately, for photic stimulation, the isolated power supply 23 is preferably coupled via electrical coupling to two more transistors 31, which are preferably operatively coupled via electrical coupling to independent digital-to-analog ports 30 on the microcontroller 28. Electricity conducted from the digital-to-analog ports 30 to the base of the transistors 31 in the photic stimulation circuit has the effect of switching on these transistors, further allowing for conduction of electricity to the photic stimulation devices, such as LEDs 21. The photic stimulation devices are preferably coupled to the transistors 31 via electrical connectors 19, thus providing for current flow to the photic stimulation devices such as LEDs 21.

Finally, it is preferred that the apparatus operate on a 12 volt power supply. It is more preferred that the apparatus operate on a 6 volt power supply. It is most preferred that the apparatus operate on a power supply equivalent to the lowest power supply requirement of the components used.

Figure 5:
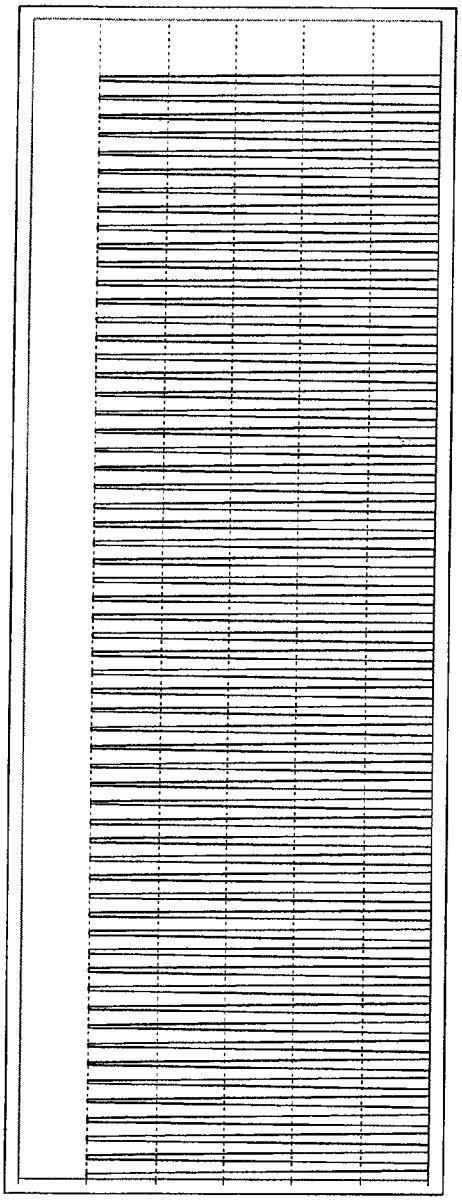
FIG. 5 shows a diagram of a high frequency signal, for use in accordance with an embodiment of the present invention.
Figure 6:
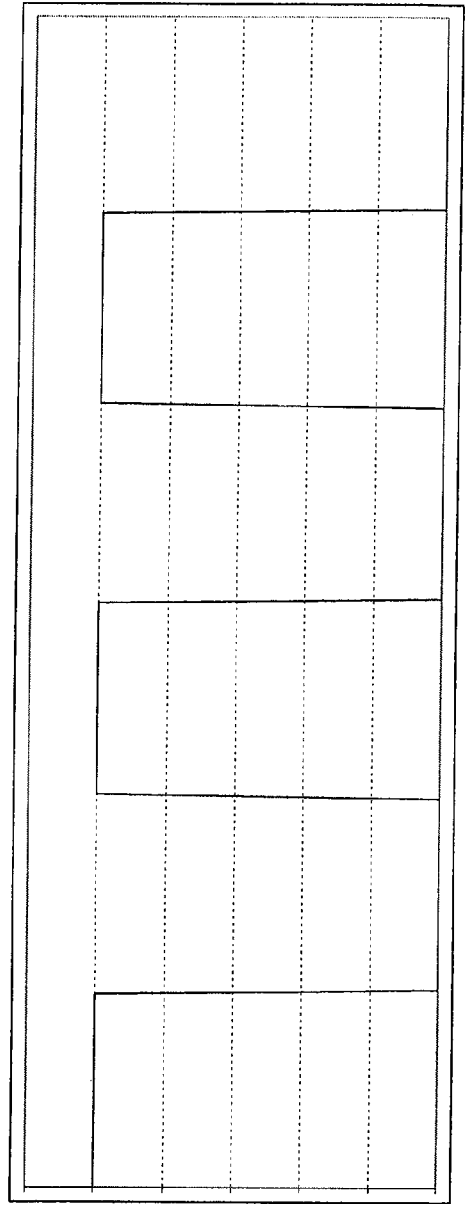
FIG. 6 shows a diagram of a low frequency signal, for use in accordance with an embodiment of the present invention.
Figure 7:
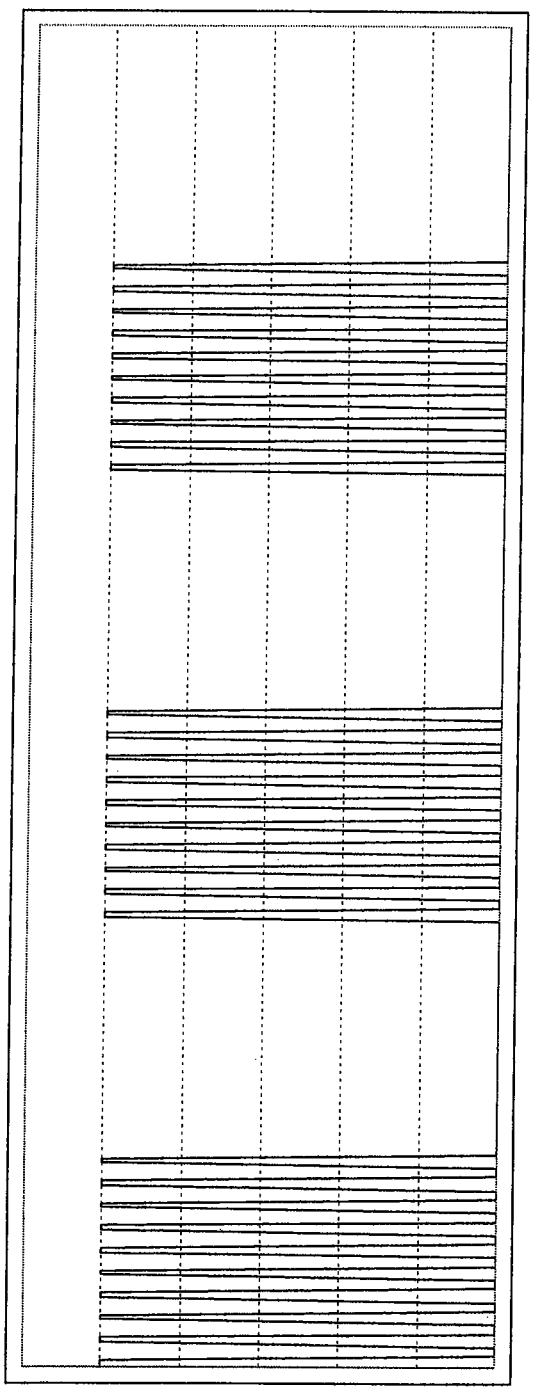
FIG. 7 shows a diagram of an amplitude modulated pulse width modulated signal, for use in accordance with an embodiment of the present invention.

With reference to FIGS. 5-7, a form of electrical signal for stimulating tissues is disclosed wherein an electrical signal of relatively high frequency (FIG. 1) is amplitude modulated by an electrical signal of relatively low frequency (FIG. 6), combining to form an electrical signal of the general form shown in FIG. 7. As discussed above, using pulse width modulation for the purpose of varying the duty cycle of the electrical signal of relatively high frequency, the time-averaged current deliverable by that signal can be controlled Hence, FIG. 7 shows an example of one embodiment of an amplitude modulated pulse width modulated (AMPWM) signal in which the signal of relatively low frequency shown in FIG. 6 and the signal of relatively high frequency shown in FIG. 5 form an AMPWM signal shaped similar to a square wave pulse train.

Figure 8:
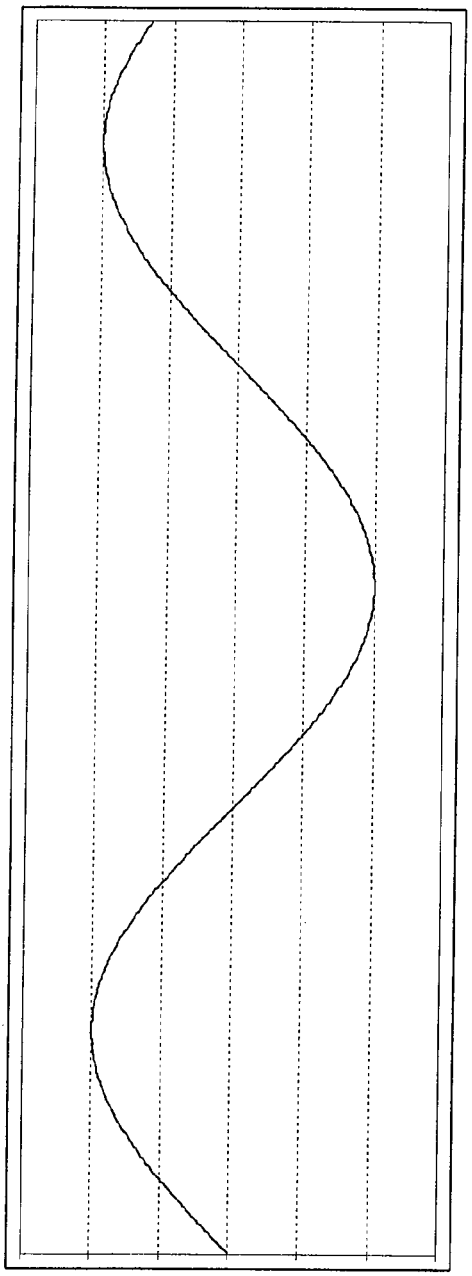
FIG. 8 shows a diagram of a low frequency sinusoidal signal, for use in accordance with an embodiment of the present invention.

However, an AMPWM signal may combine signals of shapes other than square waves. For example, FIG. 8 shows a signal of relatively low frequency that has a general sinusoidal form. When used to amplitude modulate a signal of relatively high frequency, as shown in the example of FIG. 1, a resulting AMPWM signal equivalent is that shown in FIG. 9.

Figure 10:
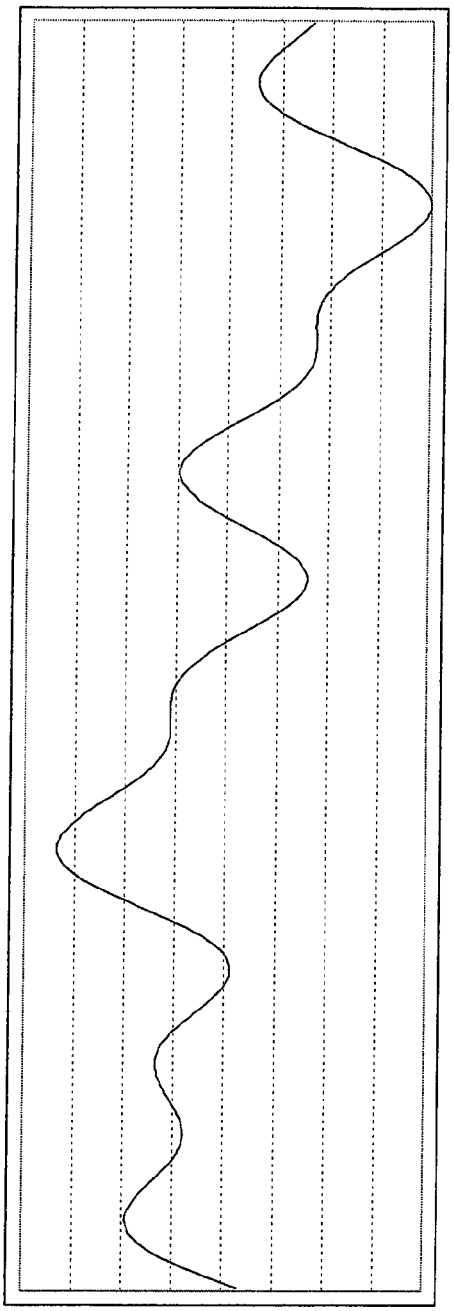
FIG. 10 shows a diagram of a low frequency composite sinusoidal signal, for use in accordance with an embodiment of the present invention.

An AMPWM signal may also be created from multiple relatively low frequency components. A signal with multiple frequency components can be created using methods such as inverse Fourier Transform theory. FIG. 10 shows an example of a composite sinusoidal signal with three relatively low frequency components that are created using an inverse Fourier Transform. Such relatively low frequency components may be selected to provide therapeutic electrical stimulation. One anticipated benefit of creating such a composite signal is to provide for therapeutic electrical stimulation that has multiple frequency-dependent beneficial effects on the tissues to which it is applied. When a composite signal such as that illustrated in FIG. 10 is used to amplitude modulate a signal of relatively high frequency, as shown in the example of FIG. 1, a resulting AMPWM signal equivalent is that shown in FIG. 11.

Figure 12:
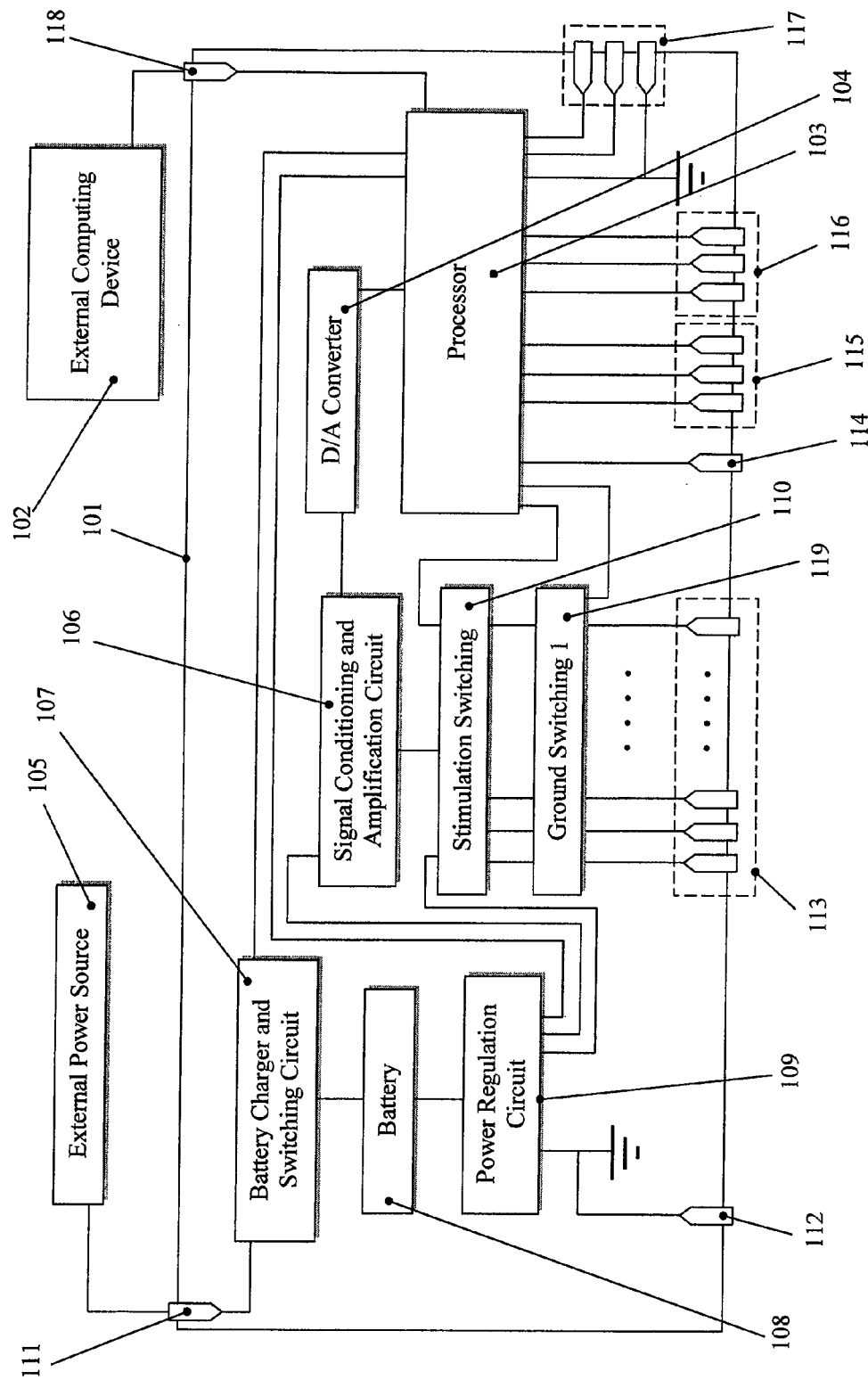
FIG. 12 shows a diagram of an electrical stimulation apparatus, in accordance with an embodiment of the present invention.

Various apparatus and circuits for creating and using an electrical signal for stimulating tissues such as an AMPWM signal are disclosed above. Here, an improved apparatus is provided, which provides for the generation of electrical tissue stimulation signals, such as AMPWM signals, that reduce tissue impedance and increase depth of signal penetration. A first embodiment of a tissue stimulation apparatus for providing an electrical tissue stimulation signal that reduces tissue impedance and increases depth of signal penetration is shown in FIG. 12, as comprising an electrical stimulation device 101 and an external computing device 102 is provided. Power for the electrical stimulation device 101 may be provided by an external power source 105, such as a line connection or an adapter for providing a conditioned electrical source, electrically coupled to the electrical stimulation device 101 through a power connector 111.

Internally, the electrical stimulation device 101 may include a battery charger and switching circuit 107 electrically coupled to the power connector 111, enabling the receipt of electricity from the external power source 105. A battery 108 may also be electrically coupled to the battery charger and switching circuit 107. The battery 108 may further be connected to other circuits of the electrical stimulation apparatus through the battery charger and switching circuit 107 and used to provide electrical power to the other circuits at times when isolation from line current is required or advantageous for operation of the apparatus, such as in times when the apparatus is being used to provide electrical stimulation to a subject. In practice, electrical isolation may be accomplished through a switching portion of the battery charger and switching circuit 107, which may be further electrically coupled to a controller or processor 103 configured to control various functions of the electrical stimulation device 101 such as electrical signal generation and as is further described herein. Programmed firmware, associated with processor technologies, for example, may provide for electrical signals to be sent from the processor 103 to control the switching portion of the battery charger and switching circuit 107 and to electrically decouple the electrical stimulation device 101 from the external power source 105 when isolation is required or desirable. At times when isolation is not required or desirable, such components as the processor 103, external power source 105 and battery charger, and switching circuit 107 may be used to recharge the battery 108 in preparation for subsequent use. In other words, the processor 103 may be configured to command the switching portion of the battery charger and switching circuit 107 to couple the external power source 105 to the battery 108 when isolation of the electrical stimulation device 101 is not required or desirable and to decouple the external power source 105 from the battery 108 when isolation is required or desirable. This coupling may be accomplished either as a result a signal being sent to a processor 103 arising from a manual input such as the manual decoupling of an external power source 105 from line power, or automatically arising from a software signal being sent to a processor 103 whenever an operator utilizes a software interface for using the apparatus to electrically stimulate a subject. In other words, the processor 103 may be programmed to automatically decouple external power in response to an operator's use of a software interface to use the apparatus to electrically stimulate a subject.

The battery 108 or other power source may subsequently energize a power regulation circuit 109 that further provides conditioned power to other circuits of the electrical stimulation device 101 and a common reference ground that may be used by all circuits. A ground connector 112 may be used to provide electrical coupling to external circuits, such as those described herein, for common grounding purposes.

Figure 13:
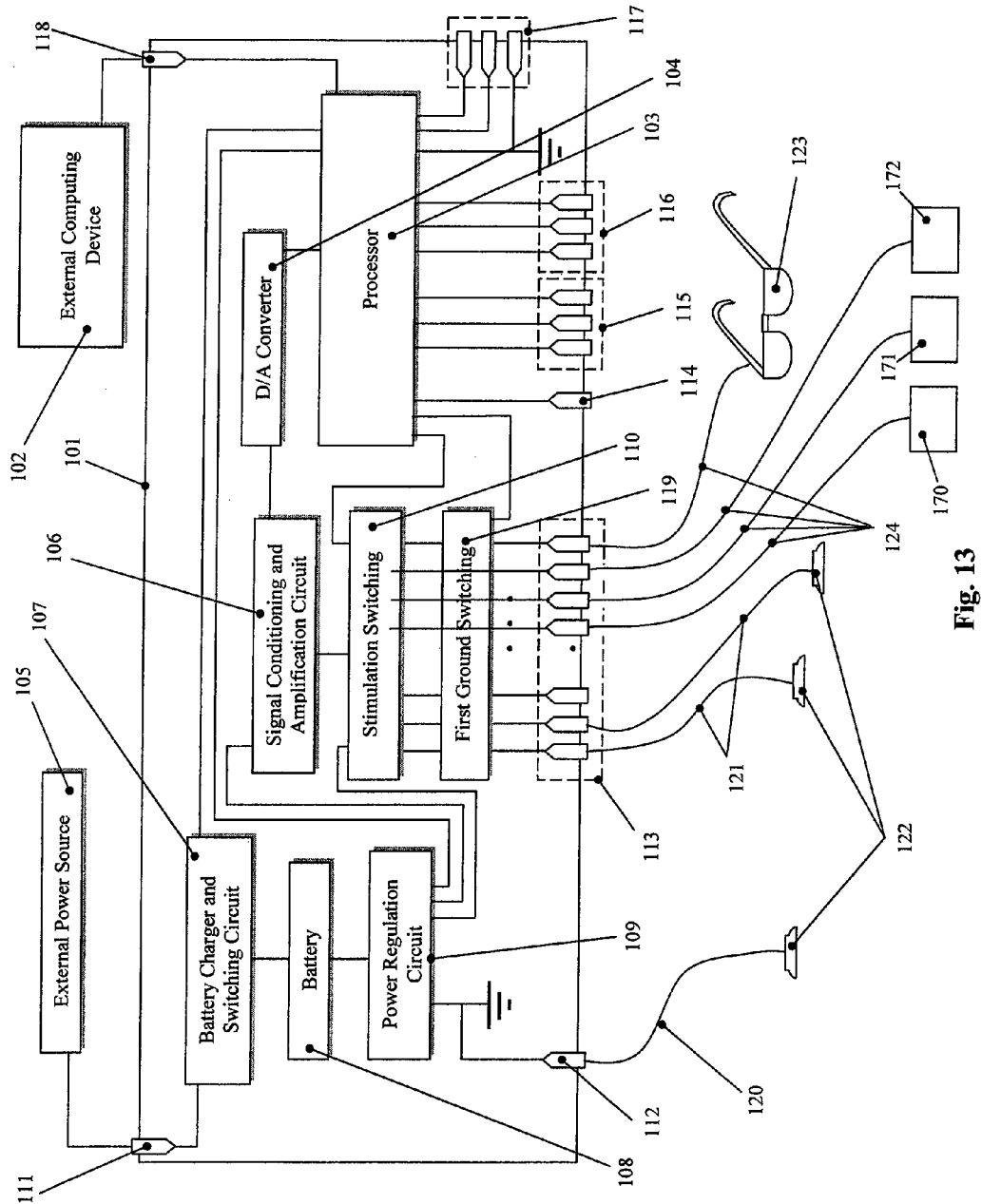
FIG. 13 shows a diagram of an electrical stimulation apparatus, in accordance with an embodiment of the present invention.

As is also shown in the embodiment of FIG. 13, conditioned power from the power regulation circuit 109 may further be used to energize the processor 103, whereupon a circuit for creating or generating an electrical signal for stimulating tissues is realized. This stimulation signal generation circuit may comprise the processor 103, a digital-to-analog (D/A) converter 104, a signal conditioning and amplification circuit 106, a stimulation switching circuit 110, and a first ground switching circuit 119. Further, the tissue stimulation apparatus may include an external computing device 102 coupled to the processor 103 through any suitable computer data cable 118 or similar interface, such as a wireless interface. The external computing device 102 may provide and be used as a user interface via software, and may provide for communication between a user and the processor 103, such communication comprising the flow of any and all forms of data and control signals to set and modify operational parameters of the electrical stimulation device 101. In other words, the external computing device is programmed to exchange data and control signals with the processor and to allow a user to modify operational parameters of the electrical stimulation apparatus.

The present invention may be implemented using hardware, software or a combination thereof and may be implemented in one or more computer systems or other processing systems. In one embodiment, the invention is directed toward one or more computer systems capable of carrying out the functionality described herein. An example of such a computer system is shown at 200 in FIG. 67.

The computer system 200 includes at least one processor 204 that is connected to a communication infrastructure 206 (e.g., a communications bus, cross-over bar, or network). Any suitable software embodiments may be used with this exemplary computer system, and the invention may be implemented using any suitable computer system and/or architectures.

The computer system 200 may include a display interface 202 that forwards graphics, text, and other data from the communication infrastructure 206 or from a frame buffer (not shown) for display on a display unit 230. The computer system 200 may also include a main memory 208, preferably random access memory (RAM), and may also include a secondary memory 210. The secondary memory 210 may include, for example, a hard disk drive 212 and/or a removable storage drive 214 such as a floppy disk drive, a magnetic tape drive, or an optical disk drive, etc. The removable storage drive 214 may be configured to read from and/or writes to a removable storage unit 218 in a well-known manner. The removable storage unit 218 may include a floppy disk, magnetic tape, optical disk, etc., which may be read by and written to the removable storage drive 214. The removable storage unit 218 may include a computer usable storage medium having stored therein computer software and/or data.

In alternative embodiments, the secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as that found in video game devices), a removable memory chip (such as an erasable programmable read only memory (EPROM), or programmable read only memory (PROM)) and associated socket, and other removable storage units 222 and interfaces 220, which allow software and data to be transferred from the removable storage unit 222 to the computer system 200.

The computer system 200 may also include a communications interface 224. The communications interface 224 may be configured to allow software and data to be transferred between the computer system 200 and external devices. The communications interface 224 may include a modem, a network interface (such as an Ethernet card), a communications port, a Personal Computer Memory Card International Association (PCMCIA) slot and card, etc. Software and data transferred via communications interface 224 are in the form of signals 228, which may be electronic, electromagnetic, optical or other signals capable of being received by communications interface 224. These signals 228 are provided to communications interface 224 via a communications path (e.g., channel) 226. This path 226 carries signals 228 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 214, a hard disk installed in hard disk drive 212, and signals 228. These computer program products provide software to the computer system 200. The invention may include such computer program products.

Computer programs (also referred to as computer control logic) are stored in main memory 208 and/or secondary memory 210. Computer programs may also be received via communications interface 224. Such computer programs, when executed, enable the computer system 200 to perform according to the features of the present invention, as discussed herein. The computer programs, when executed, enable the processor 204 to perform according to the features of the present invention. Accordingly, such computer programs serve as controllers of the computer system 200.

In an embodiment where the invention includes the use of software, the software may be stored in a computer program product and loaded into computer system 200 using the removable storage drive 214, the hard drive 212, or the communications interface 224. The control logic (software), when executed by the processor 204, causes the processor 204 to perform according to the functions of the invention as described herein. In another embodiment, the invention may be implemented primarily in hardware using, for example, hardware components, such as application specific integrated circuits (ASICs). Implementation of the hardware state machine so as to perform the functions described herein will be apparent to persons skilled in the relevant art(s).

In yet another embodiment, the invention may be implemented using a combination of both hardware and software.

In some embodiments, and as shown in FIG. 12, generating an electrical signal for stimulating tissues begins with signal parameters being established through various software methods used in an external computing device 102 and communicated to a processor 103 via any suitable data cable 118 or similar interface, such as a wireless interface. In other words, the external computing device 102 is configured to establish parameters of the electrical signals generated by the electrical stimulation device 101. Such signal parameters include, but are not limited to waveform, frequency components, phase, pulse width, duty cycle, and amplitude components such as minimum amplitude, maximum amplitude, and offset voltage. Various methods of establishing signal parameters may be used with the electrical stimulation device 101.

Upon establishment of signal parameters in a processor 103, along with establishment of other operational parameters, such as the aforementioned decoupling of an external power source 105, signals are sent from the processor 103 to a D/A converter 104, whereupon an analog voltage representing an electrical signal for stimulating tissues is first achieved. The analog voltage is further provided to an electrically coupled signal conditioning and amplification circuit 106, where a substantially equivalent signal is created with advantageous enhancements such as, but not limited to, increased voltage amplitude, decreased signal-to-noise ratio, and increased current capability.

In some embodiments, provisions may be made to the electrical stimulation apparatus for the selective control of the delivery of an electrical signal for stimulating tissues to a plurality of stimulation connectors 113. A stimulation switching circuit 110 is electrically coupled to the processor 103, whereupon control signals from the processor 103 allow for the signal from the signal conditioning and amplification circuit 106 to be advantageously switched to any number of independent electrical conductors or conduction paths. Further, the independent electrical conductors or conduction paths are electrically coupled with a first ground switching circuit 119, the first ground switching circuit 119 being further electrically coupled to the processor 103. Control signals from the processor 103 allow for selective switching of the independent conductors to an apparatus ground point, providing advantageous control of the independent conductors' use as either a conduction path for an electrical signal for stimulating tissues or a ground. Further electrical conduction paths are provided for each independent conductor passing through a first ground switching circuit 119, with each independent conductor terminating at one of a plurality of stimulation connectors 113.

The apparatus may include a number of electrical conductors that provide electrical coupling between a number of connectors and input/output (I/O) ports of a processor 103 in the electrical stimulation device 101 for the embodiments shown. Specifically, an auxiliary power supply connector 114 may be provided. The apparatus may include a switch comprising an electrical conductor first connected to an auxiliary power supply connector 114 then to a switch, then via another electrical conductor to an auxiliary I/O connector 116. The switch may be used for various purposes to indicate an event to the processor 103. One exemplary purpose is the use of the switch by a subject receiving electrical stimulation to mark a point in time of any particular interest.

The electrical stimulation device 101 may also include a plurality of conductors or control I/O connectors 115 that provide electrical coupling to I/O ports of the processor 103. Specifically, the control I/O connectors 115 may provide control signals between the processor 103 and various electrical apparatus or peripheral devices coupled to the electrical stimulation device 101, examples of which are described further herein. The apparatus may further include a number of lead test ports 117 electrically coupled to the processor 103 for electrically coupling electrical conductors or other couplings, to the processor 103 for the purpose of testing the electrical conducting integrity of any combination of such electrical conductors, or other couplings, such as wires combined with sensors, such as surface electrodes, henceforth referred to as "leads", used to conduct electrical energy between tissues and the electrical stimulation device 101.

As is also shown in FIG. 13, the electrical stimulation device 101 may include one or more ground leads 120, a plurality of stimulation leads 121, and provision at a terminating end of all leads for an electrode 122 adapted to be placed on tissues in either an invasive or non-invasive way. The apparatus also has provision for one or more external stimulation devices, such as an optical device 123, electromagnetic device 170, electromechanical device 171 or an audio device 172, electrically coupled by one or more external stimulation device cables 124. As shown in FIG. 13 the external stimulation devices may include an optical device 123 comprising eyeglasses adapted with illuminating or similar photic devices, such as light emitting diodes, or with displays for showing digital images to a subject undergoing therapy. The external stimulation devices may include an audio device 172 adapted to play music during therapeutic activity.

In operation, the apparatus of FIG. 13 provides stimulation from the electrical stimulation device 101 to tissues disposed between stimulation leads 121 and ground leads 120 such that an approximate vector path of electrical current flow extends between electrodes 122 associated with the stimulation leads 121 and electrodes 122 associated with the ground leads 120.

The processor 103 may be programmed to provide control signals that selectively control the stimulation switching circuit 110 and the first ground switching circuit 119 to cause the leads 121 to serve as either stimulation leads delivering stimulation or as ground leads serving as ground sources in such a way as to create multiple spatial paths of electrical stimulation through tissues.

In addition, as shown in FIG. 13, stimulation may be provided by an external stimulation device 123 operatively coupled to a stimulation connector 113 that is being used as an active stimulation electricity source through control of a stimulation switching circuit 110 by signals from a processor 103.

In addition, in the apparatus shown in FIG. 13, electrical conducting integrity of any stimulation lead 121, any ground lead 20, or any external stimulation device 123 may be tested by effecting physical contact between a lead, preferably by providing mechanical connection between a lead's conduction interface such as an electrode 122 and a lead test port 117. In testing for electrical conducting integrity, a processor 103 may be selectively used to output an electrical signal of known properties to a lead 121 being tested, whereupon the electrical signal conducted by the lead being tested can be acquired by the processor 103 through a lead test port 117. Any number of suitable analyses may be conducted, whereupon processor firmware, for example, makes a comparison between the electrical signal of known properties and the signal conducted through a lead being tested in order to determine the electrical conducting integrity of the lead.

Figure 14:
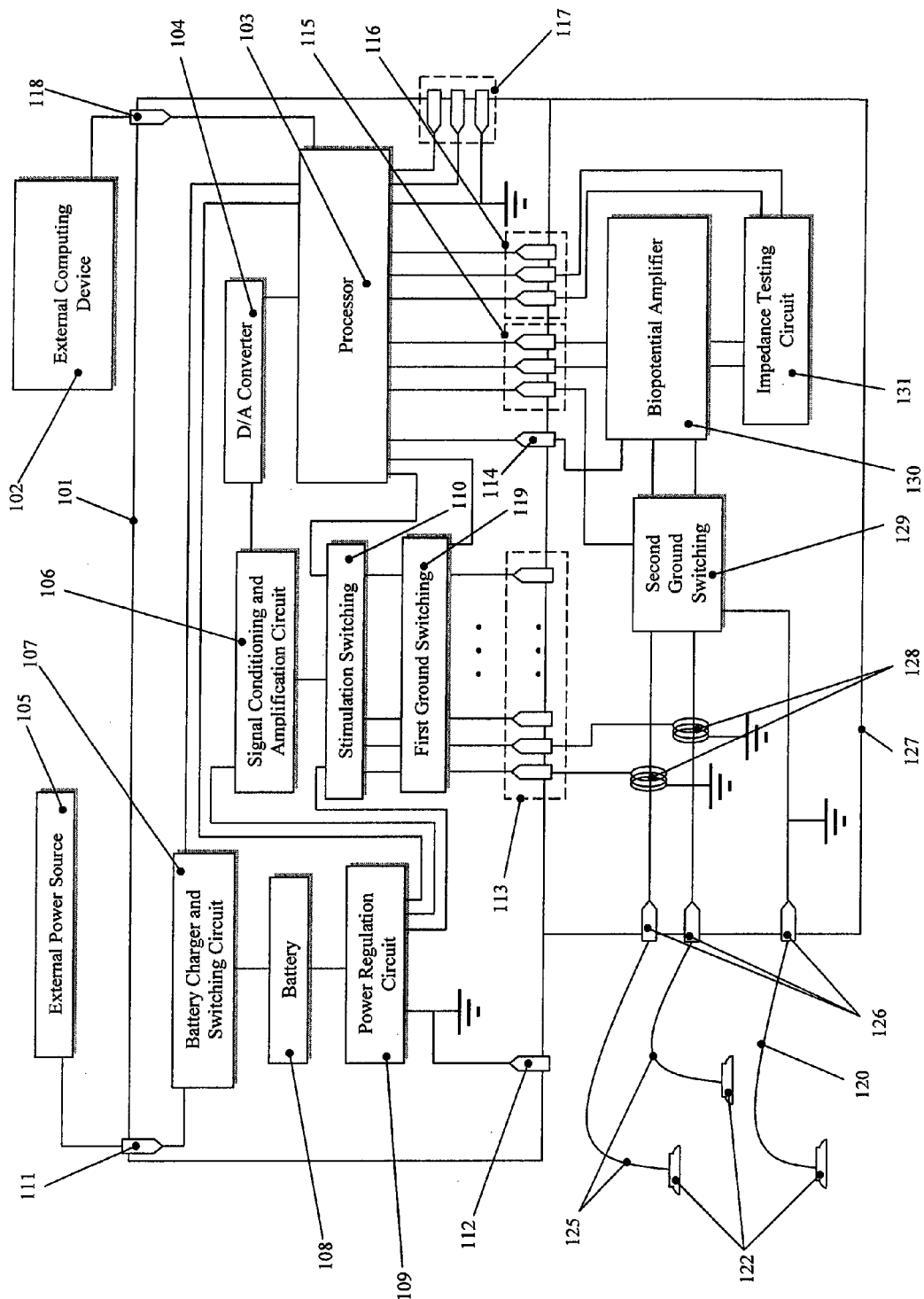
FIG. 14 shows a diagram of an electrical stimulation apparatus, in accordance with an embodiment of the present invention.

As shown in FIG. 14, a second embodiment of tissue stimulation apparatus for providing an electrical tissue stimulation signal that reduces tissue impedance and increases depth of signal penetration is shown as comprising an electrical stimulation device 101 and a biopotential acquisition device that measures biopotential voltage in tissue to be stimulated. The biopotential acquisition device may include a biopotential amplifier module 127 comprising a biopotential amplifier 130, an impedance testing circuit 131, a second ground switching circuit 129 and a series of inductors 128 operatively coupled to conductors extending from the second ground switching circuit 129 and terminating at biopotential acquisition lead connectors 126 and thus operatively coupled to biopotential acquisition leads 125 coupled to the connectors 126. Further provisions may be made for any number of biopotential acquisition leads 125, and any number of ground leads 120, each lead 125, 120 including a sensor such as a surface electrode 122 adapted to be placed on tissues. Further provisions may be made for electrical coupling of a biopotential amplifier module 127 to the electrical stimulation device 101 through stimulation lead connectors 113, a auxiliary power supply connector 114, control I/O connectors 115, and auxiliary I/O connectors 16 of the electrical stimulation device 101.

In an exemplary operation, the apparatus of FIG. 14 provides stimulation from the electrical stimulation device 101 to tissues, whereupon a biopotential voltage is measured by the biopotential amplifier 130 operatively coupled to any number of biopotential acquisition leads 125 and any number of ground leads 120 having electrodes 122 adapted to be placed on tissues, the biopotential voltage including, but not being limited to, electroencephalographic (EEG) voltage, electromyographic (EMG) voltage, and electrocardiographic voltage.

In the apparatus of FIG. 14, an electrical signal for stimulating tissues may be induced using the inductors 128 disposed adjacent the independent conductors extending from the second ground switching circuit 129 and terminating at biopotential acquisition lead connectors 126, the electrical signal being provided by the electrical stimulation device 101, and the inductors 128 being electrically coupled to the electrical stimulation device 101 at stimulation connectors 113, whereupon selective control of the electrical signal for stimulating tissues is accomplished as previously disclosed herein. In other words, the biopotential acquisition device includes one or more inductors 128 electrically coupled to the electrical stimulation device 101 and operatively coupleable one or more respective biopotential acquisition leads 125, the electrical stimulation device and inductors being configured to selectively deliver tissue stimulation signals through the one or more biopotential acquisition leads of the biopotential acquisition device.

In the apparatus of FIG. 14, data transfer of acquired biopotential voltage may be provided between the processor 103 and the biopotential amplifier 130 through any I/O port, such as a control I/O connector 15 or an auxiliary I/O connector 116. In certain embodiments, the biopotential voltage data may be used at any time to determine or alter parametric values of an electrical signal for stimulating tissues, such as via analysis using software in an external computing device 102 with subsequent control data being sent from the external computing device 102 to a processor 103 in an electrical stimulation device 101. In other words, the external computing device 102 is configured to determine parametric value of an electrical tissue stimulation signal in response to biopotential voltage data obtained by the biopotential acquisition device and to send corresponding control data to the processor 103.

In the apparatus of FIG. 14, the processor 103, for example, of the electrical stimulation device 101 may selectively sample biopotential voltage data from the biopotential amplifier 130 of the biopotential acquisition device at times of minimal electrical stimulation signal amplitude, preferably zero amplitude, within the period of a high frequency signal component of an AMPWM signal. Thus, the biopotential acquisition leads 125 may be used for the dual purpose of both acquiring biopotential voltage and delivering an electrical signal for stimulating tissues at overlapping, or simultaneous, times. The frequencies of a high frequency signal component of an AMPWM signal may be selected to be multiples of integral powers of two, including but not limited to integral multiples of 256 (i.e. 28) such as for example 14,336 hertz (256×56) and 16,384 hertz (256×64). Such selection of frequencies facilitates mathematical analysis of acquired biopotential voltage data. Such mathematical analysis may include a Fourier Transform analysis whereupon a number of samples per second equal to an integral power of two may be preferred. In the examples of AMPWM signal high frequency component frequencies of 14,336 hertz and 16,384 hertz given, sampling rates for biopotential voltage data of 2,048, 1,024, 512, 256 and 128 samples per second are readily achieved within equally spaced intervals of minimal electrical stimulation signal amplitude in the AMPWM signal.

In the apparatus of FIG. 14, the second ground switching circuit 129 may be operatively coupled to the electrical stimulation device 101 using a control I/O connector 15. Operationally, the second ground switching circuit 129 receives control signals from the processor 103, which allows for selective switching of any biopotential acquisition lead 125 to an apparatus ground point, permitting advantageous control of the biopotential acquisition lead's 125 use as either a conduction path for an electrical signal for stimulating tissues, a conduction path for a biopotential voltage to the biopotential amplifier 130, or a ground. Among other things, such selective switching of a biopotential acquisition lead 125 permits selective use as a reference lead to the biopotential amplifier 130 or as a differential lead to the biopotential amplifier 130, facilitating differential comparison of biopotential voltages at more than one acquisition site on a tissue.

In the apparatus of FIG. 14, an impedance testing circuit 131 may be included in the biopotential acquisition device and operationally coupled to the biopotential amplifier 130. The impedance testing circuit 131 may also be coupled to the electrical stimulation device 101 using auxiliary I/O connectors 16. In such use, the impedance testing circuit 131 may be used to monitor the impedance of tissues in mechanical contact with biopotential acquisition leads 125 and a ground lead 20, each comprising an electrode 122 adapted to be placed on the tissues. Data representing the impedance of tissues is transferred to the processor 103 of the electrical stimulation device 101 via electrical coupling, for example. The data representing impedance of tissues may be used to determine or alter parametric values of an electrical signal for stimulating tissues through, for example, analysis using software in the external computing device 102, with subsequent control data being sent from the external computing device 102 to the processor 103 in the electrical stimulation device 101.

The data representing impedance of tissues and ongoing monitoring for biopotential voltage integrity, such as, but not limited to, EEG measurement integrity, may be used to determine or alter parametric values of an electrical signal for stimulating tissues, such as an AMPWM signal.

The use of methods to monitor for biopotential voltage integrity accomplishes various means of guiding a user and assuring improved biopotential signal data throughout an acquisition time period. For example, the apparatus may include an alert for notifying a user if integrity is lost during treatment. Such alert may be provided, for example, via software analysis in an external computing device 102. In another embodiment, such alert may be sent to a remote indicator such as a pager worn by a user. Further, the apparatus may include various means of indicating to a user when good biopotential voltage integrity is achieved as biopotential acquisition leads 125 and ground leads 120 are first being applied to tissues, prior to the acquisition of data. Such indicators may be provided, for example, via graphic user interface software in an external computing device 102 or via any number of hardware indication means.

Figure 15:
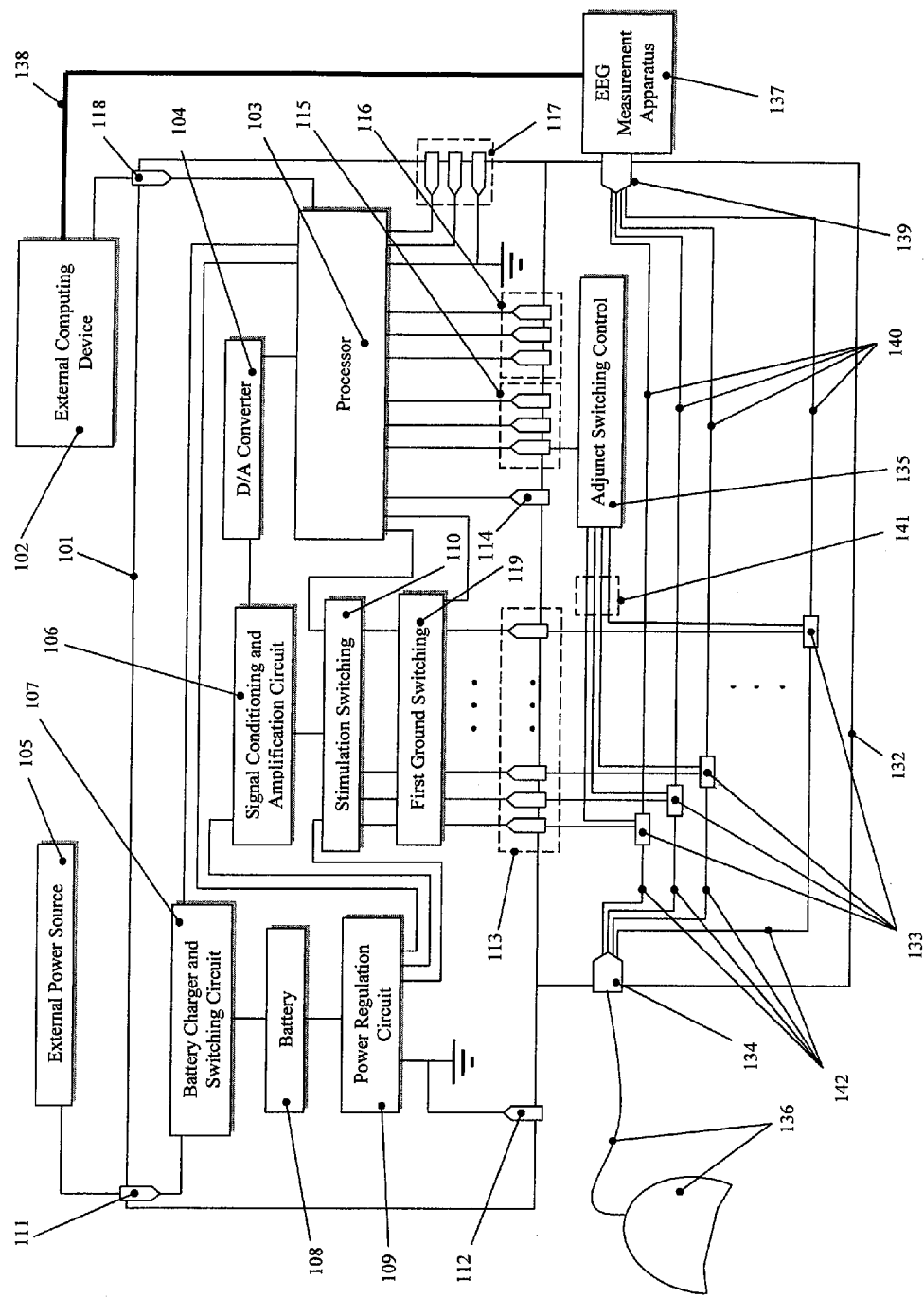
FIG. 15 shows a diagram of an electrical stimulation apparatus, in accordance with an embodiment of the present invention.

With reference to FIG. 15, another embodiment of a tissue stimulation apparatus for providing an electrical tissue stimulation signal that reduces tissue impedance and increases depth of signal penetration is shown as comprising an electrical stimulation device 101 and an adjunct electrical stimulation apparatus 132 to be used with an independent biopotential voltage measurement apparatus, such as, but not limited to, an EEG measurement apparatus 137. Under normal operating conditions, an EEG measurement apparatus 137 is typically used only for the purposes of acquiring EEG voltage data and for providing such data to an external computing device 102 through any data cable 138 or other coupling capable of sufficiently transferring the data. Acquisition of the EEG voltage is normally accomplished through any number of leads electrically coupled to an EEG measurement apparatus 137 at an interface 139, for example. Such number of leads may include an EEG sensor set 136 comprising, but not being limited to, a series of conductors, a series of electrodes and features for positioning the electrodes, such as via integration of such sensors in a cap adapted to be worn by a subject. In other words, the tissue stimulation apparatus may comprise a sensor set 136, an independent biopotential voltage measurement apparatus 137, and an adjunct electrical stimulation apparatus 132 operatively connected between the sensor set 136 and the independent biopotential voltage measurement apparatus. The independent biopotential voltage measurement apparatus 137 may be operatively coupled to the electrical stimulation device 101, and may be configured to transmit through stimulation connectors 113 to the sensor set, electrical tissue stimulation signals received from the electrical stimulation device 101, to transmit biopotential voltage from the sensor set 136 to the independent biopotential voltage measurement apparatus 137, and to receive control signals from the processor 103 of the electrical stimulation device 101 through control I/O connectors 115, The exemplary apparatus illustrated in FIG. 15 enables use of an independent biopotential voltage measurement apparatus, such as, but not limited to, an EEG measurement apparatus 137, within an apparatus for providing an electrical signal for stimulating tissues. This use may be accomplished by placing an adjunct electrical stimulation apparatus 132 operatively between an EEG sensor set 136 and an EEG measurement apparatus 137. The adjunct electrical stimulation apparatus 132 may include an adjunct switching control 135 operatively coupled to a processor 103 of an electrical stimulation device 101 using control I/O connectors 115. The adjunct electrical stimulation apparatus may also include a series of EEG lead conductors 142 and matched transfer conductors 140, for example, along with a series of adjunct switching circuits 133 operatively coupled to the adjunct switching control 135 via switching control conductors 141, and further operatively coupled to stimulation connectors 113 of the electrical stimulation device 101.

In operation, the apparatus of FIG. 15 provides for an adjunct electrical stimulation apparatus 132 operatively coupled to an electrical stimulation device 101 to both receive electrical signals through stimulation connectors 113 for stimulating tissues and to transfer control signals to a processor 103 through control I/O connectors 115. The adjunct electrical stimulation apparatus 132 may be further operatively coupled to an EEG sensor set 136 at a cable interface connector 134 for receiving EEG voltage. The adjunct electrical stimulation apparatus 132 may be further operatively coupled to an EEG measurement apparatus 137 at an interface 139 such as the same connecting features provided by an EEG sensor set 136.

Figure 16:
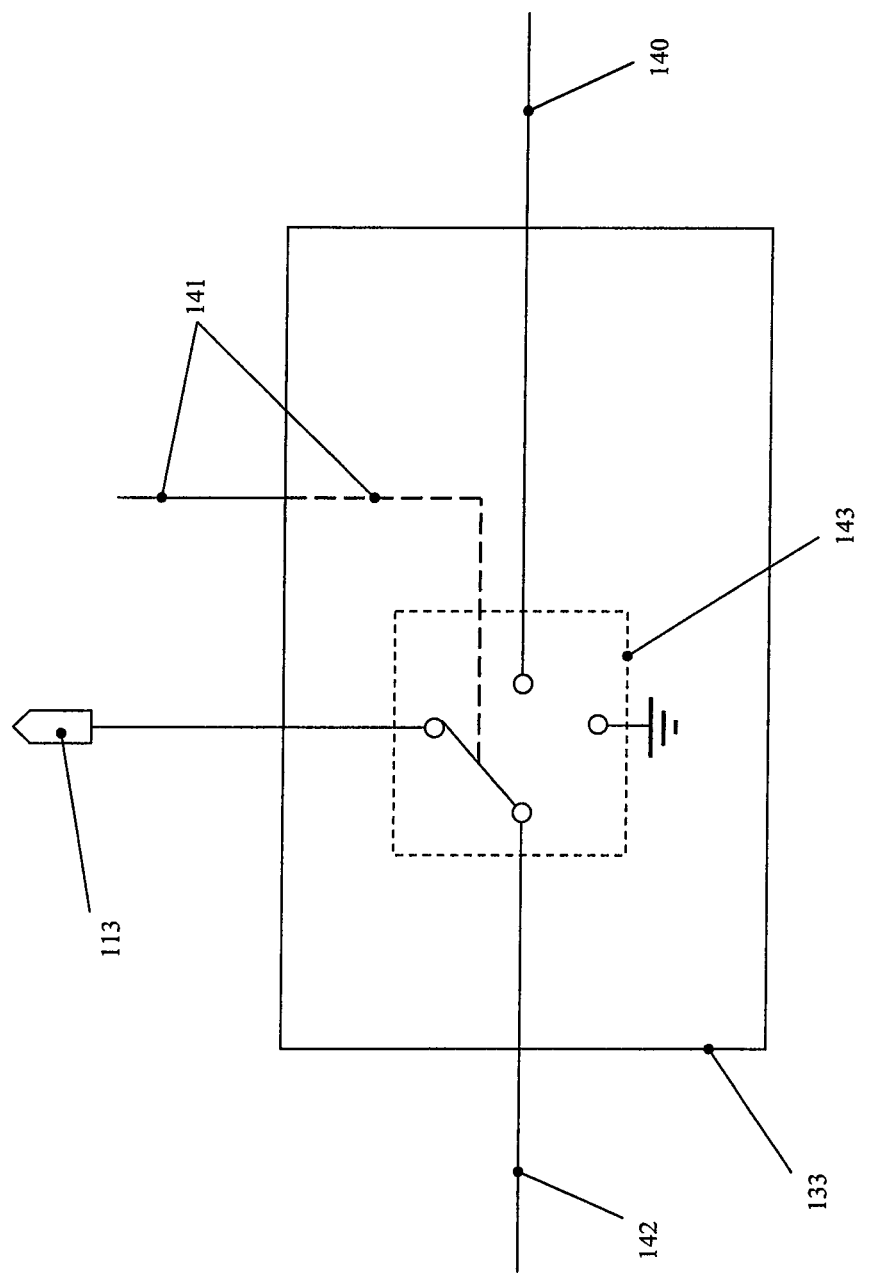
FIG. 16 shows a diagram of a switching circuit, in accordance with an embodiment of the present invention.

With reference to FIGS. 15 and 16, a series of adjunct switching circuits 133 may be provided, each comprising any substantial circuit for switching 143, for example, that provides a selectable conduction pathway for an EEG lead conductor 142 between (a) an electrical signal for stimulating tissues, such as provided by an electrical stimulation device 101 through electrical coupling at stimulation connectors 113, (b) a transfer conductor 140 terminated at an interface 139 and further provided to an independent EEG measurement apparatus 137, or (c) a ground. Further provision made in the adjunct switching circuit 133 may include switching control conductors 141 electrically coupled to an adjunct switching circuit 135, which may be used, for example, to determine the state of the adjunct switching circuit 133 and therefore the conduction path provided to the EEG lead conductor 142.

As shown in FIG. 15, the electrical stimulation device 101 may be combined with an adjunct electrical stimulation apparatus 132 and biopotential voltage measurement apparatus, such as an EEG measurement apparatus 137. At times, for example, when a biopotential voltage measurement is required, biopotential voltage from a particular EEG lead conductor 142 may be directed to a transfer conductor 140 by selective switching via an adjunct switching control 135 operated by the processor 103 in the electrical stimulation device 101. Alternately, at times, such as when an electrical signal for stimulating tissues is required, the signal may be directed from a stimulation connector 113 to a particular EEG lead conductor 142 by selective switching from an adjunct switching control 135 operated by the processor 103 in the electrical stimulation device 101. Alternately, at times, such as when a particular EEG lead conductor 142 is to be grounded, selective switching from an adjunct switching control 135 operated by the processor 103 in the electrical stimulation device 101 may be used to electrically couple the EEG lead conductor 142 to ground. In other words, the processor 103 of the electrical stimulation device 101 and the adjunct switching control may direct biopotential voltage from selected electrodes of the sensor set 136 to the biopotential measurement apparatus 137 by selective switching via the adjunct switching control 135 operated by the processor 103 when a biopotential voltage measurement is required, may direct tissue stimulation signals from the electrical stimulation device 101 through selected stimulation connectors 113 to corresponding electrodes of the sensor set 136 through respective EEG lead conductors 142 by selective switching via the adjunct switching control 135 operated by the processor 103 when tissue stimulation is required, and may couple selected electrodes of the sensor set 136 to ground by selective switching via the adjunct switching control 135 operated by the processor 103 when grounding of an electrode is required.

As shown in FIG. 14, inductors 128 and a second ground switching circuit 129 of the apparatus of FIG. 14 may be replaced, for example, by an adjunct switching circuit 133 and an adjunct switching control 135 to control the use of individual leads. In other words, the biopotential acquisition device of FIG. 14 may be modified to include at least one adjunct switching circuit 133 and an adjunct switching control 135 electrically coupled to the electrical stimulation device 101, with the adjunct switching circuit 133 being operatively coupled to at least one biopotential acquisition lead 125, the electrical stimulation device 101 and an adjunct switching control 135 selectively connecting the electrical stimulation device 101 to selected leads to transmit tissue stimulation signals to the selected leads and connecting selected leads to the biopotential amplifier 130 to transmit biopotential voltages to the biopotential amplifier 130.

Figure 17:
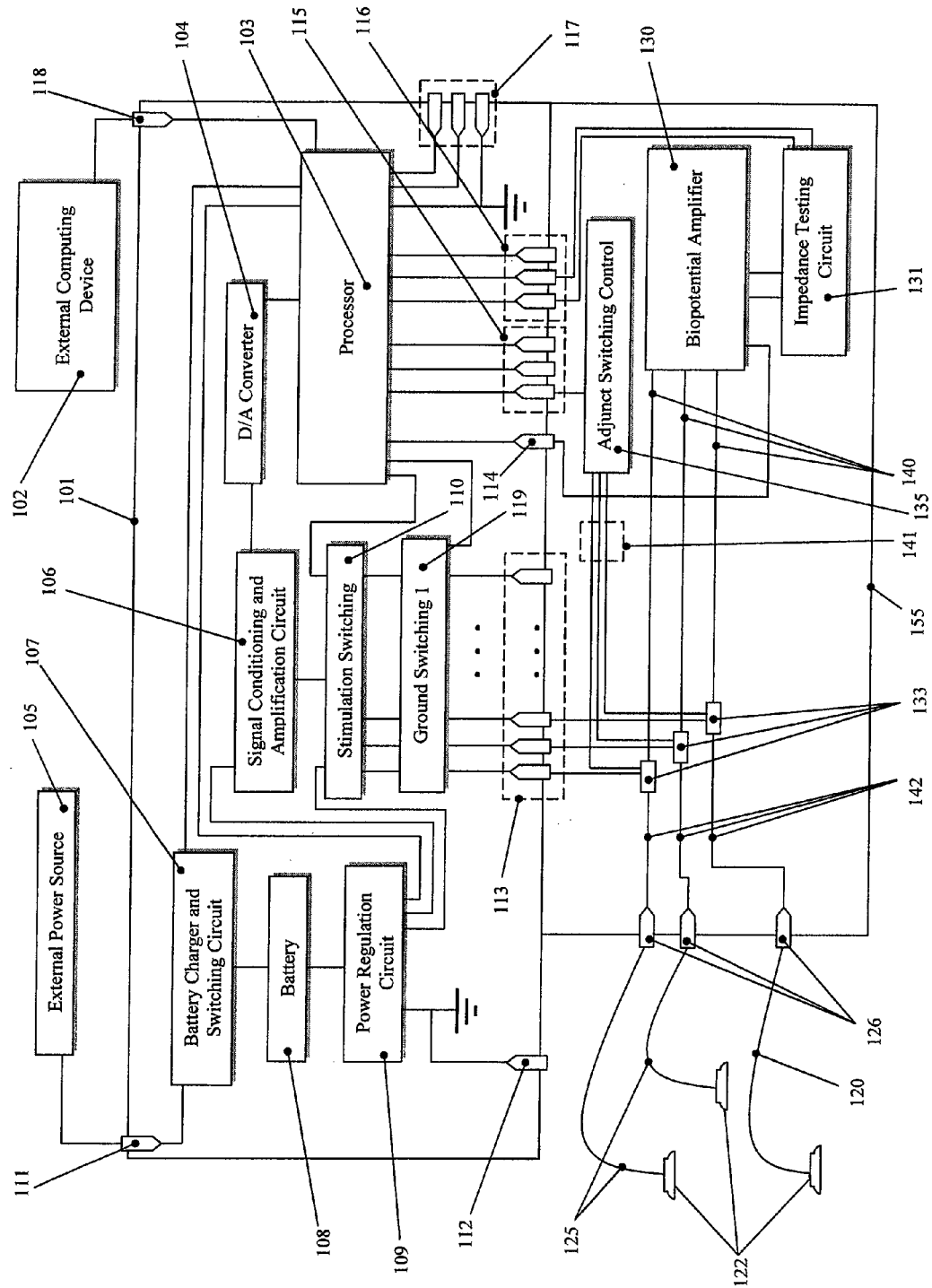
FIG. 17 shows a diagram of an electrical stimulation apparatus, in accordance with an embodiment of the present invention.

Accordingly, as shown in FIG. 17, the tissue stimulation apparatus may comprise an electrical stimulation device 101 and a biopotential amplifier and switching module 155, and the module may further comprise a biopotential amplifier 130, an impedance testing circuit 131, a series of EEG lead conductors 142 operatively coupled to conductors terminating at biopotential acquisition lead connectors 126, matched transfer conductors 140, a series of adjunct switching circuits 133 operatively coupled to the adjunct switching control 135 via switching control conductors 141, and further operatively coupled to stimulation connectors 113 of an electrical stimulation device 101. Further provisions may be made for any number of biopotential acquisition leads 125, and any number of ground leads 120, and a mechanism that may be used with the leads to provide for electrodes 122 adapted to be placed on tissues. Further provisions may be made for electrical coupling of a biopotential amplifier and switching module 155 to the electrical stimulation device 101 through stimulation connectors 113, auxiliary power supply 14, control I/O connectors 115 and auxiliary I/O connectors 16.

In an exemplary operation, the apparatus of FIG. 17 provides stimulation from the electrical stimulation device 101 to tissues, whereupon a biopotential voltage may be measured by a biopotential amplifier 130 operatively coupled through an adjunct switching circuit 133, transfer conductor 140 and EEG lead conductor 142 to any number of biopotential acquisition leads 125, any number of ground leads 120 and the electrode 122 adapted to be placed on tissues. The biopotential voltage may include, but is not limited to including, electroencephalographic (EEG) voltage, electromyographic (EMG) voltage, and/or electrocardiographic voltage.

As shown in FIG. 17, an electrical signal for stimulating tissues may be electrically coupled to any number of biopotential acquisition leads 125, any number of ground leads 120 and the electrode 122 adapted to be placed on tissues, the electrical signal being provided by the electrical stimulation device 101, through an adjunct switching circuit 133, transfer conductor 140 and EEG lead conductor 142, where the adjunct switching circuit 133 is operatively coupled to an adjunct switching control 135 via switching control conductors 141, and further operatively coupled to stimulation connectors 113 of the electrical stimulation device 101, whereupon selective control of the electrical signal for stimulating tissues may be accomplished as previously disclosed herein.

Figure 18:
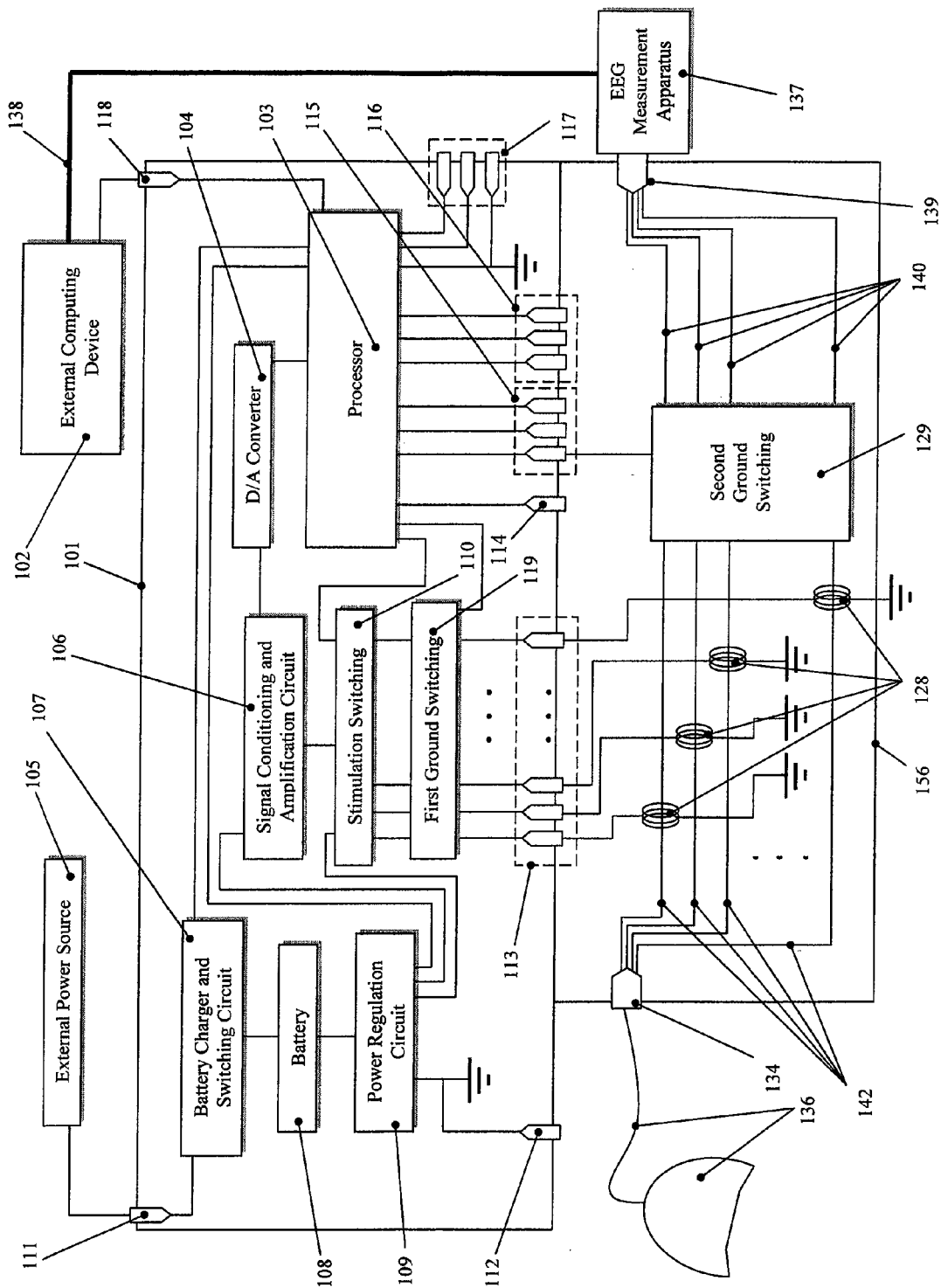
FIG. 18 shows a diagram of an electrical stimulation apparatus, in accordance with an embodiment of the present invention.

Further, and with particular reference to FIG. 18, the adjunct switching circuit 133 and an adjunct switching control 135 of the apparatus of FIG. 15 may be replaced by inductors 128 and a second ground switching circuit 129, as taught in FIG. 14 to control the use of individual leads. In other words, the adjunct electrical stimulation apparatus 132 may be modified to include a ground switching circuit 129 operatively coupled to the processor 103 of the electrical stimulation device 101, to the biopotential amplifier 130, and by conduction paths to respective electrodes of the sensor set, a plurality of inductors 128 operatively coupled to the electrical stimulation device 101 and to the conduction paths, and the processor and ground switching circuit may be configured to provide selectable conduction pathways for tissue stimulation signals between the electrical stimulation device 101 and the electrodes of the sensor set, and for biopotential voltages between the electrodes of the sensor set and the biopotential voltage measurement apparatus 137.

Accordingly, as shown in FIG. 18, as the tissue stimulation apparatus may comprise a basic electrical stimulation apparatus 1 and an adjunct electrical induction and switching apparatus 156 to be used with an independent biopotential voltage measurement apparatus, such as, but not limited to, an EEG measurement apparatus 137. Under normal operating conditions, an EEG measurement apparatus 137 is typically utilized only for the purposes of acquiring EEG voltage data and for providing such data to an external computing device 102 through any data cable 138 or other coupling capable of sufficiently transferring the data. Acquisition of the EEG voltage may be accomplished through any number of leads electrically coupled to an EEG measurement apparatus 137 at an interface 139, for example. Such number of leads may include an EEG sensor set 136 comprising, but not being limited to, a series of conductors, a series of electrodes and features for positioning the electrodes, such as a cap adapted to be worn by a user and into which the electrodes may be integrated.

The exemplary apparatus illustrated in FIG. 18 enables use of an independent biopotential voltage measurement apparatus, such as, but not limited to, an EEG measurement apparatus 137, within the tissue stimulation apparatus. This use may be accomplished by placing an adjunct electrical induction and switching apparatus 156 operatively between an EEG sensor set 136 and an EEG measurement apparatus 137, whereupon said adjunct electrical induction and switching apparatus 156 comprises a second ground switching circuit 129 operatively coupled to any number of transfer conductors 140 and EEG lead conductors 142. In the system of FIG. 18, a second ground switching circuit 129 may be further operatively coupled to an electrical stimulation device 101 using a control I/O connector 15. Operationally, the second ground switching circuit 129 receives control signals from a processor 103, which allows for selective switching of any EEG lead conductor 142 to a system ground point, permitting advantageous control of the EEG lead conductor's 142 use as either a conduction path for an electrical signal for stimulating tissues, or a conduction path for an EEG measurement apparatus 137, or a ground. Further provisions may be made for electrical coupling of an adjunct electrical induction and switching apparatus 156 to a basic electrical stimulation apparatus 1 through stimulation connectors 113, auxiliary power supply 14, control I/O connectors 115 and auxiliary I/O connectors 16.

In operation, the apparatus of FIG. 18 provides for an adjunct electrical induction and switching apparatus 156 operatively coupled to the electrical stimulation device 101 to both receive electrical signals through stimulation connectors 113 for stimulating tissues and to transfer control signals between a processor 103 and a second ground switching circuit 129 through control I/O connectors 115. The adjunct electrical induction and switching apparatus 156 may further be operatively coupled to an EEG sensor set 136 at a cable interface connector 134 for receiving EEG voltage. The adjunct electrical stimulation apparatus 132 may further be operatively coupled to an EEG measurement apparatus 137 at an interface 139 such as the same connecting features provided by an EEG sensor set 136.

Figure 19:
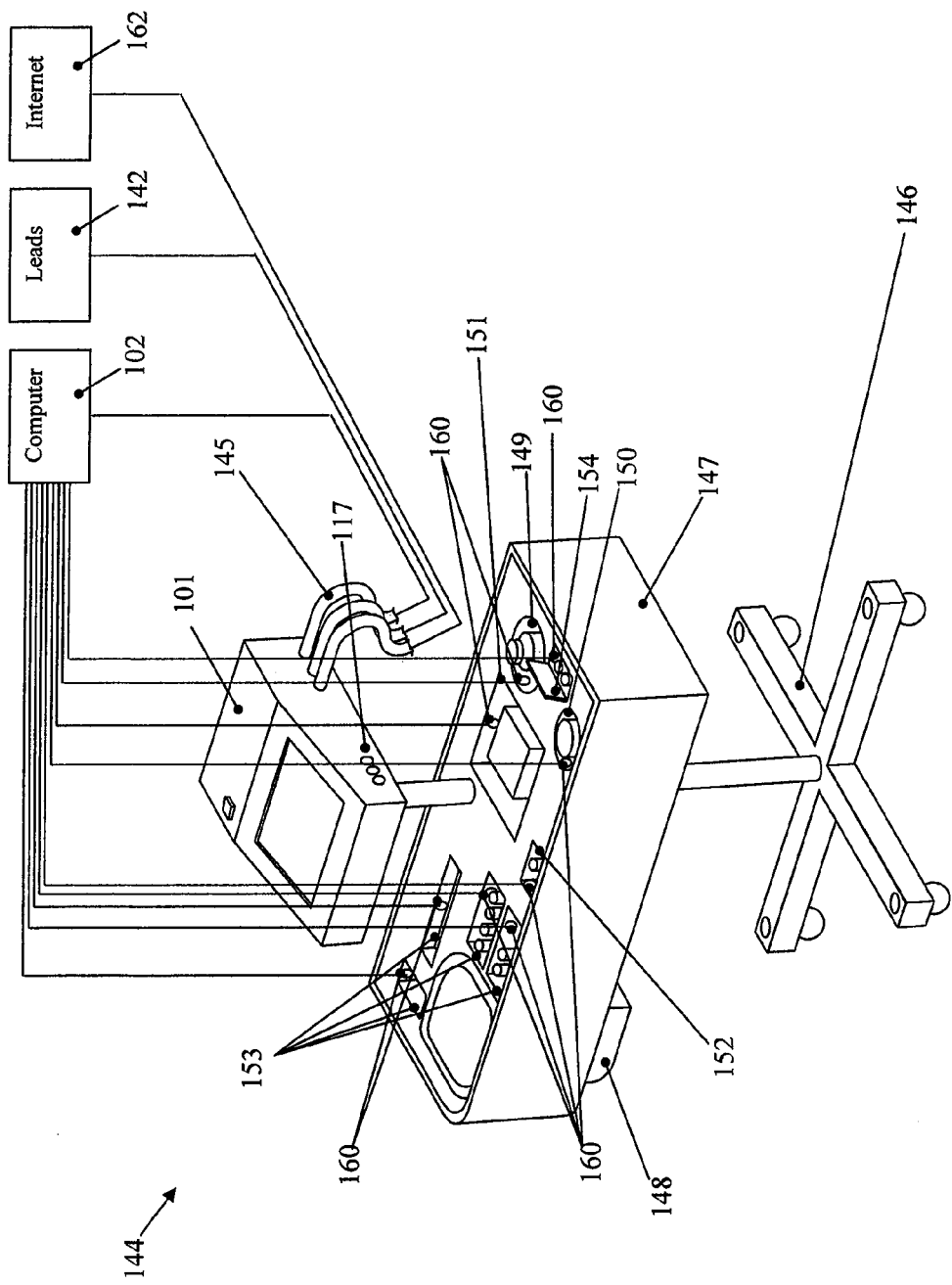
FIG. 19 shows a diagram of a mobile electrical stimulation apparatus, in accordance with an embodiment of the present invention.
Figure 20:
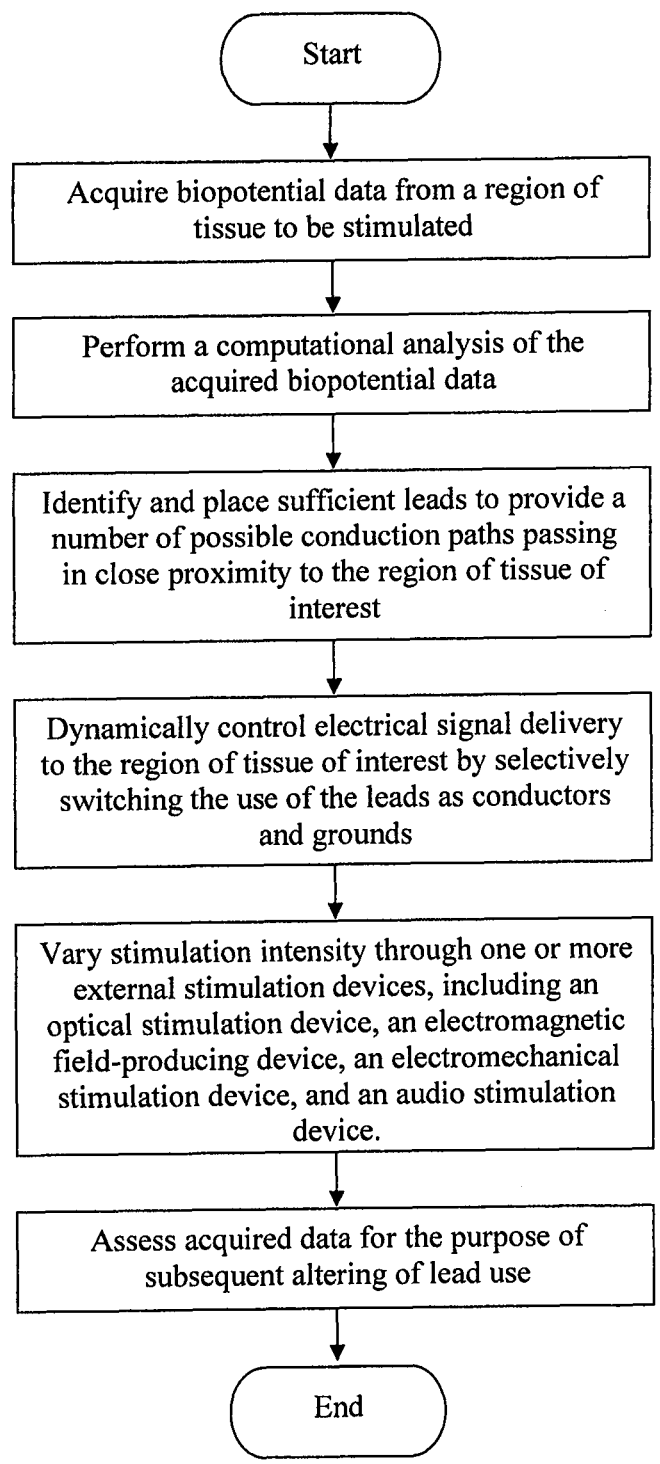
FIG. 20 shows a flow diagram of method of applying therapeutic electrical stimulation, in accordance with an embodiment of the present invention.

With reference to FIG. 19, another embodiment of a tissue stimulation apparatus 144 for providing an electrical signal for stimulating tissues comprises an electrical stimulation device 101, may comprise an external computing device 102, and comprises one or more circuits adapted to provide electrical stimulation signals from the electrical stimulation device to tissues of a subject in accordance with features and operations of the embodiments, or substantial equivalents, such as are illustrated in FIGS. 12-18 and taught herein. With further reference to FIG. 19, the tissue stimulation apparatus 144 for providing an electrical signal for stimulating tissues may include a mobile apparatus 146 such as a wheeled cart or a wheeled stand for transportability, and a material supplies storage and use apparatus 147 that carries consumable supplies for use in administering tissue stimulation signals to a subject.

In operation, the tissue stimulation apparatus 144 of FIG. 19 provides a mobile system for providing an electrical signal for stimulating tissues, wherein the mobile apparatus 146 facilitates movement of the tissue stimulation apparatus 144 to a subject, and wherein a tissue stimulation apparatus 144 may provide stimulation through composite stimulation leads 145, such composite stimulation leads 145 comprising any combination of stimulation leads 121, ground leads 120, and/or external stimulation device cables 124.

In the tissue stimulation apparatus 144 shown in FIG. 19, a number of consumable supplies may be used with the tissue stimulation apparatus to provide an electrical signal for stimulating tissues, the supplies including, but not being limited to conductive pastes, conductive gels, cleaning materials, such as cotton or gauze, cleaning agents, such as rubbing alcohol, and/or any number of supporting materials. In the tissue stimulation apparatus 144 of FIG. 19, the material supplies storage and use apparatus 147 may be operatively coupled to or carried by the mobile apparatus 146, for example, to enable presenting the consumable supplies during use and storing the consumable supplies during non-use. Specifically, the material supplies storage and use apparatus 147 may comprise, for example, a plurality of receptacles and storage features, including, but not limited to, a waste storage receptacle 148, a conductive gel receptacle 149, a conductive paste receptacle 150, a cleaning materials receptacle 151, an alcohol receptacle 152, any number of other supporting materials receptacles 153, and/or an electrode storage receptacle 154.

In the tissue stimulation apparatus 144 shown in FIG. 19, provisions may be made for any method of sensing the quantities of materials stored in receptacles such as, but not limited to, the waste storage receptacle 148, the conductive gel receptacle 149, the conductive paste receptacle 150, the cleaning materials receptacle 151, the alcohol receptacle 152, and/or any further number of supporting materials receptacles 153. The method is further realized using any suitable computing device 102 integral to operate with the composite electrical stimulation apparatus 144 to acquire signals from sensors 60 using software to manage inventory. In other words, the tissue stimulation apparatus 144 may include one or more sensors 60 carried by the material supplies and use apparatus 147 and configured to sense the quantities of materials stored in receptacles of the material supplies storage and use apparatus 147. The tissue stimulation apparatus 144 may include a computing device 102 coupled to the one or more sensors and configured to manage inventory in response to signals acquired from the one or more sensors. The method may further include use of, for example, various alerts when inventory of any material reaches a predetermined low point. In other words, the tissue stimulation apparatus 144 may be configured to generate an alert when inventory of any material reaches a predetermined low point. The method may further include interfacing, such as via software, to provide orders to replenish material inventory when a pre-determined low point is reached. In other words, the tissue stimulation apparatus 144 may be configured to order materials necessary to replenish inventory when a pre-determined low point is reached. The method may further provide for interfacing with a network, such as the Internet 62, and to enable ordering by a remote supply entity for the purposes of replenishing material inventory when a pre-determined low point is reached. In other words, the tissue stimulation apparatus 144 may be configured to order materials by interfacing with a communications network such as the internet 62.

In the tissue stimulation apparatus 144 shown in FIG. 13, the electrode storage receptacle 154 may be configured to provide storage for electrodes 122 for leads, the electrodes made of, for example, photosensitive materials, such as silver-silver/chloride. In practice, the electrode storage receptacle 154 allows the electrodes 122 to be covered so as to block access of ambient light during periods of non-use.

In tissue stimulation apparatus such as those shown in a number of the figures, the use of leads may be dynamically altered between (a) conducting biopotential voltages, (b) conducting an electrical signal for stimulating tissues and (c) a ground, in conjunction with the use of computational analysis of the acquired data, such as biopotential data, providing indication of a region of tissue to be stimulated. Based on such analysis, sufficient leads may be identified and appropriately placed so as to provide a number of possible conduction paths passing in near proximity to the region of tissue of interest. Then, control signals from a processor 103 of an electrical stimulation device 101 may be used to selectively switch use of the leads, in accordance with methods taught herein, to provide any number of dynamically controlled conductors and grounds for an electrical signal for stimulating tissues. The electrical stimulation device 101 may then be used to deliver the electrical signal to the appropriate region of tissues and may further be used to assess subsequently acquired data for the purpose of subsequent altering of lead use. In other words, tissues of a subject may be stimulated by first providing a tissue stimulation apparatus configured to dynamically alter the use of leads between conducting biopotential voltages, conducting an electrical signal for stimulating tissues, and grounding, in response to a computational analysis of biopotential data acquired from a region of tissue to be stimulated, acquiring biopotential data from a region of tissue to be stimulated, performing a computational analysis of the acquired biopotential data, in response to the analysis, identifying and placing sufficient leads so as to provide a number of possible conduction paths passing in near proximity to a region of tissue of interest, and dynamically controlling electrical signal delivery to the region of tissue of interest by selectively switching the use of the leads as conductors and grounds. In addition subsequently acquired data may be assessed for the purpose of subsequent altering of lead use.

In place of a battery 108 any one of a number of circuit embodiments known in the art may be used to provide electrical isolation from an external power source 105 and may further be used to provide isolated electrical power to one or more circuits of the electrical stimulation device 101.

In embodiments of the present invention, an external computing device 102 may functionally interface with other network computing devices, including but not limited to computing devices coupled to or otherwise accessible via the Internet. Such interfaces to other network computing devices may be used, for example, to facilitate the determination or alteration of parametric values of an electrical signal for stimulating tissues through analysis using software in a network computing device, with subsequent control data being sent from the network computing device via the functional interfaces to an external computing device 102, further operationally coupled to a processor 103 in an electrical stimulation device 101. In other words, the external computing device 102 may be configured to functionally interface with at least one other network computing device to determine parametric values of an electrical tissue stimulation signal; and to receive subsequent corresponding control data from the other network computing device via the functional interfaces. The external computing device 102 may be configured to functionally interface with the other network computing device via the Internet.

In embodiments of the present invention, the time-averaged current flow of an electric signal for stimulating tissues may be varied by modifying the duty cycle of the high frequency component of an AMPWM signal. This method of varying the time-averaged current flow may include varying stimulation intensity provided to a subject by an external stimulation device 123 such as, but not limited to, the light intensity of an optical stimulation device, the magnetic field strength of an electromagnetic device, the mechanical action of an electromechanical stimulation device or the sound intensity of an audio stimulation device.

In embodiments of the present invention, the apparatus for providing electrical signals for stimulating tissues may be integrated with other instruments used during periods of therapy. For example, such instruments may be electrically coupled to an electrical stimulation device 101 through auxiliary I/O connectors 16. In other words, the tissue stimulation apparatus may include data collection instruments configured to collect data on a subject during periods of therapy and electrically coupled to the electrical stimulation device 101. Among other things, this approach allows simultaneous collection of instrument data during periods of therapy.

Embodiments of the present invention may include the use of a software program to execute various means of identifying a subject. Such means may include, but are not limited to, electronic or magnetic identification media. Such means may also include, but are not limited to, the use of digital photographs of a subject to both aid in identification of the subject and to provide visual support to aid in proper location for the placement of any leads associated with the apparatus.

Software may also be used to facilitate the playing of music through an external stimulation device 123 for the subject during therapy, with the music being chosen, for example, to enhance therapeutic effect.

Software may also be used to facilitate the playing of educational audio or video media clips for the subject at any time associated with therapy, with the media clips being chosen, for example, to enhance therapeutic effect.

A number of methods have been described for deriving quantities such as the frequency, phase, pulse width duty cycle, and amplitude of electrical signals for stimulating tissues, e.g., signals such as AMPWM signals, that reduce tissue impedance and increase depth of signal penetration. Such derivations are anticipated through either manual means such as those performed by a human, or automatic means such as those performed by computational methods in software, or by any combination of both means. In various methods taught herein, the term "frequency" refers to any singular value or to any range of values that change over a period of time during therapeutic activity (e.g. a "frequency sweep").

Such signals may be used to stimulate brain tissue. According to one method of electrically stimulating tissue, parametric values of an electrical tissue stimulation signal are determined in response to biopotential voltage data obtained from a region of tissue to be stimulated. An electrical stimulation signal having the determined parametric values is then generated and applied to the region of tissue. One exemplary way of determining parametric signal values includes first taking a measure of the EEG activity of at least a portion of the brain, or the EEG of the entire brain, of a subject prior to the generation and application of any electrical signal for the purposes of stimulating brain tissues. Upon collection of EEG activity from the brain for a sufficient period of time, the EEG data is analyzed for any number of relationships. A sufficient period of time for collecting EEG activity may be between, for example, one second and one hour. The relationships for which the EEG data is analyzed may include, but are not limited to, the amount of measured voltage in single frequency components; in composites of multiple frequencies, also known as frequency bands; and/or in frequency band ratios, for the cases of both individual EEG sites and for multiple EEG sites. These relationships may further include, but are not limited to, various statistical analyses involving measured EEG voltages and their frequency and phase components, taken at both individual EEG sites and for multiple EEG sites. These statistical analyses may include, but are not limited to, measures of variance, correlation, and/or coherence. These relationships may further include, but are not limited to, various analyses that provide indication of the spatial origin and/or source localization of the measured EEG, such as that accomplished by performing "inverse EEG" analysis.

Parametric determination may further rely on making comparisons between the findings of the EEG analysis and similar measures known to represent normal brain activity in a healthy normal population of living beings such as human beings. Such a comparison may be performed, for example, for the purpose of quantifying differences between the measured EEG of a subject and the EEG expected in normal brain activity. Such differences are used to identify particular brain sites or regions where frequency and amplitude components of the subject's EEG are either excessive; that is, where they exhibit greater values than normal; diminished; that is, where they exhibit values lower than normal; or highly variable; that is, where they exhibit values that fluctuate more than normal.

Figure 22:
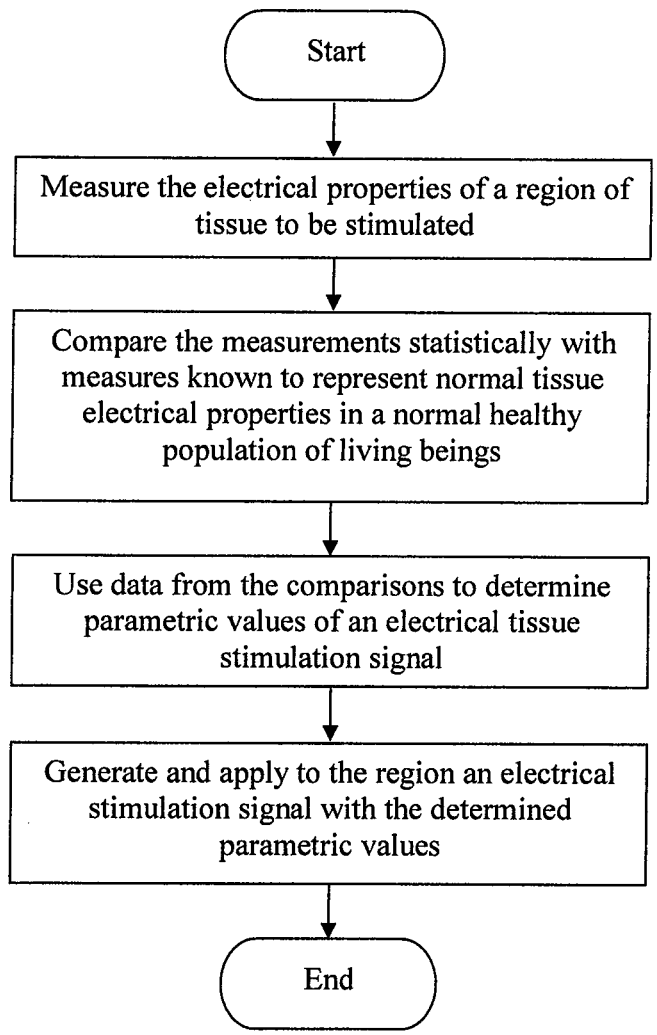
FIG. 22 shows a flow diagram of method of applying therapeutic electrical stimulation, in accordance with an embodiment of the present invention.

As shown in FIG. 22, parametric determination may include selecting quantities such as the frequency, amplitude, and phase components of the low frequency component of an AMPWM signal based on such comparisons in an attempt to achieve normal EEG presentation. By using pulse width modulation for the purpose of varying the duty cycle of the electrical signal of relatively high frequency, the time-averaged current deliverable by that signal can be controlled. Therefore, further to this embodiment, the pulse width duty cycle of the high frequency component of an AMPWM signal is selected based on such comparisons to affect the time averaged current delivered by the AMPWM signal in an attempt to achieve normal EEG presentation.

In one embodiment of this method of parametric determination, the frequencies for the low frequency signal components of the electrical signal, such as an AMPWM signal, are selected to modulate either excessive or diminished EEG activity, as determined by the aforementioned comparative analysis. In other words, determining parametric values may include selecting frequencies for low frequency signal components of an electrical tissue stimulation signal to modulate either excessive or diminished EEG activity, as determined by the comparative analysis. In this embodiment, if excessively high frequency EEG activity were found in a region of the brain, a lower frequency may be used as the low frequency component of the electrical signal for stimulating that region of the brain. In other words, selecting frequencies for low frequency signal components may include selecting a lower frequency as the low frequency component of the electrical signal for stimulating a region of the brain where excessively high frequency EEG activity is found, with a "lower frequency" being defined as between 1 and 20 hertz lower than the value of the identified excessively high EEG frequency. In practice, a progressively lower frequency might be used in therapeutic activity until the excessive EEG activity in a region of the brain reduces to a more normal level. In one embodiment of the invention, the EEG of the brain can be continually monitored during therapeutic activity, providing an indication of the effectiveness of the therapeutic activity.

Figure 24:
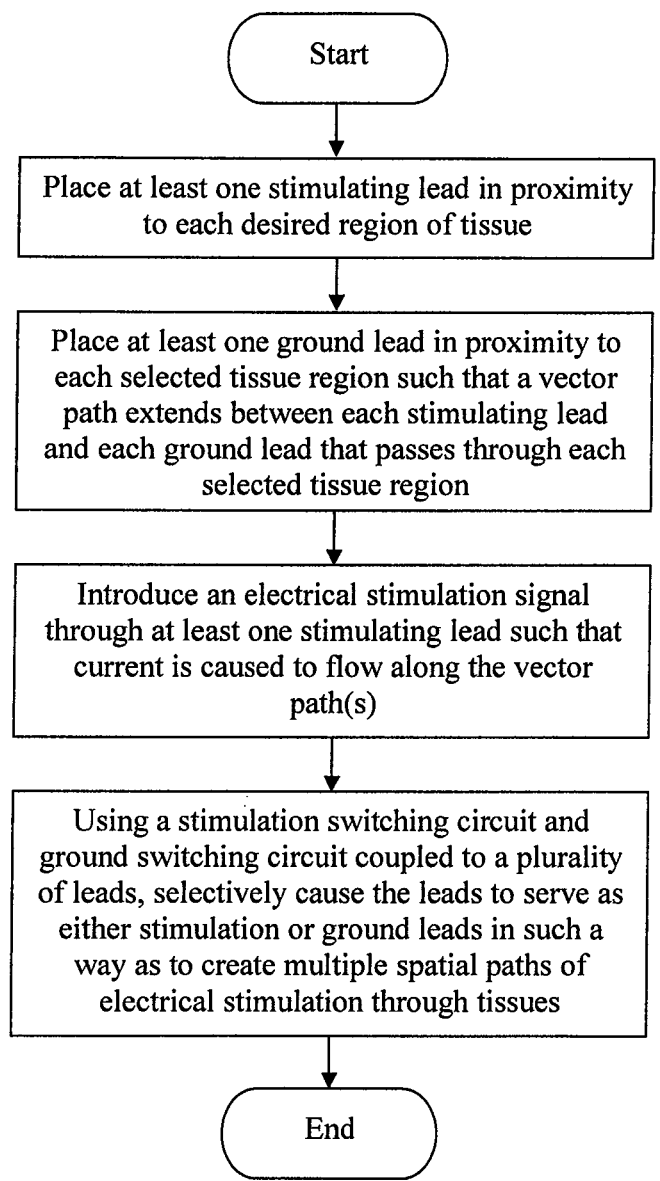
FIG. 24 shows a flow diagram of method of applying therapeutic electrical stimulation, in accordance with an embodiment of the present invention.

In embodiments of the present invention electrical stimulation signals such as AMPWM signals may be directed through desired tissues or tissue regions by introducing such signals so as to cause current to flow through the desired tissues or tissue regions. As shown in FIG. 24, this may be accomplished by first placing any number of stimulating leads 121 in proximity to the tissues or tissue regions to be stimulated, and further placing any number of ground leads 120 in another proximity to the tissues or tissue regions to be stimulated such that a vector path extends between stimulating leads and ground leads and passes through the particular tissues meant to receive electrical stimulation. In other words, at least one stimulating lead 121 and one ground lead 20 are placed in proximity to a tissue region to be stimulated such that a vector path extending between the stimulating lead and the ground lead passes through the tissue region to be stimulated. An electrical stimulation signal is then introduced through the at least one stimulating lead such that current is caused to flow along the vector path through the tissue region between the stimulating lead and the ground lead.

Thus, any number of stimulating leads may, for example, be placed in proximity to the brain tissues where abnormal EEG activity has been determined to exist. Further, any appropriate number of ground leads may be placed in further proximity to the brain tissues so as to create a vector that extends between stimulating leads and ground leads and that passes through the brain tissue to be stimulated. In this arrangement, application of an electrical signal for stimulating brain tissues will cause a current flow through such brain tissue, in an approximate vector direction between stimulating leads and ground leads.

In another embodiment of parametric determination for the purpose of stimulating a brain, a plurality of desirable stimulation frequencies may be determined by EEG analysis as detailed above. As previously taught, a form of an AMPWM signal may be generated by, for example, creating a low frequency component waveform featuring multiple frequency components, as determined by inverse Fourier Transform methods. The plurality of desirable stimulation frequencies may be used to determine a single waveform of multiple low frequency components by inverse Fourier Transform computation, and may be used for creating an AMPWM signal and may further be used for stimulating a brain, as previously described. In other words, the application of inverse Fourier Transform methods may include using inverse Fourier Transform computation to determine from the plurality of desirable stimulation frequencies a single waveform of multiple low frequency components, and the application of an electrical stimulation signal may include using the single waveform to create and use an AMPWM signal to stimulate brain tissue In another embodiment of parametric determination for the purpose of stimulating a brain, EEG data from brain tissue may further be acquired during therapeutic tissue stimulation signal application activity and analyzed at a time generally concurrent to the stimulation signal being applied. In other words, obtaining biopotential voltage data may include acquiring EEG data of brain tissue during therapeutic stimulation signal application activity, and determining parametric values may include analyzing the EEG data as the stimulation signal is being applied. Analysis of the EEG may include the use of one or more of those methods previously described for EEG acquired from brain tissue prior to stimulating the brain, for example. Based on this analysis, comparisons may be made between the acquired EEG presentation and a desired EEG in a normal presentation. In this alternate embodiment, quantities such as the frequency, amplitude and phase components of the low frequency component of an AMPWM signal may be altered based on these comparisons in an attempt to achieve a normal EEG presentation. In this implementation, the pulse width duty cycle of the high frequency component of an AMPWM signal may be altered based on the comparisons to affect the time averaged current delivered by the AMPWM signal in an attempt to achieve normal EEG presentation.

In yet another embodiment of parametric determination for the purpose of stimulating a brain, any number of sensory inputs other than EEG data may be substituted in the methods described herein to enable quantifying of the condition of tissues or any other functional state of a subject. In other words, determining parametric values may include obtaining sensory inputs quantifying the functional state of a subject, and then determining parametric values for the purpose of stimulating brain tissue in response to the sensory inputs. Such sensory inputs may include, but are not limited to, tissue impedance, temperature, oxygen saturation, EMG activity, electrocardiographic activity, biochemical levels, and/or measures involving respiration patterns.

Further to the methods disclosed for deriving quantities such as the frequency, phase, pulse width duty cycle, and amplitude of electrical signals for stimulating tissues, such as an AMPWM signal, a number of methods may be used for controlling the application time of the signals.

For example, the amount of time that an electrical signal for stimulating tissues is to be applied to a subject may be predetermined and set programmatically based on empirical evidence gained from clinical experience, and then controlled by software to start and stop the application of the signal.

Alternatively, software may be provided to start an electrical signal for stimulating tissues and to stop the signal application automatically, as certain measures in tissue electrical properties are achieved. In other words, controlling signal application time may include starting and then automatically stopping an electrical tissue stimulation signal in response to the achievement of certain desired measures of tissue electrical properties. With reference to the method of stimulating brain tissues taught herein, the EEG of the brain may be further acquired during the therapeutic activity and analyzed at a time generally concurrent with the stimulation signal being applied. The electrical signal application may be stopped when any number of predetermined EEG properties is achieved. In other words, controlling signal application time may include acquiring EEG data from brain tissue during therapeutic electrical tissue stimulation activity, analyzing the acquired EEG data as the stimulation signal is being applied, and stopping the electrical signal application when one or more predetermined EEG properties are achieved. This alternative method may include termination of signal application in response to one or more other measures of sensory input including, but not limited to, tissue impedance, temperature, oxygen saturation, EMG activity, electrocardiographic activity, biochemical levels, and measures involving respiration patterns.

Figure 21:
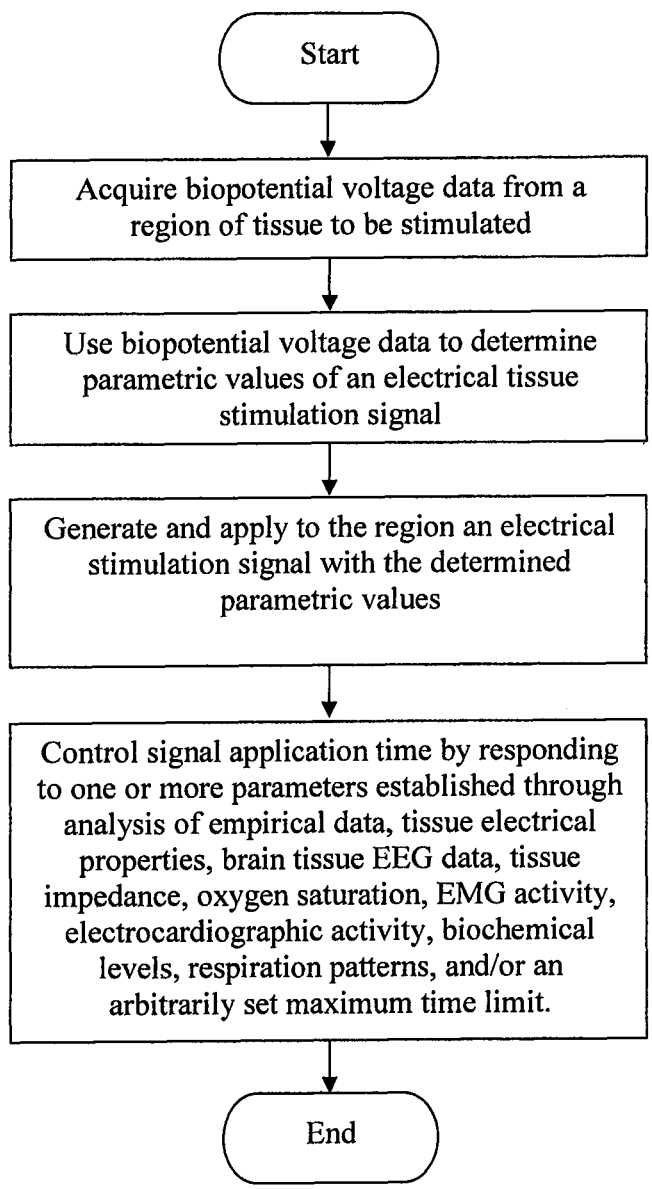
FIG. 21 shows a flow diagram of method of applying therapeutic electrical stimulation, in accordance with an embodiment of the present invention.

Alternatively, and as shown in FIG. 21, automation of signal termination based on sensory input may be combined with predetermination of a time for signal application, such that the electrical signal will not exceed a predetermined time if desired electrical properties of the tissue are not achieved.

Generally, each of the methods disclosed can be applied to tissues that are not brain tissues, such as tissues including, but not limited to, muscles, bones, tendons, ligaments, cartilage, fascia, dermis (i.e., layers of skin), and/or internal organs. Parametric determination generally relies on first taking measures of tissue electrical properties prior to application of any electrical signal for the purposes of stimulating the tissues. Upon collection of tissue electrical property data, an analysis for the purpose of making statistical comparisons between the findings and measures known to represent normal tissue electrical properties in a healthy normal population of living beings, including human beings, may be performed. In other words, a method is provided for electrically stimulating tissue in which parametric values of an electrical tissue stimulation signal may be determined by first taking measures of electrical properties of a region of tissue to be stimulated, making statistical comparisons between the measures and measures known to represent normal tissue electrical properties in a healthy normal population of living beings, determining parametric values of an electrical tissue stimulation signal in response to the comparisons, and then generating and applying to the region of tissue an electrical stimulation signal having the determined parametric values.

In embodiments of the present invention, the method of parametric determination is completed as quantities such as the frequency, amplitude and phase components of the low frequency component of an AMPWM signal are selected based on such comparisons, in an attempt to achieve normal tissue electrical property presentation. By using pulse width modulation for the purpose of varying the duty cycle of a high frequency component of an AMPWM signal, the time-averaged current deliverable by that signal can be controlled. Thus, the pulse width duty cycle of the high frequency component of an AMPWM signal may be selected, based on these comparisons, to affect the time averaged current delivered by the AMPWM signal, in an attempt to achieve normal tissue electrical property presentation.

As described further above, in directing the electrical signals for the purpose of stimulating tissues, in embodiments of the present invention, the electrical signal may be introduced so as to cause current to flow through such tissues, involving first placement of any number of stimulating leads 121 in proximity to the tissues, and further by placing any suitable number of ground leads 120 in another proximity to the tissues. In one placement pattern, a vector direction between stimulating leads 121 and ground leads 120 passes through the particular tissues meant to receive electrical stimulation.

Thus, stimulation of tissues other than a brain may be accomplished by placing any appropriate number of stimulating leads 121 in proximity to the tissues. Correspondingly, any suitable number of ground leads 120 are placed in further proximity to the tissues, so as to create a vector direction between stimulating leads 121 and ground leads 120 that passes through the particular tissue to be stimulated. In this arrangement, application of an electrical signal for stimulating tissues will cause a current flow through the tissues, in an approximate vector orientation between electrodes 122 of stimulating leads 121 and ground leads 120.

In yet another embodiment of parametric determination for the purpose of using electrical signals for stimulating tissues, including brain tissues and tissues that are not brain tissues, a measure of biochemicals, particularly neurochemicals and neurotransmitters, may first be taken from tissues and/or fluids relevant to the tissues to be stimulated. The measures are then analyzed by, for example, making comparisons between the findings of the measure of biochemicals and similar measures known to represent normal levels of the biochemicals in a healthy normal population of living beings, including human beings. Such comparisons may be done for the purpose of quantifying differences that indicate either excessive, that is, greater amounts of certain biochemicals than normal, or diminished, that is, lower amounts of certain biochemicals than normal. In other words, a method is provided that may include determining parametric values of an electrical tissue stimulation signal by taking measures of biochemicals from tissues and/or fluids relevant to the tissues to be stimulated, analyzing the measures, and determining parametric values of an electrical tissue stimulation signal in accordance with the analysis of the measures. An electrical stimulation signal may then be generated and applied to the region. The applied signal may have the determined parametric values and may be configured to reduce tissue impedance and increase depth of signal penetration.

Figure 23:
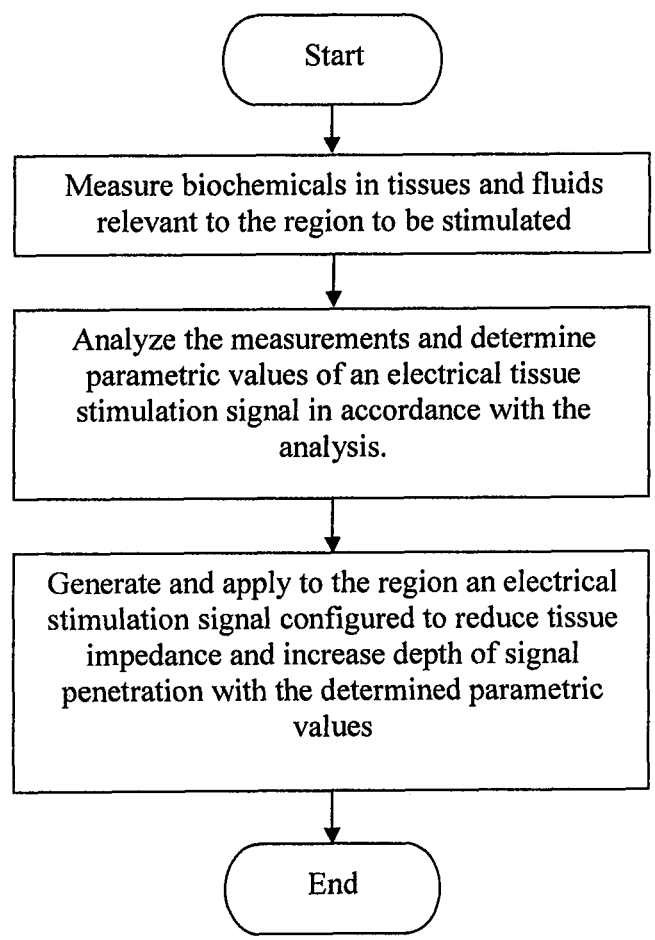
FIG. 23 shows a flow diagram of method of applying therapeutic electrical stimulation, in accordance with an embodiment of the present invention.

As shown in FIG. 23, an embodiment of parametric determination may further include determination of molecular resonant frequencies associated with biochemicals determined to be excessive or diminished in a subject. In this embodiment, an electrical signal for stimulating tissues may be applied for the purpose of affecting abnormal biochemical levels. In other words, determining parametric values in response to the comparisons may include determining electrical signal parameters that will tend to normalize abnormal biochemical levels when such a signal is generated and applied to the subject.

Parametric determination, in these embodiments, may include selecting quantities such as the frequency, amplitude, and/or phase components of the low frequency component of an AMPWM signal, based on the molecular resonant frequencies associated with biochemicals to be used, in an attempt to achieve normal biochemical presentation. The pulse width duty cycle of the high frequency component of an AMPWM signal may be selected based on such comparisons, to affect time averaged current delivered by the AMPWM signal, in an attempt to achieve normal biochemical presentation. In one embodiment of the invention, the involved biochemical levels can be continually or periodically monitored during therapeutic activity, providing an indication of the effectiveness of the therapeutic activity.

In yet another embodiment of parametric determination that relies on making comparisons between the findings of abnormal biochemical levels in a subject, the determination of the frequencies for the low frequency signal component of an electrical signal, such as an AMPWM signal, may be made based on empirical findings of frequencies that are known to be relevant to stimulating the biochemicals, the frequencies being those potentially different than resonant frequencies associated with the biochemicals. For example, the frequencies for the low frequency signal component of an electrical signal, such as an AMPWM signal, may be selected to modulate diminished levels of the neurotransmitter serotonin, the diminished levels being common to such conditions as depression and chronic pain, as determined by the aforementioned comparative analysis. In various examples of published literature, production of serotonin has been shown to be increased by stimuli at a frequency of between about one and 60 hertz, more preferably at about 10 hertz. In accordance with the method taught herein, the low frequency component of an AMPWM signal may therefore be selected to be between about one and 60 hertz, more preferably about 10 hertz, in an attempt to increase serotonin production.

A number of methods are provided for deriving, setting and altering quantities or parameters such as the frequency, phase, pulse width duty cycle, and/or amplitude of electrical signals for stimulating tissues, such as an AMPWM signal, wherein information may be transmitted between an electrical stimulation apparatus as taught herein and a remote location.

According to one such method, measures of electrical parameters used to quantify the condition of tissues or any other appropriate functional state of a subject may first be obtained as described above. Such electrical parameters may include, but are not limited to, tissue impedance, temperature, oxygen saturation, EEG activity, EMG activity, electrocardiographic activity, biochemical levels, and/or measures involving respiration patterns. These measures may be transmitted to a remote location, via a network, such as the Internet or via another communication medium.

Figure 25:
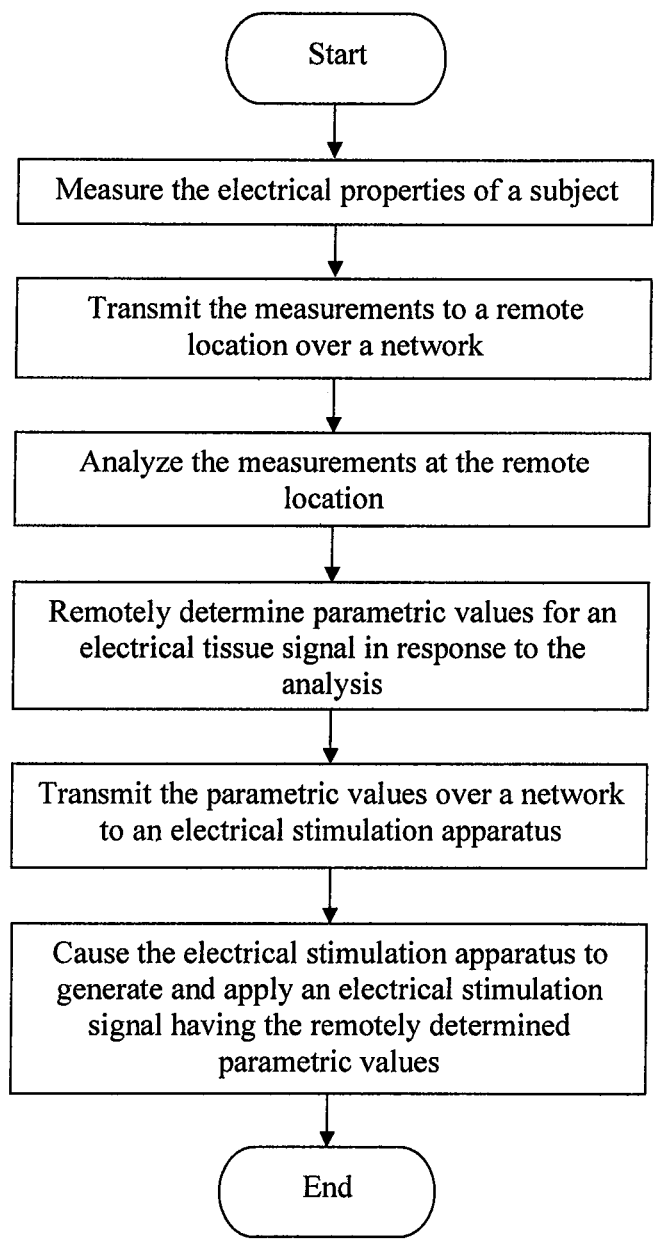
FIG. 25 shows a flow diagram of method of applying therapeutic electrical stimulation, in accordance with an embodiment of the present invention.

As shown in FIG. 25, analysis and comparisons, similar to those described above, may be performed at the remote location for the purpose of determining quantities such as the frequency, phase, pulse width duty cycle, amplitude, start time, and stop time parameters of electrical signals for stimulating tissues, such as an AMPWM signal. The parameters for an electrical signal for stimulating tissues may then be transmitted from the remote location, via a network, such as the Internet or via other communication medium, to an electrical stimulation apparatus as taught herein, and used in the therapeutic application of the electrical signal on a subject. In other words, a method is provided for electrically stimulating tissue that may include the determination of parametric values of an electrical tissue stimulation signal by taking measures of electrical properties of a subject, then transmitting the measures to a remote location via a network such as the Internet, analyzing the measures at the remote location by, for example, making statistical comparisons between the measures and measures known to represent normal tissue electrical properties in a healthy normal population of living beings, remotely determining parametric values of an electrical tissue stimulation signal in response to the analysis, transmitting the parametric values from the remote location via a network such as the Internet to an electrical stimulation apparatus, and causing the electrical stimulation apparatus to generate and apply to a region of the subject's tissue an electrical stimulation signal, e.g., a signal, such as an AMPWM signal, configured to reduce tissue impedance and increase depth of signal penetration, and having the remotely determined parametric values.

Alternatively, according to this method, measures of electrical parameters that are used to quantify the condition of tissues or other appropriate functional state of a subject may be acquired during the therapeutic activity at a time generally concurrent to the application of the stimulation signal. Such electrical parameters may include, but are not limited to, tissue impedance, temperature, oxygen saturation, EEG activity, EMG activity, electrocardiographic activity, biochemical levels, and/or measures involving respiration patterns. These measures may be transmitted to a remote location, via a network, such as the Internet or via other communication medium.

Analysis and comparisons as described herein may be performed at the remote location for the purpose of altering quantities such as the frequency, phase, pulse width duty cycle, amplitude, start time, and/or stop time parameters of electrical signals for stimulating tissues, such as an AMPWM signal. The determined parameters for altering an electrical signal for stimulating tissues may be transmitted from a remote location, via a network, such as the Internet or via other communication medium, to an electrical stimulation apparatus as taught herein, and used in the further therapeutic application of the altered electrical signal on a subject. In other words, taking measures may include acquiring measures of electrical parameters from a subject as a stimulation signal is being applied to the subject, and remotely determining includes altering quantities such as the frequency, phase, pulse width duty cycle, amplitude, start time, and/or stop time parameters of electrical tissue stimulation signals in response to such measures taken as a stimulation signal is being applied.

The analysis and comparisons as taught herein may be performed at the remote location for the purpose of determining changes in the electrical parameters over time, in accordance with the application of therapeutic activities. Parameter changes over time may be transmitted from a remote location, via a network, such as the Internet, or via other communication medium, to a subject or a person of sufficient competence such as a physician, and used to provide an indication of changes in the electrical parameters over time, in accordance with the application of therapeutic activities.

In addition, symptom data may be acquired from a subject and transmitted via a network, such as the Internet, or via another communication medium, from a subject or a person of sufficient competence, such as a physician, to the remote location for the purpose of tracking changes in symptoms associated with a condition of the subject over time, in accordance with the application of therapeutic activities. In other words, symptom data may be acquired from a subject, transmitted to the remote location via a communication medium such as the Internet, and recorded at the remote location. Changes in the subject's symptoms may be tracked by repeating the acquiring, transmitting, and recording of data on the subject's symptoms. This symptom data may be compared to measures of electrical parameters acquired, and transmitted to a remote location either (a) periodically during the therapeutic activity, or (b) at a time generally concurrent with the stimulation signal being applied, as taught herein. A comparison of symptom data and changes in electrical parameters may be made and transmitted from a remote location, via a network, such as the Internet, or via other communication medium, to a subject or a person of sufficient competence such as a physician, and used for the purpose of providing indication of changes in the symptoms over time in accordance with the application of therapeutic activities.

In accordance with the methods taught herein for providing feedback and information about changes in electrical parameters and/or symptoms, such feedback may include, but is not limited to, methods involving statistics or graphical representations of such changes, any method of visually illustrating the changes, and any method of audibly illustrating the changes.

A number of methods are provided for treatment of various conditions using electrical signals for stimulating tissues, such as an AMPWM signal.

Figure 26:
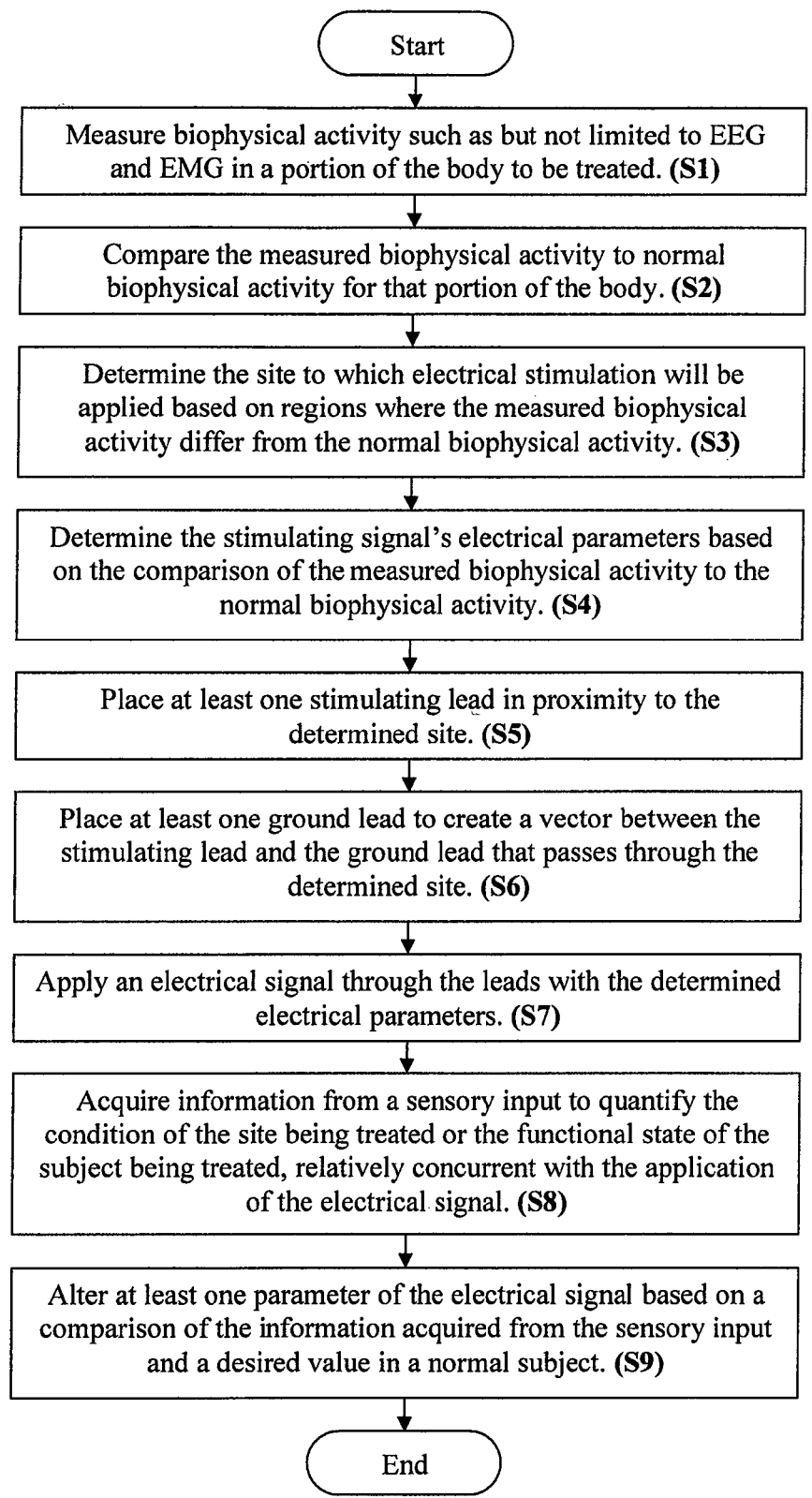
FIG. 26 shows a flow diagram of method of applying therapeutic electrical stimulation, in accordance with an embodiment of the present invention.
Figure 27:
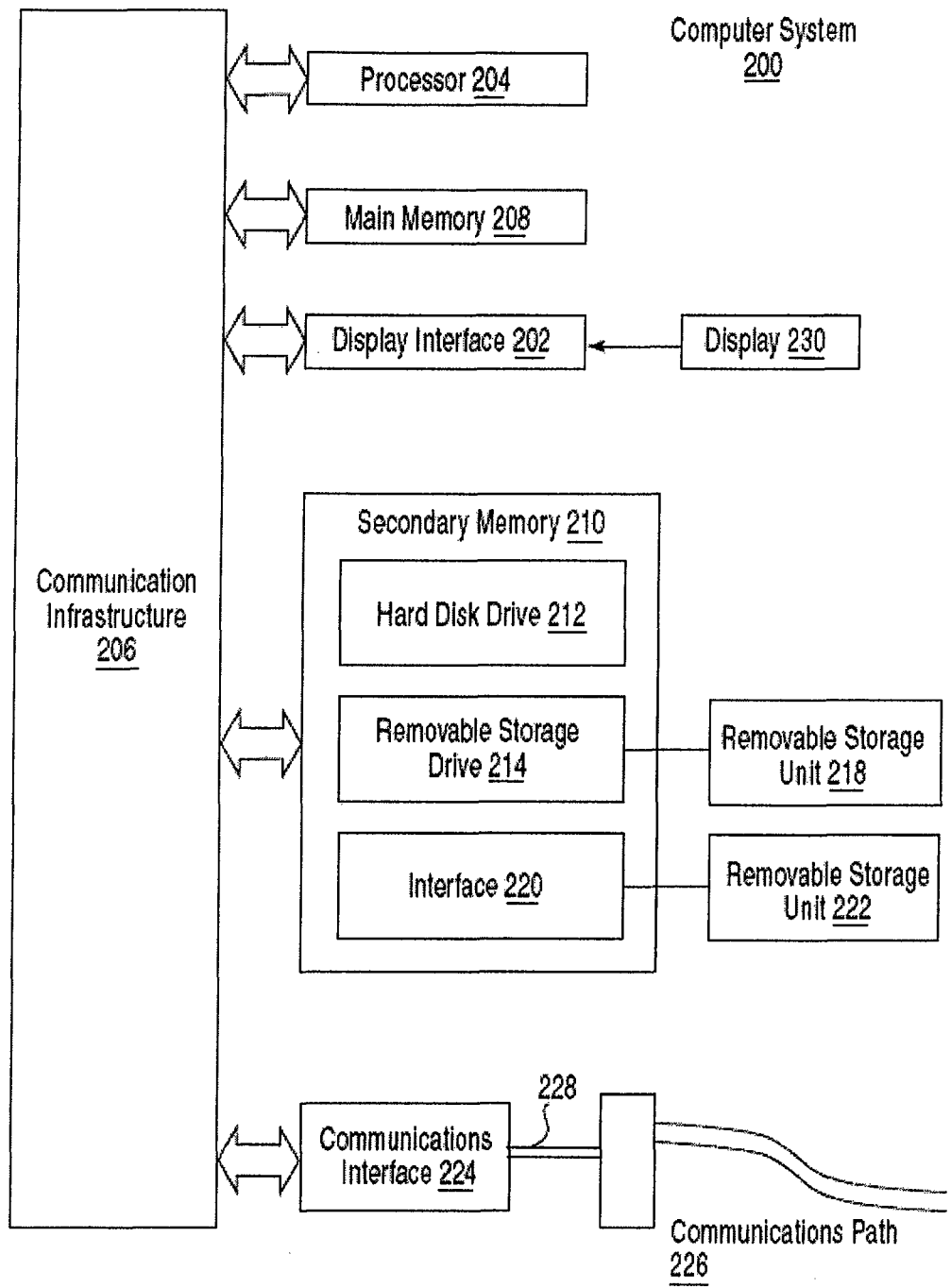
FIG. 27 shows a diagram of a computer system, in accordance with an embodiment of the present invention.

FIG. 26 shows an exemplary flow diagram of exemplary action in accordance with one such method. As shown in FIG. 26, in step S1, biophysical activity such as but not limited to biopotential voltages such as EEG and EMG may be measured in a portion of the subject's body that is to be treated. This portion of the body to be treated may include a portion of the subject's brain, the subject's entire brain, body tissue containing an injury, body tissue near a bone injury, body tissue near a muscle injury, body tissue involved in or near a painful condition, and/or body tissue near a nerve causing health issues for example.

As shown in step S2, the measured biophysical activity may be compared to normal biophysical activity for that portion of the body. The analysis of biophysical activity may involve either biophysical values from individual sites or multiple sites. The analysis may include statistical analyses of biophysical voltages, their frequency components, and/or their phase components. In addition, the statistical analysis may include measures of variance, correlation, and/or coherence. This step, either alone or in connection with steps S3 and S4, as described further below, may be performed either at the location in which the measurements are taken, or at a remote location to which the measurements have been transmitted.

As shown in step S3, the site to which electrical stimulation will be applied may be determined, based on, for example, regions where the measured biophysical levels differ from the normal, desired biophysical activity. The differences in the biophysical levels are quantified and treatment sites may include regions where the frequency or amplitude components of the subject's biophysical levels exhibit greater values than normal, lower values than normal, and/or values that fluctuate more than normal. The site to which the electrical signal is to be applied may include muscles, bones, tendons, ligaments, cartilage, fascia, dermis, and/or internal organs.

As shown in step S4, electrical parameters including, but not limited to, the frequency, phase, pulse width duty cycle, and amplitude may be determined for the electrical signal to be applied to the subject, based on, for example, the analysis performed in step S2, to attempt to bring the subject's biophysical values for the determined site to more normal, desired values.

As shown in step S5, at least one stimulating lead may be placed in proximity to the determined site. As shown in step S6, at least one ground lead may be placed so as to create a vector direction between the stimulating lead and the ground lead that passes through the site to be treated. In this manner, the path of the electrical stimulation will pass through the site to be treated. Any suitable number of stimulation and ground leads may be used.

Figure 9:
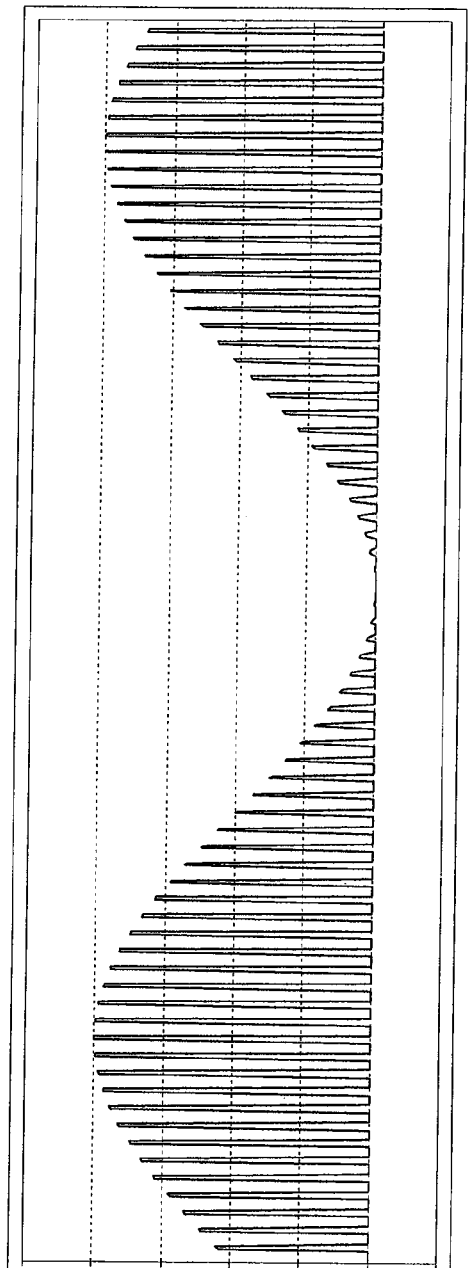
FIG. 9 shows a diagram of a sinusoidal amplitude modulated pulse width modulated signal, for use in accordance with an embodiment of the present invention.
Figure 11:
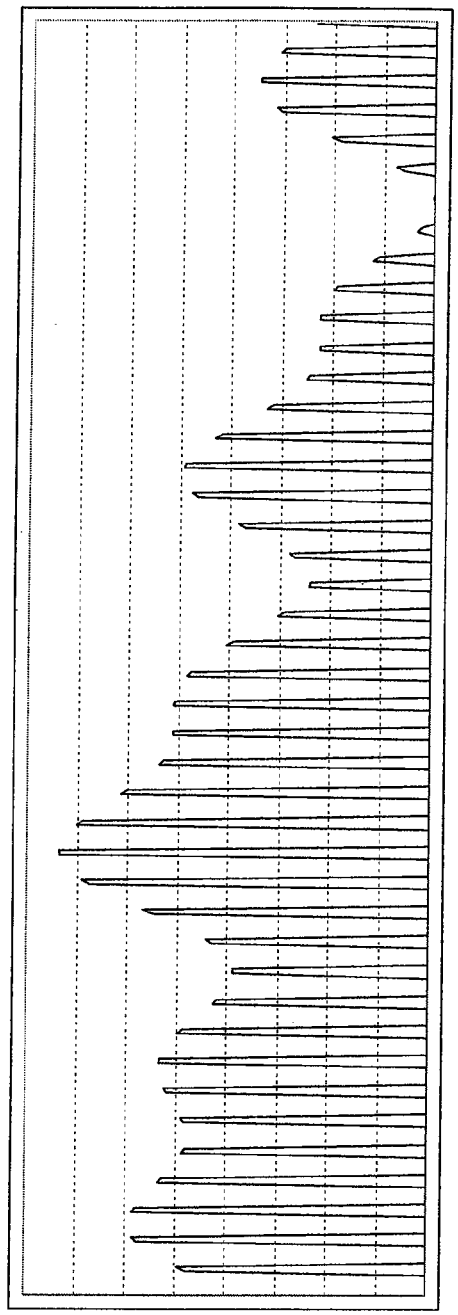
FIG. 11 shows a diagram of a composite sinusoidal amplitude modulated pulse width modulated signal, for use in accordance with an embodiment of the present invention.

As shown in step S7, an electrical signal may be applied through the leads, the electrical signal having the determined parameters such as, but not limited to, frequency, phase, pulse width duty cycle, and/or amplitude. The electrical signal may be, for example, an AMPWM signal, general examples of which are shown in FIGS. 7, 9, and 11, wherein the signal includes a high frequency signal component that is amplitude modulated by one or more low frequency components and further pulse width modulated. The high frequency signal component may be selected, for example, to overcome tissue impedance, and a low frequency signal component may preferably be selected for its therapeutic effect. By using pulse width modulation for the purpose of varying the duty cycle of the electrical signal of relatively high frequency, the time-averaged current deliverable by that signal can be controlled. Therefore, the pulse width duty cycle of the high frequency component may be selected, based on the analysis in S2, to affect the time averaged current delivered by the AMPWM signal. The low frequency component of the electrical signal may be selected to modulate the excessive, diminished, and/or variable biophysical activity at the determined site. The low frequency component of the AMPWM signal may include multiple frequency components. An AMPWM signal with multiple low frequency components is shown in FIG. 11.

As shown in step S8, information may be acquired from a sensory input generally concurrent with the application of the electrical signal, to quantify the condition of either the site being treated with the electrical signal or the functional state of the subject being treated. Such sensory inputs may include measures of biophysical activity, including but not limited to EEG, EMG, tissue impedance, temperature, oxygen saturation, electrocardiographic activity, biochemical levels, and/or respiratory patterns. This monitoring of sensory inputs may occur as a continual process throughout the therapeutic application of the electrical signal. Biophysical activity of the subject may be sampled at times of minimal electrical stimulation signal amplitude, such as at zero amplitude.

As shown in step S9, at least one characteristic parameter of the electrical signal may be altered based on a comparison of the information acquired from the sensory input and a desired value in a normal subject. Electrical signal parameters such as, but not limited to, the frequency, phase, pulse width duty cycle, and/or amplitude of the electrical signal may be altered. The application of the electrical signal may be stopped based on certain measures in tissue electrical properties being achieved. In addition, the particular leads used to apply the electrical stimulation may be varied. The comparison/analysis of the information acquired in step S8 may occur at the location at which the measurements are taken or at a remote location to which the sensory input information has been transmitted.

A central nervous system condition of a subject may be treated by stimulating tissues in close proximity to the vagus nerve using an AMPWM signal. In one arrangement of lead placement, an electrode 122 of any stimulating lead 121 may be adapted to be placed at the posterior base of the neck of the subject near the first, second, or third cervical vertebrae. An electrode 122 of a ground lead 20 may be adapted to be placed on tissue in a position creating a vector between electrodes 122 that passes near the vagus nerve.

A brain of a subject may be treated by stimulating tissues in close proximity to the vagus nerve using an AMPWM signal. In one arrangement of lead placement, an electrode 122 of any stimulating lead 121 may be adapted to be placed at the posterior base of the neck of the subject near the first, second, or third cervical vertebrae. An electrode 122 of a ground lead 20 is adapted to be further placed on tissue, creating a vector between electrodes 122 that passes near the vagus nerve.

Alternatively, a brain of a subject may be treated using an AMPWM signal. In one arrangement of lead placement, an electrode 122 of any stimulating lead 121 may be adapted to be placed on tissue of the subject near an area of the brain identified as having a dysfunction, such as, but not limited to, identification by EEG analysis. An electrode 122 of a ground lead 20 may be adapted to be further placed on tissue near the area of the brain identified as having a dysfunction, creating a vector between electrodes 122 that passes through the area of the brain identified as having the dysfunction.

Tissues containing an injury may also be treated using an electrical tissue stimulation signal that reduces tissue impedance and increases depth of signal penetration, such as an AMPWM signal. In one arrangement of lead placement, an electrode 122 of any stimulating lead 121 may be adapted to be placed on tissue of the subject near the location of the injury. An electrode 122 of a ground lead 20 may be adapted to be further placed on tissue near the location of the injury, creating a vector between electrodes 122 that passes through the injury.

Tissues containing an injury involving a bone may also be treated using a signal, such as an AMPWM signal, configured to reduce tissue impedance and increase signal penetration depth. In one arrangement of lead placement, an electrode 122 of any stimulating lead 121 may be adapted to be placed on tissue of a subject near the bone injury. An electrode 122 of a ground lead 20 may be adapted to be further placed on tissue near the bone injury, creating a vector between electrodes 122 that passes through the bone injury.

Tissues containing an injury involving a muscle may also be treated using a signal, such as an AMPWM signal, configured to reduce tissue impedance and increase signal penetration depth. In one arrangement of lead placement, an electrode 122 of any stimulating lead 121 may be adapted to be placed on tissue of the subject near the muscle injury. An electrode 122 of a ground lead 20 may be adapted to be further placed on tissue near a muscle injury, creating a vector between electrodes 122 that passes through the muscle injury.

Muscle tissues containing a painful condition for a subject, such as a myofascial trigger point, may also be treated using a signal, such as an AMPWM signal, configured to reduce tissue impedance and increase signal penetration depth. In one arrangement of lead placement, an electrode 122 of any stimulating lead 121 may be adapted to be placed on tissue of the subject near the muscle containing a painful condition, such as a myofascial trigger point. An electrode 122 of a ground lead 20 may be adapted to be further placed on tissue near the muscle containing a painful condition, creating a vector between electrodes 122 that passes through the muscle containing a painful condition; i.e., through the myofascial trigger point.

A myofascial trigger point may also be treated using a signal, such as an AMPWM signal, configured to reduce tissue impedance and increase signal penetration depth. In one arrangement of lead placement, an electrode 122 of any stimulating lead 121 may be adapted to be placed on tissue of a subject near a myofascial trigger point. An electrode 122 of a ground lead 20 may be adapted to be further placed on tissue near a myofascial trigger point, creating a vector between electrodes 122 that passes through the myofascial trigger point.

Myofascial pain may also be treated using an electrical tissue stimulation signal that reduces tissue impedance and increases depth of signal penetration, such as an AMPWM signal. In one arrangement of lead placement, an electrode 122 of any stimulating lead 121 may be adapted to be placed on tissue of a subject near the location of myofascial pain. An electrode 122 of a ground lead 20 may be adapted to be further placed on tissue near the location of myofascial pain, creating a vector between electrodes 122 that passes through the tissue involved in myofascial pain.

Conditions associated with central nervous system dysfunction may be treated with an electrical tissue stimulation signal that reduces tissue impedance and increases depth of signal penetration, such as an AMPWM signal. Such conditions may include but are not limited to fibromyalgia syndrome, chronic pain, traumatic brain injury, affective disorders, such as attention deficit disorder (ADD) and attention deficit hyperactivity disorder (ADHD), chronic fatigue, sleep disorders, obsessive compulsive disorder, Tourette Syndrome, depression, anxiety, and addiction.

Conditions associated with abnormal levels of biochemicals including, but not limited to neurotransmitters and/or neurochemicals in tissues, may be treated with an electrical signal for tissue stimulation that reduces tissue impedance and increases depth of signal penetration, such as an AMPWM signal. Such conditions may include, but are not limited to, fibromyalgia syndrome, chronic fatigue, obesity, chronic pain, muscle pain, myofascial pain, myofascial trigger points, and psychological conditions, such as depression.

Conditions may be treated by using an electrical tissue stimulation signal that reduces tissue impedance and increases depth of signal penetration, such as an AMPWM signal, to enhance a body's own healing mechanisms. Such conditions may include, but are not limited to, broken bones, injured tissues, post-surgical wounds, cuts, muscle pain associated with strains, and spasms.

An electrical signal that reduces tissue impedance and increases depth of signal penetration, such as such as an AMPWM signal, may also be used for tissue stimulation for purposes of reducing fatigue, increasing alertness, or increasing mental clarity. In other words, a method for improving a body's function is provided that includes applying an electrical tissue stimulation signal to a subject, where the signal is configured and applied in such a way as to produce one or more beneficial effects such as reducing fatigue, increasing alertness, and increasing mental clarity.

An electrical tissue stimulation signal, e.g., a signal, such as an AMPWM signal, that reduces tissue impedance and increases depth of signal penetration, may also be used for tissue stimulation for purposes of enhancing performance measures associated with, but not limited to, sporting activities, academic activities, and similar competitive endeavors.

An electrical signal, such as an AMPWM signal, that reduces tissue impedance and increases depth of signal penetration, may also be used for tissue stimulation for purposes of advantageously enhancing the function of organs. In one illustrative method, an AMPWM signal may be used to stimulate pancreatic tissues so as to enhance production of insulin, thereby affecting conditions such as diabetes.

For various methods and apparatus taught herein, treatment times may range between about 1 second and about 60 minutes, with low frequency components of an AMPWM signal ranging between about 1 hertz and about 200 hertz, and high frequency components of an AMPWM signal ranging between about 100 hertz and about 1,000,000 hertz. The duty cycle of an AMPWM signal may range between about 1 percent and about 99 percent, and assessment periods used for the purpose of analyzing acquired biopotential voltages and selectively switching the use of leads may range between about 1 second and about 60 seconds.

The following references are incorporated by reference in their entirety:

1. "High-frequency stimulation of the subthalamic nucleus silences subthalamic neurons: a possible cellular mechanism in Parkinson's Disease", Magarinos-Ascone C, Pazo J H Macadar O and Buno W. (Neuroscience 2002; 115(4): 1109-17.

2. "The spatial receptive field of thalamic inputs to single cortical simple cells revealed by the interaction of visual and electrical stimulation", Kara, Pezaris J S, Yurgenson S and Reid, R C. Proc Natl Acad Sci USA 2002 Dec. 10; 99(25): 16261-6.

3. "The anticonvulsant effect of electrical fields", Weinstein S, Curr Neurol Neurosci Rep 2001 March; 1(2):155-61.

4. "Electrical stimulation of the motor cortex in neuropathic pain", Tronnier V, Schmerz 2001 August; 15(4):278-9.

5. "Centromedian-thalamic and hippocampal electrical stimulation for the control of intractable epileptic seizures", Velasco M, Velasco F, Velasco A L, J Clin Neurophysiol 2001 November; 18(6):495-513

The invention is not limited in any way to the embodiments described herein. In this regard, no attempt is made to show structural details of the invention in more detail than is necessary for a fundamental understanding of the method of the invention. The description is intended only to make apparent to those skilled in the art how the several forms of the invention may be embodied in practice.

I claim:

1. A tissue stimulation apparatus comprising an electrical stimulation device that includes a stimulation signal generation circuit configured to generate an electrical tissue stimulation signal comprising a therapeutic signal component and a penetration signal component wherein the penetration signal component is configured to reduce tissue impedance and increase depth of stimulation signal penetration.

2. A tissue stimulation apparatus as set forth in claim 1 in which the stimulation signal generation circuit is configured to generate an amplitude modulated pulse width modulated (AMPWM) signal.

3. A tissue stimulation apparatus as set forth in claim 1 in which the stimulation signal generation circuit comprises a processor configured to control generation of electrical signals by the electrical stimulation device for tissue stimulation.

4. A tissue stimulation apparatus as set forth in claim 3 in which the tissue stimulation apparatus includes an external computing device electrically coupled to the processor and configured to provide a user interface.

5. A tissue stimulation apparatus as set forth in claim 4 in which the external computing device is configured to exchange data and control signals with the processor.

6. A tissue stimulation apparatus as set forth in claim 4 in which the external computing device is configured to allow a user to modify operational parameters of the electrical stimulation device.

7. A tissue stimulation apparatus as set forth in claim 4 in which the external computing device is configured to establish parameters of the electrical signals generated by the device.

8. A tissue stimulation apparatus as set forth in claim 4 in which the external computing device is configured to functionally interface with at least one other network computing device.

9. A tissue stimulation apparatus as set forth in claim 8 in which the external computing device is configured to functionally interface with at least one of the other network computing devices via the Internet.

10. A tissue stimulation apparatus as set forth in claim 9 in which the external computing device is configured to functionally interface with at least one of the other network computing devices to determine parametric values of an electrical tissue stimulation signal, and to receive subsequent corresponding control data from the other network computing device via the functional interfaces.

11. A tissue stimulation apparatus as set forth in claim 3 in which the stimulation signal generation circuit further comprises a digital-to-analog (D/A) converter configured to receive signal parameters from the processor and to generate a corresponding analog voltage representing an electrical signal for stimulating tissues.

12. A tissue stimulation apparatus as set forth in claim 11 in which the stimulation signal generation circuit further comprises a signal conditioning and amplification circuit configured to receive the analog voltage from the D/A converter and to generate a generally equivalent signal having one or more advantageous enhancements selected from the group of enhancements consisting of increased voltage amplitude, decreased signal-to-noise ratio, and increased current capability.

13. A tissue stimulation apparatus as set forth in claim 12 in which the tissue stimulation apparatus includes a plurality of stimulation leads and one or more ground leads configured to conduct electrical energy between tissues and the electrical stimulation device.

14. A tissue stimulation apparatus as set forth in claim 13 in which the stimulation signal generation circuit is configured to selectively control the delivery of stimulating electrical signals to tissues through one or more selected ones of the stimulation leads.

15. A tissue stimulation apparatus as set forth in claim 14 in which the stimulation signal generation circuit further includes a stimulation switching circuit electrically coupled to the processor, the processor and stimulation switching circuit being configured to switch signals from the signal conditioning and amplification circuit to independent electrical conduction paths that are electrically coupled with the respective stimulation leads.

16. A tissue stimulation apparatus as set forth in claim 15 in which the stimulation signal generation circuit further includes a first ground switching circuit electrically coupled with the independent electrical conduction paths and with the processor, the processor and ground switching circuit being configured to selectively switch the independent conduction paths to at least one system ground point.

17. A tissue stimulation apparatus as set forth in claim 1 in which the electrical stimulation device includes:
   a battery connected to other circuits of the apparatus and configured to provide electrical power to other circuits of the electrical stimulation device;
   a battery charger and switching circuit electrically coupled to the battery; and
   a processor electrically coupled to the battery charger and switching circuit, the processor being configured to command the battery charger and switching circuit to decouple the device from an external power source when isolation is desired and to couple the external power source to the battery to charge the battery when isolation is not desired.

18. A tissue stimulation apparatus as set forth in claim 17 in which the electrical stimulation device includes at least one auxiliary control I/O connector electrically coupled with an input-output (I/O) port of the processor, the processor and control I/O connector being configured to provide control signals between the processor and a peripheral device.

19. A tissue stimulation apparatus as set forth in claim 13 in which the apparatus includes at least one lead test port electrically coupled to the processor and configured to electrically couple a conduction interface of one of the leads to the processor, the processor being configured to test the electrical conducting integrity of the lead whose conduction interface has been coupled via the lead test port to the processor.

20. A tissue stimulation apparatus as set forth in claim 19 in which the processor is configured to output an electrical signal of known properties to the lead whose conduction interface has been coupled via the lead test port to the processor, and to acquire and test the resulting electrical signal conducted through that lead and returned to the processor through the lead test port.

21. A tissue stimulation apparatus as set forth in claim 20 in which processor is configured to determine the electrical conducting integrity of the lead whose conduction interface has been coupled via the lead test port to the processor, by comparing the electrical signal of known properties to the signal conducted through that lead.

22. A tissue stimulation apparatus as set forth in claim 1 in which the tissue stimulation apparatus includes one or more external stimulation devices electrically coupleable to the electrical stimulation device.

23. A tissue stimulation apparatus as set forth in claim 22 in which the one or more external stimulation devices include one or more devices selected from the group of devices consisting of an optical device, an electromagnetic device, and electromechanical device, and an audio device.

24. A tissue stimulation apparatus as set forth in claim 22 in which the one or more external stimulation devices include an optical device comprising eyeglasses adapted to carry illuminating devices.

25. A tissue stimulation apparatus as set forth in claim 22 in which the one or more external stimulation devices include an optical device comprising one or more displays for showing images.

26. A tissue stimulation apparatus as set forth in claim 22 in which the one or more external stimulation devices include an audio device adapted to play music.

27. A tissue stimulation apparatus as set forth in claim 1 in which the tissue stimulation apparatus includes data collection instruments configured to collect data on a subject during periods of therapy and electrically coupled to the electrical stimulation device.

28. A tissue stimulation apparatus as set forth in claim 13 in which the tissue stimulation apparatus includes a biopotential acquisition device configured to measure biopotential voltage of tissues to be stimulated.

29. A tissue stimulation apparatus as set forth in claim 28 in which the biopotential acquisition device includes an amplifier module comprising a biopotential amplifier.

30. A tissue stimulation apparatus as set forth in claim 29 in which the biopotential acquisition device includes at least one biopotential acquisition lead and at least one ground lead.

31. A tissue stimulation apparatus as set forth in claim 30 in which the biopotential amplifier module is electrically coupleable to the electrical stimulation device through anyone or more connectors selected from the group of connectors consisting of stimulation lead connectors, auxiliary power supply connector, control I/O connectors, and auxiliary I/O connectors of the electrical stimulation device.

32. A tissue stimulation apparatus as set forth in claim 31 in which the biopotential acquisition device is configured to measure anyone or more biopotential voltages selected from the group of biopotential voltages consisting of electroencephalographic (EEG) voltage, electromyographic (EMG) voltage, and electrocardiographic voltage.

33. A tissue stimulation apparatus as set forth in claim 30 in which the tissue stimulation apparatus is configured for the biopotential amplifier to measure biopotential voltage of tissue as the electrical stimulation device provides stimulation to the tissue.

34. A tissue stimulation apparatus as set forth in claim 33 in which the biopotential acquisition device includes at least one inductor electrically coupled to the electrical stimulation device and operatively coupleable to at least one biopotential acquisition lead, the electrical stimulation device and the at least one inductor being configured to deliver tissue stimulation signals through the at least one biopotential acquisition lead.

35. A tissue stimulation apparatus as set forth in claim 33 in which the biopotential acquisition device includes one or more inductors electrically coupled to the electrical stimulation device and operatively coupleable to one or more respective biopotential acquisition leads, the electrical stimulation device and inductors being configured to selectively deliver tissue stimulation signals through the one or more biopotential acquisition leads.

36. A tissue stimulation apparatus as set forth in claim 33 in which the biopotential acquisition device includes at least one adjunct switching circuit and an adjunct switching control electrically coupled to the electrical stimulation device, the adjunct switching circuit being operatively coupleable to at least one biopotential acquisition lead, the electrical stimulation device and an adjunct switching control being configured to selectively connect the electrical stimulation device to selected leads to transmit tissue stimulation signals to the selected leads and to connect selected leads to the biopotential amplifier to transmit biopotential voltages to the biopotential amplifier.

37. A tissue stimulation apparatus as set forth in claim 30 in which the electrical stimulation device is configured to use at least one biopotential acquisition lead for both acquiring biopotential voltage and delivering an electrical tissue stimulation signal.

38. A tissue stimulation apparatus as set forth in claim 37 in which the electrical stimulation device is configured to use at least one biopotential acquisition lead for simultaneously acquiring biopotential voltage and delivering an electrical tissue stimulation signal.

39. A tissue stimulation apparatus as set forth in claim 38 in which the electrical stimulation device is configured to selectively sample biopotential voltage data from the biopotential acquisition device at times of minimal electrical stimulation signal amplitude.

40. A tissue stimulation apparatus as set forth in claim 39 in which the electrical stimulation device is configured to selectively sample biopotential voltage data from the biopotential acquisition device over assessment periods of between about 1 second and about 60 seconds.

41. A tissue stimulation apparatus as set forth in claim 39 in which the electrical stimulation device is configured to selectively sample biopotential voltage data from the biopotential acquisition device at times of minimal electrical stimulation signal amplitude within the period of a high frequency signal component of an AMPWM signal.

42. A tissue stimulation apparatus as set forth in claim 1 in which the electrical stimulation device is configured to select the frequencies of a high frequency signal component of an AMPWM signal to be multiples of integral powers of two.

43. A tissue stimulation apparatus as set forth in claim 42 in which the electrical stimulation device is configured to select the frequencies of a high frequency signal component of an AMPWM signal to be integral multiples of 256.

44. A tissue stimulation apparatus as set forth in claim 42 in which the electrical stimulation device is configured to mathematically analyze acquired biopotential voltage data using a Fourier Transform analysis whereupon a number of samples per second is equal to an integral power of two.

45. A tissue stimulation apparatus as set forth in claim 30 in which the tissue stimulation apparatus is configured to use biopotential voltage data to determine parametric values of an electrical tissue stimulation signal.

46. A tissue stimulation apparatus as set forth in claim 45 in which an external computing device is configured to determine parametric value of an electrical tissue stimulation signal in response to biopotential voltage data obtained by the biopotential acquisition device and to send corresponding control data to the processor.

47. A tissue stimulation apparatus as set forth in claim 46 in which the biopotential acquisition device is an EEG acquisition device and the external computing device is configured to determine parametric value of an electrical tissue stimulation signal in response to EEG data obtained by the EEG acquisition device and to send corresponding control data to the processor.

48. A tissue stimulation apparatus as set forth in claim 46 in which the tissue stimulation apparatus is configured to use at least one biopotential acquisition lead as either a conduction path for an electrical tissue stimulation signal, a conduction path for carrying a biopotential voltage to the biopotential amplifier, or a ground.

49. A tissue stimulation apparatus as set forth in claim 48 in which the processor is configured to selectively switch a biopotential acquisition lead to an apparatus ground point by sending corresponding control signals to the second ground switching circuit.

50. A tissue stimulation apparatus as set forth in claim 46 in which the processor is configured to differentially compare biopotential voltages at more than one acquisition site on a tissue by selectively using biopotential acquisition leads as reference leads to the biopotential amplifier or as differential leads to the biopotential amplifier.

51. A tissue stimulation apparatus as set forth in claim 1 in which the tissue stimulation apparatus includes an impedance testing circuit configured to monitor the impedance of tissues, the apparatus being configured to determine parametric values of an electrical tissue stimulation signal in response to tissue impedance data acquired by the impedance testing circuit.

52. A tissue stimulation apparatus as set forth in claim 51 in which the impedance testing circuit is coupled to the electrical stimulation device and a biopotential amplifier of a biopotential acquisition device and is configured to monitor the impedance of tissues in contact with at least one ground lead and at least one biopotential acquisition lead of the biopotential acquisition device and to transfer such data to the processor.

53. A tissue stimulation apparatus as set forth in claim 51 further including an external computing device coupled to the processor and configured to analyze tissue impedance data and to send corresponding control data to the processor for altering parametric parameters of electrical tissue stimulation signals.

54. A tissue stimulation apparatus as set forth in claim 1 in which the tissue stimulation apparatus includes an impedance testing circuit that is coupled with the biopotential amplifier of a biopotential acquisition device and is configured to monitor biopotential voltage integrity.

55. A tissue stimulation apparatus as set forth in claim 54 in which the tissue stimulation apparatus is configured to indicate to a user when good biopotential voltage integrity is achieved.

56. A tissue stimulation apparatus as set forth in claim 54 in which the tissue stimulation apparatus is configured to generate an alert when biopotential voltage integrity is lost.

57. A tissue stimulation apparatus as set forth in claim 1 in which the tissue stimulation apparatus comprises:
  a sensor set;
  an independent biopotential voltage measurement apparatus; and
  an adjunct electrical stimulation apparatus operatively connected between the sensor set and the independent biopotential voltage measurement apparatus, operatively coupled to the electrical stimulation device, and configured to transmit to the sensor set electrical tissue stimulation signals received from the electrical stimulation device, to transmit biopotential voltage from the sensor set to the independent biopotential voltage measurement apparatus, and to receive control signals from a processor of the electrical stimulation device.

58. A tissue stimulation apparatus as set forth in claim 57 in which the biopotential measurement apparatus is an EEG measurement apparatus and the sensor set is an EEG sensor set.

59. A tissue stimulation apparatus as set forth in claim 57 in which the sensor set comprises at least one electrode and a cap configured to position the at least one electrode and to be worn by a subject.

60. A tissue stimulation apparatus as set forth in claim 57 in which in which the adjunct electrical stimulation apparatus includes:
   an adjunct switching control operatively coupled to the processor of the electrical stimulation device;
   a plurality of adjunct switching circuits operatively coupled to the adjunct switching control, to the electrical stimulation device, to the independent biopotential measurement apparatus, and to respective electrodes of the sensor set; and
   the processor and adjunct switching control are configured to provide selectable conduction pathways for tissue stimulation signals between the electrical stimulation device and the electrodes of the sensor set, and for biopotential voltages between the electrodes of the sensor set and the biopotential voltage measurement apparatus.

61. A tissue stimulation apparatus as set forth in claim 60 in which in which the processor and adjunct switching circuits are configured to provide selectable conduction pathways between the electrodes of the sensor set and a ground.

62. A tissue stimulation apparatus as set forth in claim 57 in which the adjunct electrical stimulation apparatus includes:
   a ground switching circuit operatively coupled to the processor of the electrical stimulation device, to the biopotential amplifier, and by conduction paths to respective electrodes of the sensor set;
   a plurality of inductors operatively coupled to the electrical stimulation device and to the conduction paths; and
   the processor and ground switching circuit are configured to provide selectable conduction pathways for tissue stimulation signals between the electrical stimulation device and the electrodes of the sensor set, and for biopotential voltages between the electrodes of the sensor set and the biopotential voltage measurement apparatus.

63. A tissue stimulation apparatus as set forth in claim 62 in which the processor and ground switching circuit are configured to provide selectable conduction pathways between the electrodes of the sensor set and a ground.

64. A tissue stimulation apparatus as set forth in claim 60 in which the adjunct electrical stimulation apparatus includes at least one switching control conductor electrically coupled to an adjunct switching circuit and configured to determine the state of the adjunct switching circuit and a conduction path provided to a corresponding electrode of the sensor set.

65. A tissue stimulation apparatus as set forth in claim 57 in which the processor of the electrical stimulation device and the adjunct switching control are configured to:
   direct biopotential voltage from selected electrodes of the sensor set to the biopotential measurement apparatus by selective switching via the adjunct switching control operated by the processor when a biopotential voltage measurement is required;
   to direct a tissue stimulation signal from the electrical stimulation device to selected electrodes of the sensor set by selective switching via the adjunct switching control operated by the processor when tissue stimulation is required; and
   to couple an electrode of the sensor set to ground by selective switching via the adjunct switching control operated by the processor when grounding of an electrode is desired.

66. A tissue stimulation apparatus as set forth in claim 1 and further comprising:
   a mobile apparatus carrying the electrical stimulation device; and
   a material supplies storage and use apparatus carried by the mobile apparatus and configured to carry consumable supplies for use in administering tissue stimulation signals to a subject.

67. A tissue stimulation apparatus as set forth in claim 66 in which the material supplies storage and use apparatus is configured to carry any number of consumable supplies selected from the group of supplies consisting of conductive pastes, conductive gels, cleaning materials, cleaning agents, and supporting materials.

68. A tissue stimulation apparatus as set forth in claim 66 in which the material supplies storage and use apparatus comprises a plurality of receptacles configured to store any number of items selected from the group of items consisting of a waste, conductive gel, conductive paste, cleaning materials, alcohol, supporting materials, and electrodes.

69. A tissue stimulation apparatus as set forth in claim 66 in which the material supplies storage and use apparatus includes an electrode storage receptacle configured to store and block light from reaching lead electrodes comprising photosensitive materials.

70. A tissue stimulation apparatus as set forth in claim 66 in which the tissue stimulation apparatus includes one or more sensors carried by the material supplies and use apparatus and configured to sense the quantities of materials stored in receptacles of the material supplies storage and use apparatus.

71. A tissue stimulation apparatus as set forth in claim 66 in which the tissue stimulation apparatus includes an external computing device coupled to the one or more sensors and configured to manage inventory in response to signals acquired from the one or more sensors.

72. A tissue stimulation apparatus as set forth in claim 71 in which the tissue stimulation apparatus is configured to generate an alert when inventory of any material reaches a predetermined low point.

73. A tissue stimulation apparatus as set forth in claim 71 in which the tissue stimulation apparatus is configured to order materials necessary to replenish inventory when a predetermined low point is reached.

74. A tissue stimulation apparatus as set forth in claim 71 in which the tissue stimulation apparatus is configured to order materials by interfacing with a communications network.

75. A tissue stimulation apparatus as set forth in claim 66 in which the electrical stimulation apparatus is configured to provide stimulation through composite stimulation leads, the composite stimulation leads comprising a combination of stimulation leads and ground leads.

76. A tissue stimulation apparatus as set forth in claim 75 in which the composite stimulation leads include external stimulation device cables.

* * * * *